United States Patent [19]

Murakata et al.

[11] Patent Number: 4,923,986

[45] Date of Patent: May 8, 1990

[54] DERIVATIVES OF PHYSIOLOGICALLY ACTIVE SUBSTANCE K-252

[75] Inventors: Chikara Murakata, Saitama; Akira Sato, Tokyo; Mitsuru Takahashi, Kanagawa; Eiji Kobayashi, Shizuoka; Makoto Morimoto, Shizuoka; Shiro Akinaga, Shizuoka; Tadashi Hirata; Kenichi Mochida, both of Kanagawa; Hiroshi Kase; Koji Yamada, both of Tokyo; Kazuyuki Iwashashi, Kanagawa, all of Japan

[73] Assignee: Kyowa Hakko Kogyo Co., Ltd., Tokyo, Japan

[21] Appl. No.: 273,519

[22] PCT Filed: Mar. 9, 1987

[86] PCT No.: PCT/JP87/00144

§ 371 Date: Nov. 8, 1988

§ 102(e) Date: Nov. 8, 1988

[87] PCT Pub. No.: WO88/07045

PCT Pub. Date: Sep. 22, 1988

[51] Int. Cl.$^5$ .............. C07D 498; C07D 22; A61K 31/55

[52] U.S. Cl. .................. 540/545; 540/543

[58] Field of Search .................. 540/545, 543

[56] References Cited

U.S. PATENT DOCUMENTS 4,555,402 11/1985 Matsuda et al.

FOREIGN PATENT DOCUMENTS

| | | |
|---|---|---|
| 60-185719 | 9/1985 | Japan. |
| 61-176531 | 8/1986 | Japan. |
| 61-268687 | 11/1986 | Japan. |
| 0120388 | 6/1987 | Japan .................. 540/545 |
| 62-120388 | 6/1987 | Japan. |
| 62-155284 | 7/1987 | Japan. |
| 62-155285 | 7/1987 | Japan. |
| 62-164626 | 7/1987 | Japan. |
| 62-240689 | 10/1987 | Japan. |
| 0240689 | 10/1987 | Japan .................. 540/545 |

OTHER PUBLICATIONS

Chem. Abstracts, 101, 55460j, (1984).
Chem. Abstracts, 105, 187430s, (1986).
Chem. Abstracts, 104, 31427q, (1986).
J. Antibiotics, 30(4), 275-282, (1977), Omura et al., "A New Alkaloid AM-2282 of Streptomyces Origin . . . ".
J. Antibiotics, 39(8), 1066, (1986), Nakanishi et al., "K-252b, c and d, Potent Inhibitors of Protein Kinase C . . . ".
J. Antibiotics, 39(8), 1072, (1986), Yasuzawa et al., "The Structures of the Novel Protein Kinase C . . . ".
J.C.S. Chem. Comm., p. 800, (1978), Furasaki et al., "X-Ray Crystal Structure of Staurosporine . . . ".
J. Antibiotics, 38(10), 1437-1439, (1985), Sezaki et al., "A New Antibiotic SF-2370 Produced by Actinomadura".
J. Antibiotics, 30(4), 275-282, (1977), Omura et al., "A New Alkaloid AM-2282 of Streptomyces Origin . . . ".
J.C.S. Chem. Comm., 800-801, (1978), Furasaki et al., "X-Ray Crystal Structure of Staurosporine . . . ".
J. Antibiotics, 38(10), 1437-1439, (1985), Sezaki et al., "A New Antibiotic SF-2370 . . . ".

*Primary Examiner*—Mukund J. Shah
*Assistant Examiner*—E. C. Ward
*Attorney, Agent, or Firm*—Michael N. Meller

[57] ABSTRACT

The present invention relates to novel derivatives of K-252, (8R*, 9S*, 11S*)-(−)-9-hydroxy-9-methoxycarbonyl-8-methyl-2,3,9,10-tetrahydro-8,11-epoxy-1H,8H,11H-2,7b,11a-triazadibenzo[a,g]cycloocta-[c,d,e,]trinden-1-one, and the compounds are represented by formula (I):

wherein $W_1$, $W_2$, $R^1$, $R^2$, $R^3$, $R^4$, X and Y represent various substituents. The compounds are physiologically active substances that inhibit protein kinase C and exhibit an antitumor activity, and are useful as medicines.

4 Claims, No Drawings

DERIVATIVES OF PHYSIOLOGICALLY ACTIVE SUBSTANCE K-252

TECHNICAL FIELD

The present invention relates to novel compounds which inhibit protein kinase C (hereinafter referred to as C-kinase) and have pharmacological activities such as anti-tumor activity.

BACKGROUND ART

C-kinase is a protein kinase which is activated depending upon phospholipids and calcium and widely distributed over tissues and organs in the living body. It has been reported that this enzyme plays an extremely important role in cell membrane receptor transduction mechanism in which many hormone, neurotransmitters, etc. are concerned. As examples of physiological response induced by signal transduction system in which C-kinase participates, there have been reported serotonin release from platelets, lysosomal enzyme release and aggregation. superoxide formation and lysosomal enzyme release from neutrophil leukocytes, epinephrine release from adrenal medulla, secretion of aldosterone from renal glomerulus, secretion of insulin from Langerhans' islet, histamine release from mast cells, acetylcholine release from ileum, contraction of vascular smooth muscle, and the like. C-kinase is also supposed to be concerned in cell growth and carcinogenetic mechanism [Y. Nishizuka, Science, 225, 1365 (1984); Rasmusen et al., Advance in Cyclic Nucleotide and Protein Phosphorylation Research, vol. 18, p. 159, edited by P. Greengard and G. A. Robinson, Raven Press, New York, 1984]. It is expected that a wide variety of diseases such as diseases of the circular system, inflammatory diseases, allergy an tumor can be prevented or treated by artificially inhibiting C-kinase activity by the use of inhibitors, etc.

On the other hand, it has been found that antipsychotic drugs such as trifluoperazine and chlorpromazine, dibenamine and tetracaine which are known as local anesthetics, calmodulin inhibitor W-7 [N-(6-aminohexy)-5-chloro-1-naphthalenesulfonamide], etc. posssess C-kinase inhibitory activity, but the C-kinase inhibitory activity is low in any of these drugs [Y. Nishizuka et al., J. Biol. Chem., 255, 8378 (1980); R. C. Schatzman et al., Biochem. Biophys. Res. Commun., 98, 669 (1981); B. C. Wise et al., J. Biol. Chem., 257, 8489 (1982)].

K-252 and KT-5556 represented by the following formula are known (with K-252, see Japanese Published Unexamined Patent Application No. 41489/85 and U.S. Pat. No. 4,555,402; with KT-5556, see Japanese Published Unexamined Patent Application No. 176531/86).

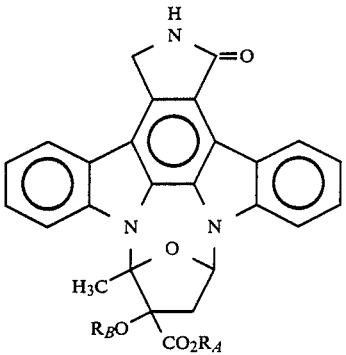

K-252: $R_A$=$CH_3$, $R_B$=H
KT-5556: $R_A$=H, $R_B$=H

In Japanese Published Unexamined Patent Application No. 41489/85, it is described that K-252 has activity to inhibit histamine release and anti-allergic activity. In Japanese Published Unexamined Patent Application No. 176531/86, it is described that KT-5556 has activity to inhibit histamine release. Further, compounds that are assumed to be identical with K-252 or KT-5556 have been reported as antibacterial substances [M. Senzaki et al., J. Antibiotics, 38 (10), 1437 (1985)]. In this publication, a compound of the above formula wherein $R_A$=$CH_3$ and $R_B$=Ac is also disclosed.

Furthermore, Staurosporine having the following structure and antibacterial activity is known as a compound having a structure relatively akin to that of K-252 [S. Omura et al., J. Antibiotics, 30 (4), 275 (1977), A. Furusaki et al., J. Chem. Soc. Chem. Commun., 800 (1978), Japanese Published Unexamined Patent Application No. 185719/85].

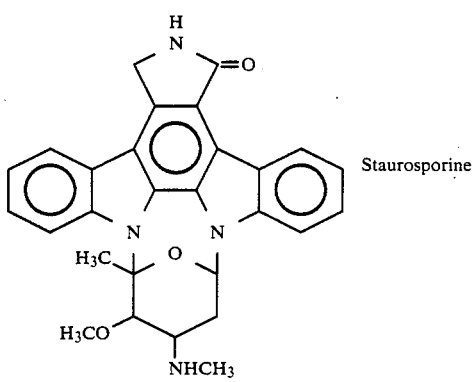

Staurosporine

DISCLOSURE OF THE INVENTION

According to the present invention, there are provided novel derivatives of K-252 represented by formula (I) and pharmacologically acceptable salts thereof.

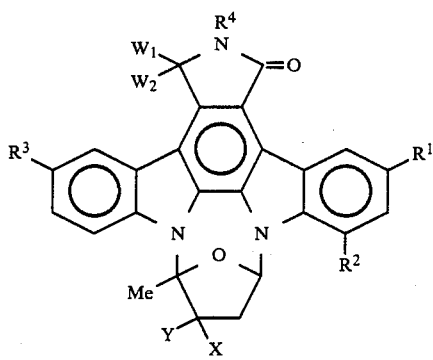

In the formula, $R^1$ represents hydrogen, methyl, hydroxy, hydroxymethyl, lower alkoxy, bromine, chlorine or —$NR^5R^6$ (wherein either $R^5$ or $R^6$ is hydrogen and the other is hydrogen, carbamoyl or lower alkylaminocarbonyl, or both are lower alkyl) and $R^3$ is hydrogen, or $R^1$ and $R^3$ are the same and represent hydrosy, lower alkoxy or amino. $R^2$ is hydrogen or amino, and $R^4$ is hydrogen, chlorine, carbamoyl, lower alkyl, amino or —$CH_2CH_2R^7$ (wherein $R^7$ is bromine, amino, di-lower alkylamino, hydroxy or hydroxysubstituted lower alkylamino).

$W_1$ and $W_2$ are hydrogen or both are combined together to represent oxygen. X is hydrogen, formyl, lower alkoxycarbonyl,

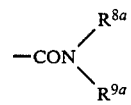

(wherein $R^8$ and $R^9$ are independently hydrogen, lower alkyl or hydroxy-substituted lower alkyl; or $R^8$ is hydrogen and $R^9$ is hydroxy), $CH_2A$ {wherein A is hydroxy, azido, lower alkylthio, lower alkylsulfenyl,

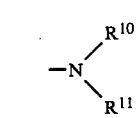

[wherein either $R^{10}$ or $R^{11}$ is hydrogen and the other is hydrogen, lower alkyl, allyl, carboxylic acid-substituted lower alkyl, dihydroxysubstituted lower alkyl, a residue of an α-amino acid in which the hydroxy of the carboxylic acid is removed or lower alkoxycarbonyl-substituted lower alkyl; or both are lower alkyl or chlorine-substituted lower alkyl; or $R^{10}$ and $R^{11}$ are combined together to form —$CH_2CH_2BCH_2CH_2$— (wherein B is —$CH_2$—, —NH—, —S— or —O—)], —N=CH—N-$Me_2$ (wherein Me is methyl), —$OCOCH_2CH_2CO_2H$ or

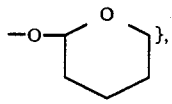

or —CH=$NR^{12}$ (wherein $R^{12}$ is hydroxy, amino, guanidino or 2-imidazoylamino).

Y is hydroxy or carbamoyloxy; or X and Y are combined together to form, as —X—Y—, O=, —$CH_2O$—, —$CH_2OCOO$—, —$CH_2$—O—CS—O—, —$CH_2$—NR-$^{13}$—CO—O— (wherein $R^{13}$ is hydrogen, lower alkyl, allyl, formylmethyl, —$CH_2CH(OH)$—$CH_2OH$,

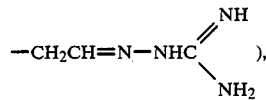

—$CH_2$—NH—CS—O—, —$CH_2$—O—SO—O— or

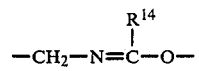

(wherein $R^{14}$ is lower alkyl or lower alkylthio).

With the proviso that $W_1$ and $W_2$ are combined together to represent oxygen, $R^1$, $R^2$ and $R^3$ are all hydrogen. When $R^4$ is lower alkyl, amino or —$CH_2CH_2R^7$, $W_1$ and $W_2$ are combined together to represent oxygen. When Y is carbamoyloxy, $R^1$, $R^2$, $R^3$, $W_1$ and $W_2$ are all hydrogen, $R^4$ is carbamoyl and X is lower alkoxycarbonyl. When $R^4$ is chlorine, $R^1$, $R^2$, $R^3$, $W_1$ and $W_2$ are all hydrogen and X is lower alkoxycarbonyl. When X is hydrogen, formyl,

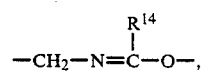

(wherein $R^{8a}$ and $R^{9a}$ are independently hydrogen, lower alkyl or hydroxy-substituted lower alkyl), $CH_2Aa$ (wherein the Aa representation is the same as the above A representation excluding hydroxy and amino) or —CH=N—$R^{12}$, $R^1$, $R^2$, $R^3$, $R^4$, $W_1$ and $W_2$ are all hydrogen.

When X is CONHOH, $R^1$, $R^2$, $R^3$ and $R^4$ are all hydrogen. When X is lower alkoxycarbonyl, $R^4$ is hydrogen, chlorine, carbamoyl, lower alkyl or —$CH_2CH_2$-$R^{7a}$ (wherein $R^{7a}$ is bromine or di-lower alkylamino).

When X is aminomethyl, $R^1$, $R^2$ and $R^3$ are hydrogen, and when $W_1$ and $W_2$ are combined together to represent oxygen, $R^4$ is hydrogen or amino and when $W_1$ and $W_2$ are hydrogen, $R^4$ is hydrogen. When X and Y are combined together to represent, aas —X—Y—, —O—, —$CH_2$—O—, —$CH_2$—O—CO—O—, —$CH_2$—O—C-S—O—, —$CH_2$—$NR^{13a}$—CO—O— (wherein the $R^{13a}$ representation is the same as the above $R^{13}$ representation excluding hydrogen and lower alkyl), —$CH_2$—NH—CS≤O—, —$CH_2$—O—SO—O— or —$CH_2$—N=$\underset{|}{C}$—O—,
                $R^{14}$ $R^1$, $R^2$, $R^3$, $R^4$, $W_1$ and $W_2$ are all hydrogen. When X and Y are combined together to represent, as —X—Y—, —$CH_2$—$NR^{13b}$—CO—O— (wherein $R^{13b}$ is hydrogen or lower alkyl), $R^1$, $R^2$, $R^3$ and $R^4$ are all hydrogen. When $R^1$ is methyl, hydroxy, hydroxymethyl, lower alkoxy, bromine, chlorine or —$NR^5R^6$, $R^2$ and $R^4$ are hydrogen. When $R^2$ is amino, $R^1$ and $R^4$ are hydrogen. Compounds wherein $R^1$, $R^2$, $R^3$, $R^4$, $W_1$ and $W_2$ are hydrogen, X is methoxycarbonyl and Y is hydroxy are excluded.

The compounds represented by general formula (I) are hereinafter referred to as Compound (I). Compounds represented by formulae with other numbers are referred to similarly.

In the definitions of the groups in formula (I), the lower alkyl moiety in the lower alkoxy, the lower alkylaminocarbonyl, the lower alkyl, the di-lower alkylamino, the lower alkoxycarbonyl, the hydroxy-substituted lower alkylamino, the lower alkylthio, the lower alkylsulfenyl, the chlorine-substituted lower alkyl, the carboxylic acid-substituted lower alkyl and the lower alkoxycarbonyl-substituted lower alkyl includes a straight chain or branched alkyl having 1 to 5 carbon atoms, for example, methyl, ethyl, n-propyl, i-propyl, n-butyl and n-pentyl.

As the hydroxy-substituted lower alkylamino in the definition of $R^7$, 2-hydroxyethylamino may be mentioned. As the hydroxy-substituted lower alkyl in the definitions of $R^8$ and $R^9$, 2-hydroxyethyl may be mentioned. In the definitions of $R^{10}$ and $R^{11}$, the chlorine-substituted lower alkyl includes 2-chloroethyl. In the definitions of $R^{10}$ and $R^{11}$, the carboxylic acid-substituted lower alkyl includes hydroxycarbonylmethyl. In the definitions of $R^{10}$ and $R^{11}$, the lower alkoxycarbonyl-substituted lower alkyl includes lower alkoxycarbonylmethyl. In the definitions of $R^{10}$ and $R^{11}$, the dihydroxy-substituted lower alkyl includes 2,3-dihydroxypropane.

In the definitions of $R^{10}$ and $R^{11}$, the α-amino acid includes glycine, alanine, valine, proline, etc. in L-form, D-form and racemic modification.

In cases where Compound (I) is aan acidic compound, base addition salts thereof can be formed, and in cases where Compound (I) is a basic compound, acid addition salts thereof can be formed. The base addition salts of Compound (I) includes ammonium salts; alkali metal salts such as lithium, sodium and potssium salts; alkaline earth metal salts such as calcium and magnesium salts; salts with organic bases such as triethylamine, morpholine, piperidine and dicyclohexylamine; and salts with basic amino acids such as arginine and lysine. The acid addition salts of Compound (I) include hydrochloride, hydrobromide, sulfate, nitrate, formate, acetate, benzoate, maleate, fumarate, succinate, tartrate, citrate, oxalate, methanesulfonate, toluenesulfonate, aspartate, glutamate, etc. Non-toxic and pharmacologically acceptable salts, for example, the base addition salts and acid addition salts mentioned above are preferred, but other salts are also useful in isolating and purifying the product.

In Compound (I), the two carbon atoms to which $CH_3$ and X are bound are asymmetric carbons. The compounds in accordance with the present invention are obtained from optically active K-252 and KT-5556 through reactions which do not alter steric nature and all of them are optically active compounds having the same steric configuration as K-252 and KT-5556.

The process for producing Compound (I) is described below. Compound (I) can be produced by the following reaction steps.

Me, Et, Pr, Bu, Ph, Ac, Bzl, Py and Ts in the structural formulae, tables, etc. refer to methyl, ethyl, propyl, butyl, phenyl, acetyl, benzyl, pyridyl and toluenesulfonyl groups, respectively.

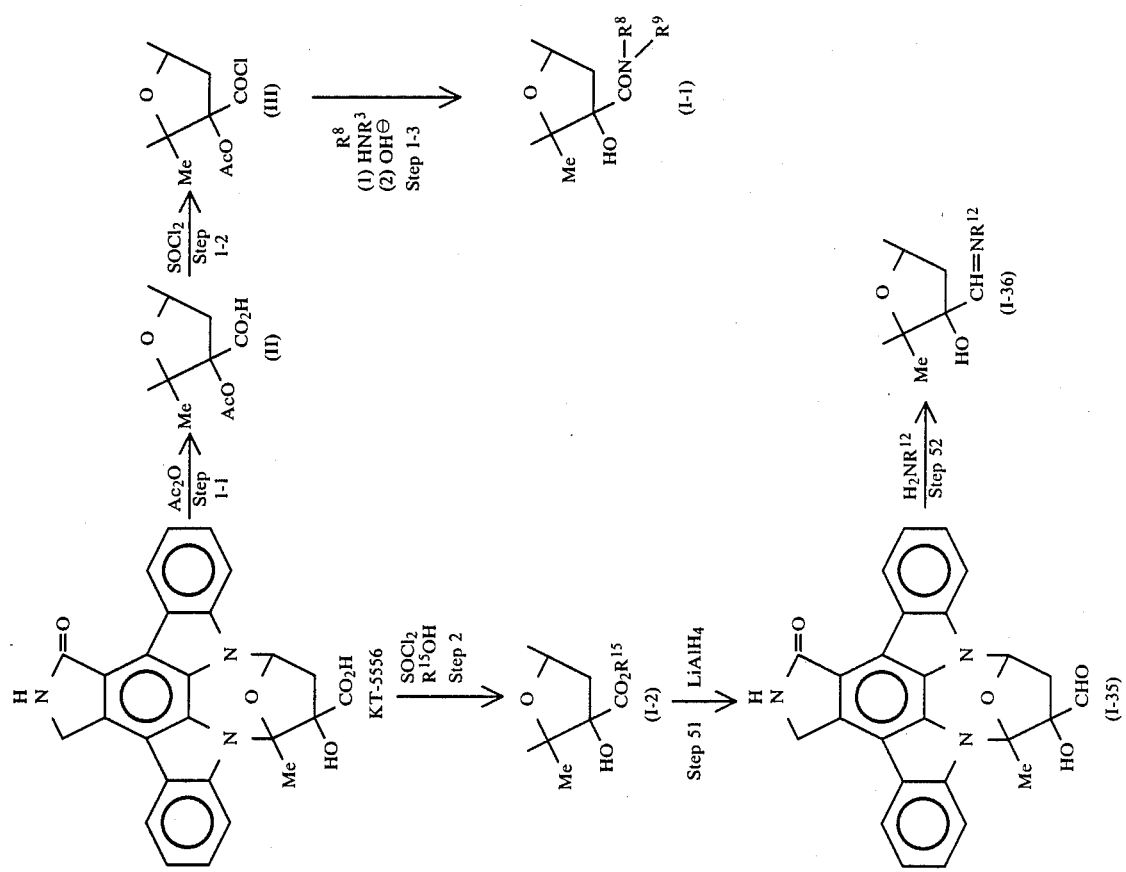

-continued
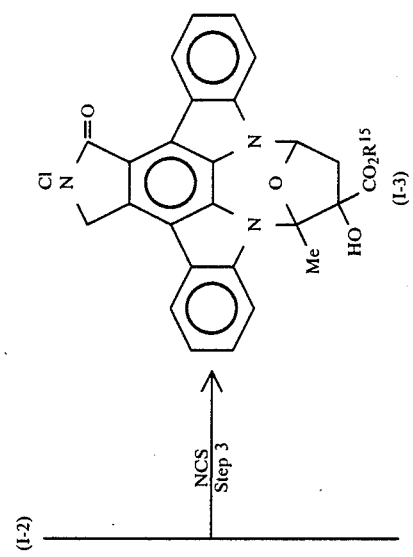
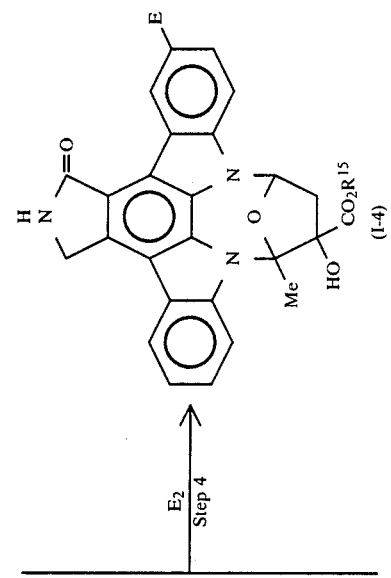

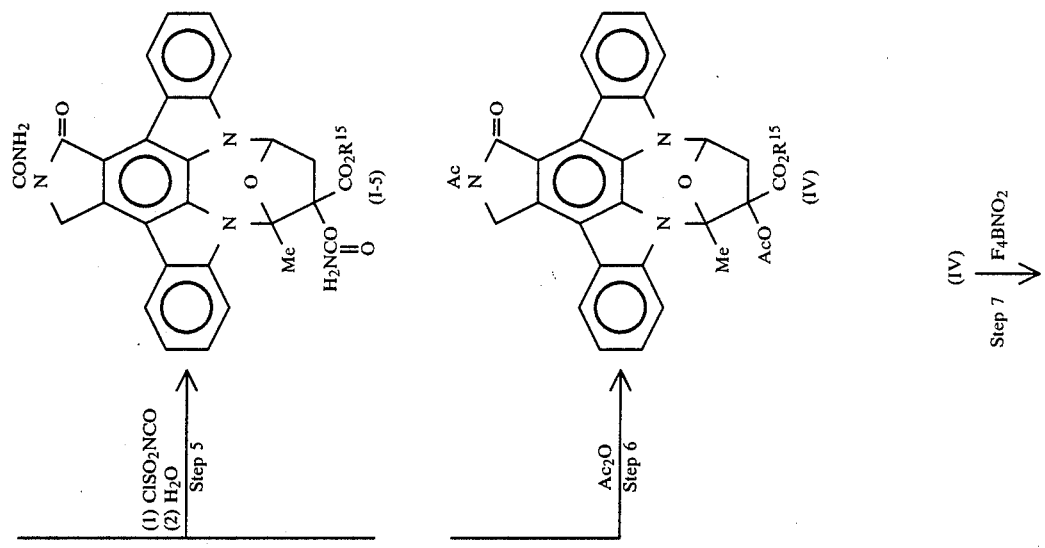

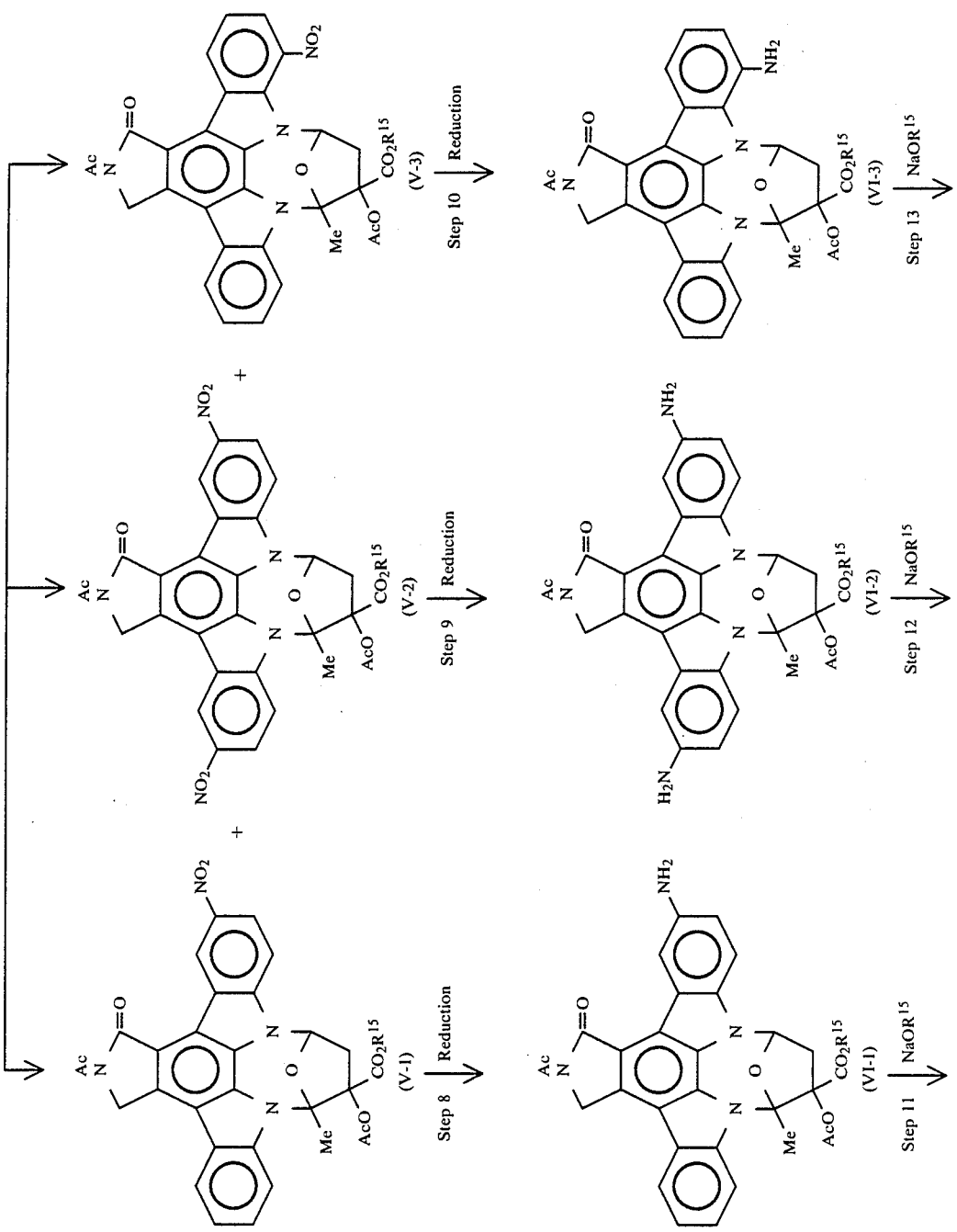

-continued
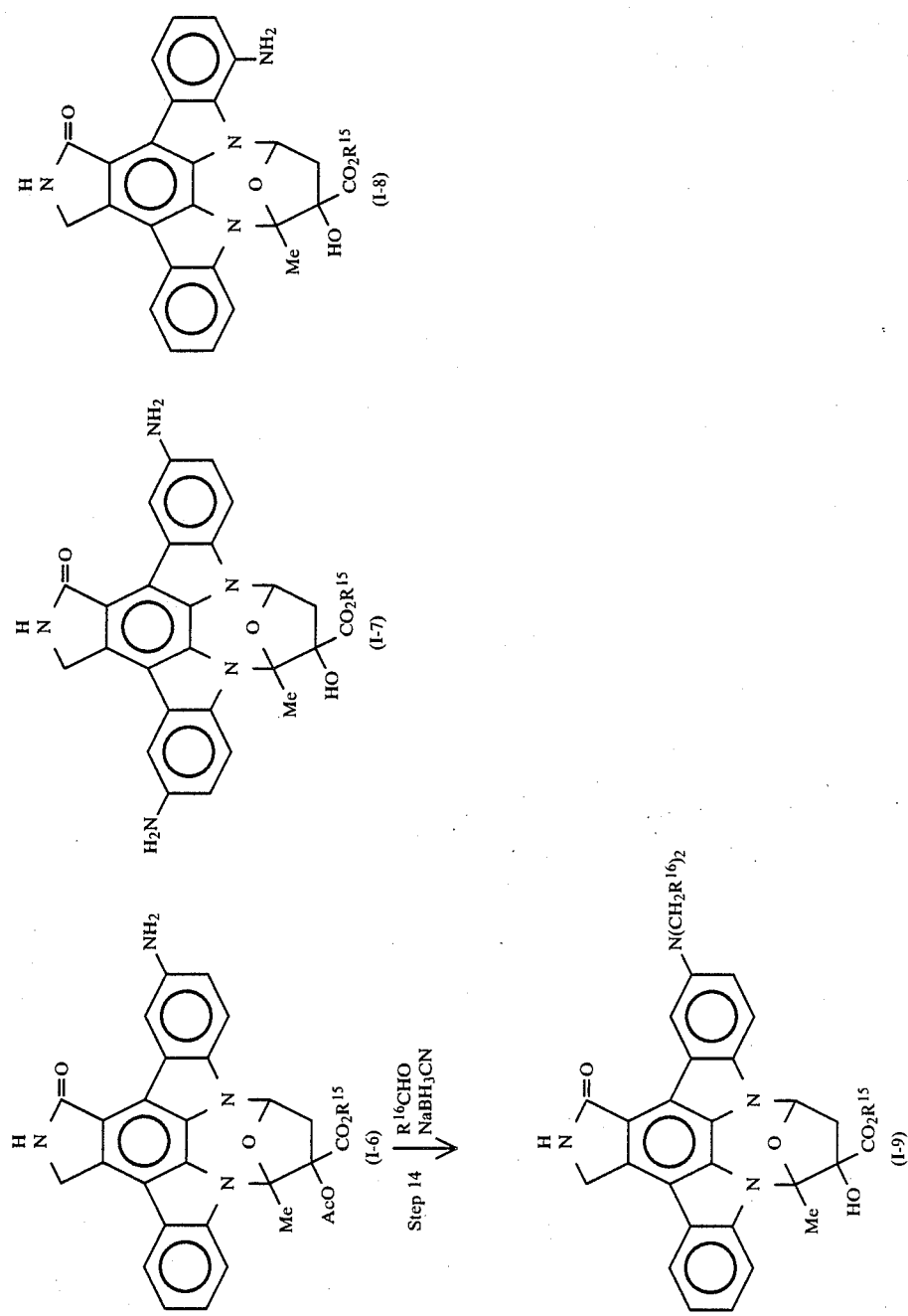

-continued
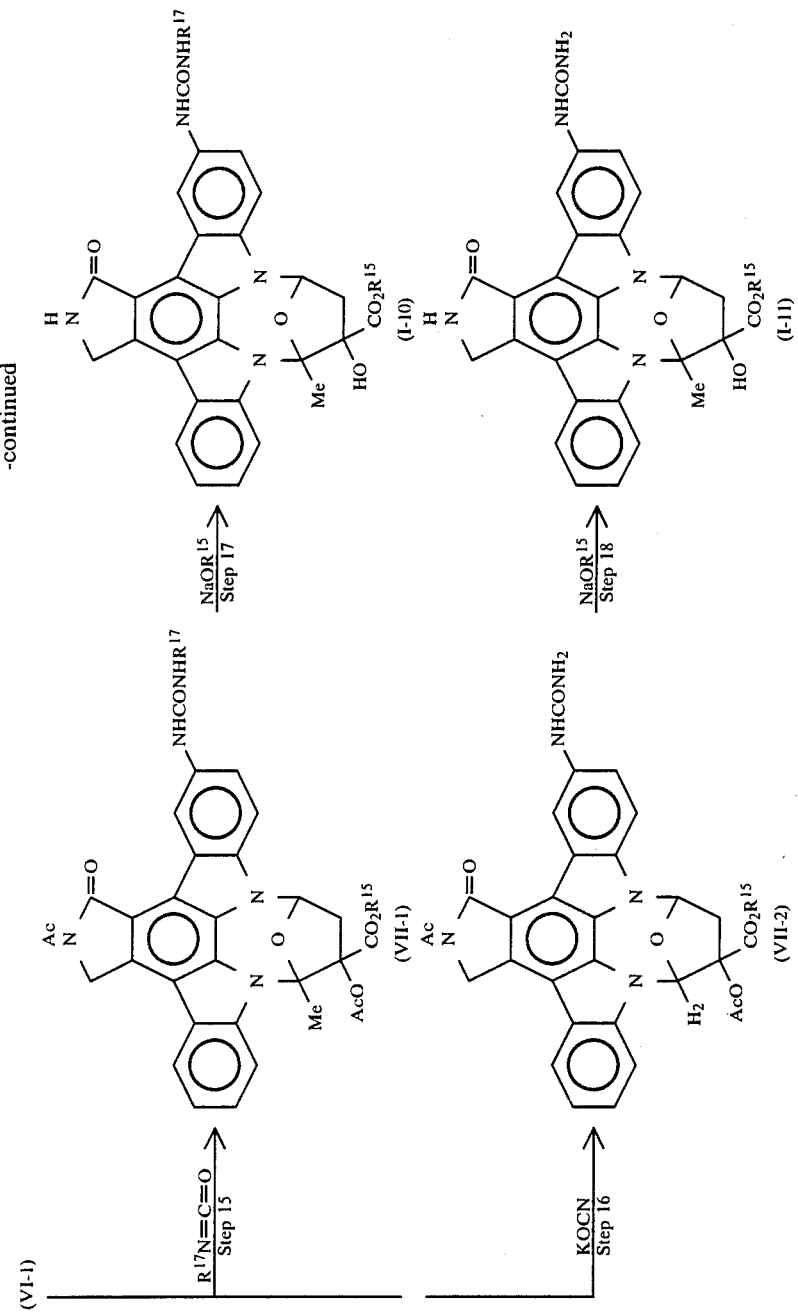

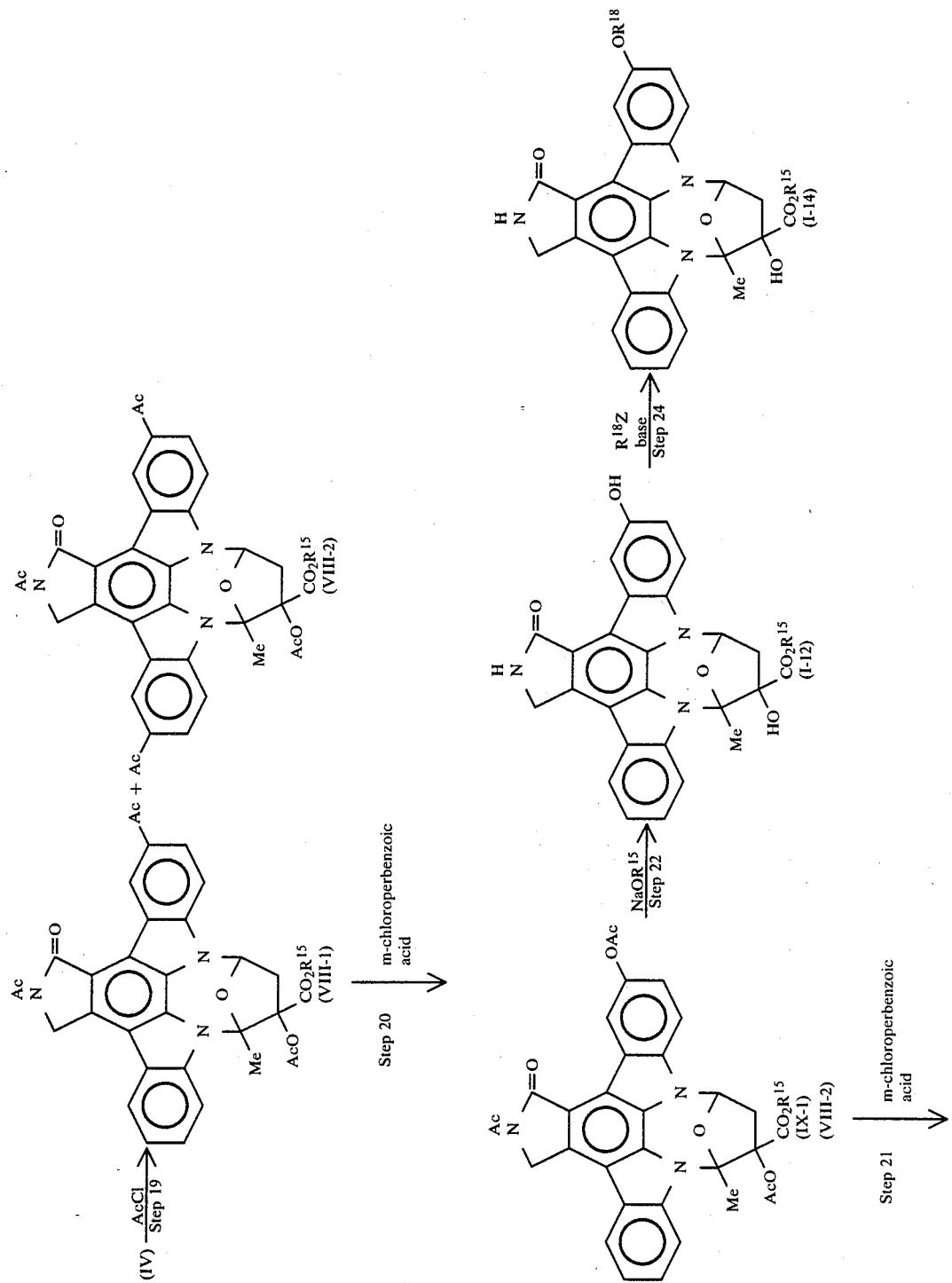

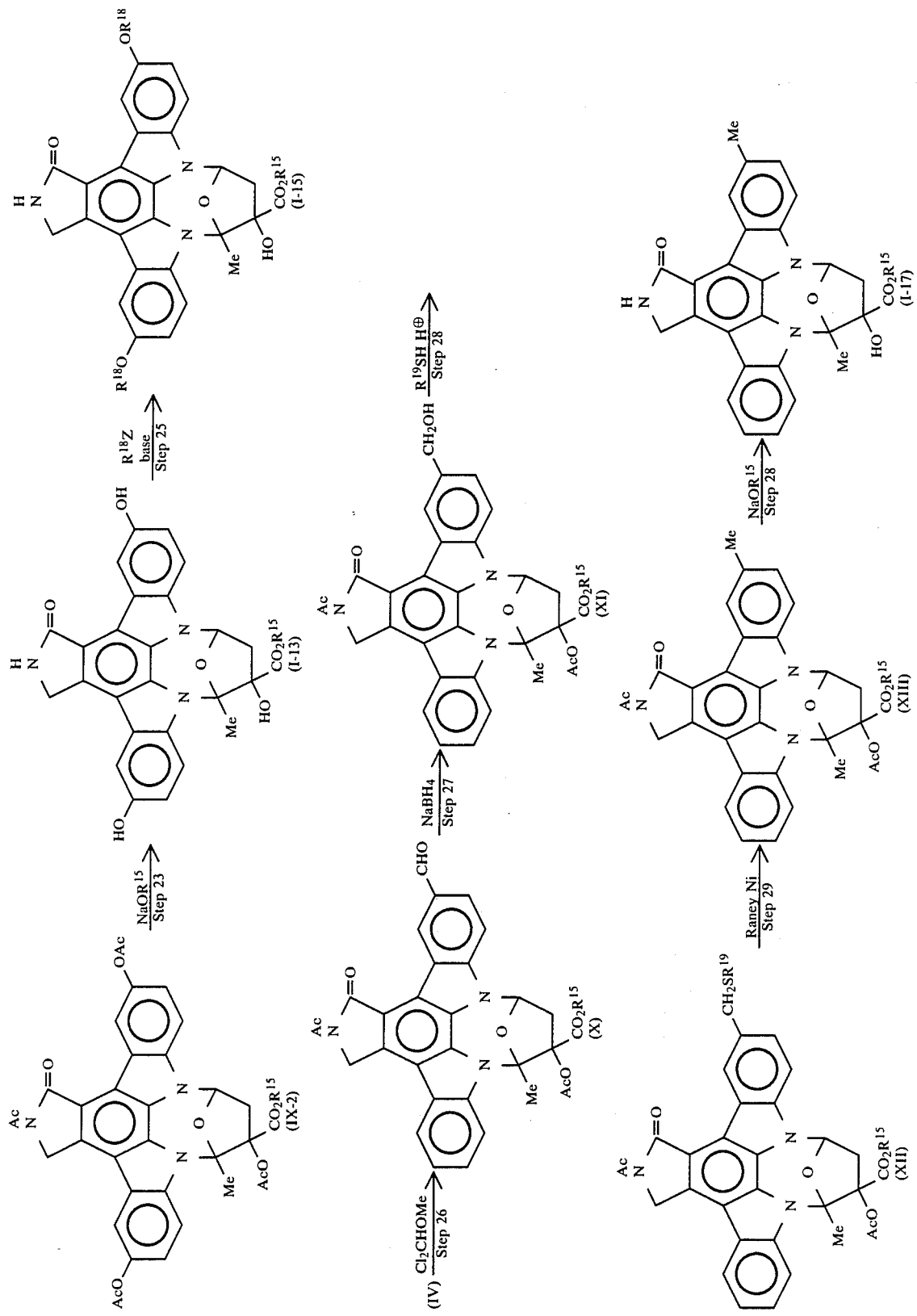

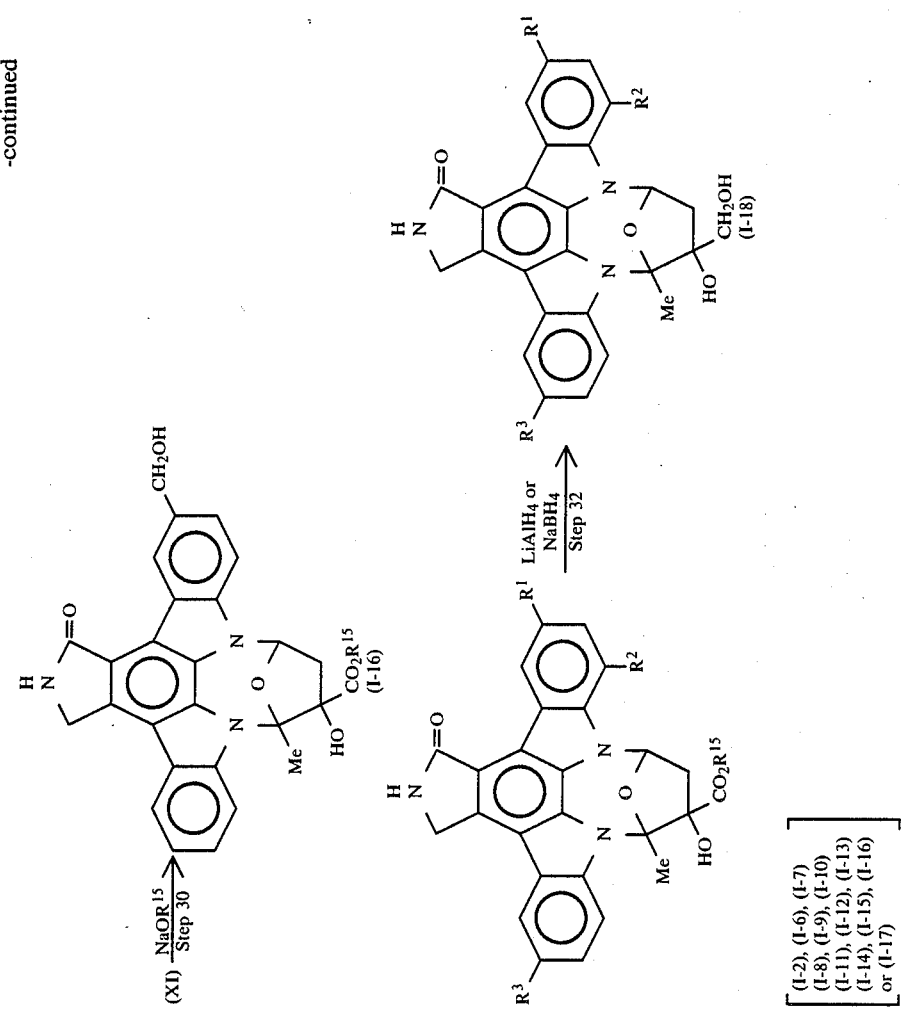

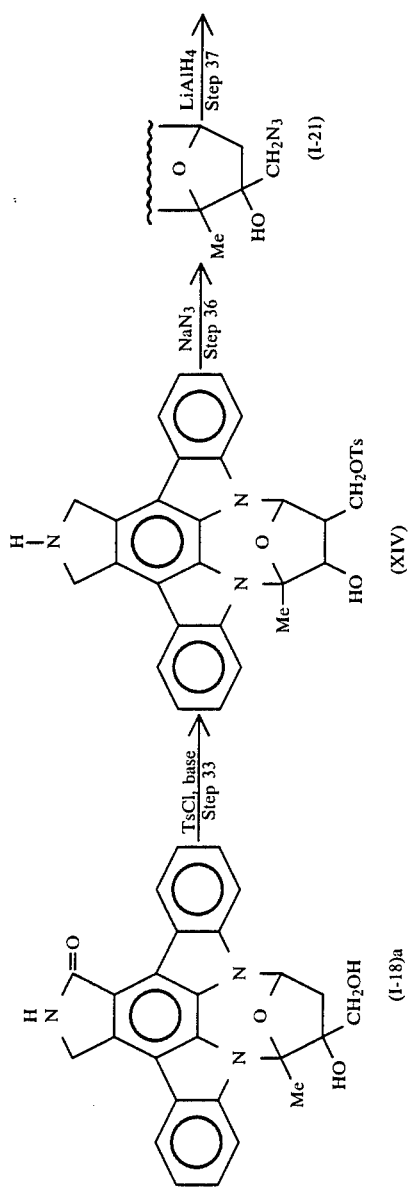
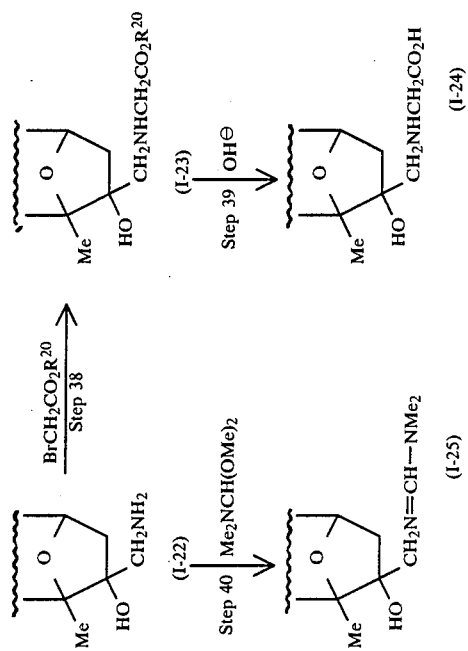

-continued
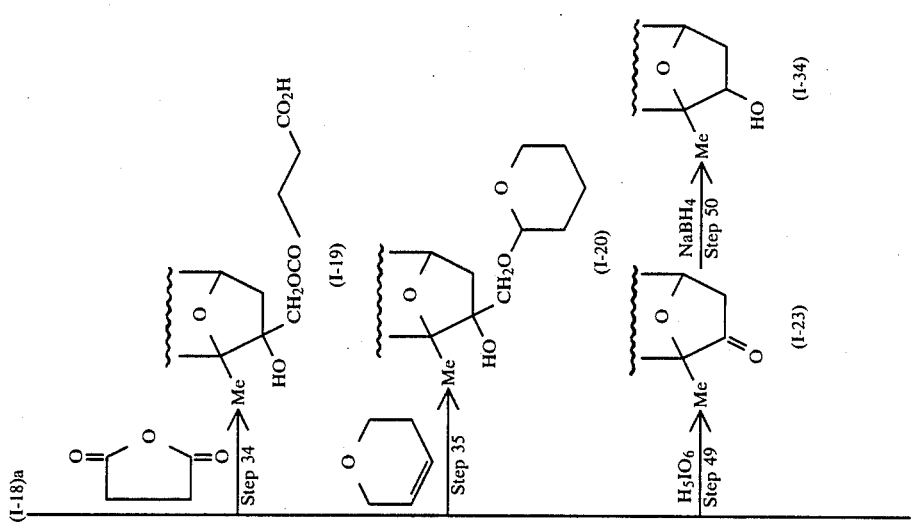

-continued
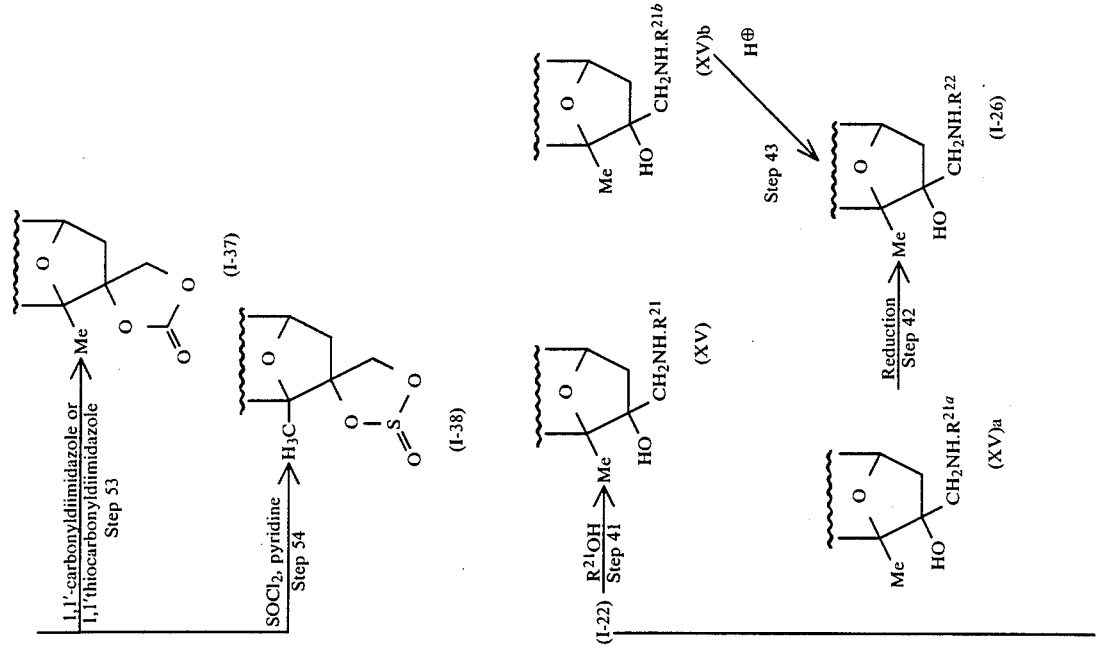

-continued
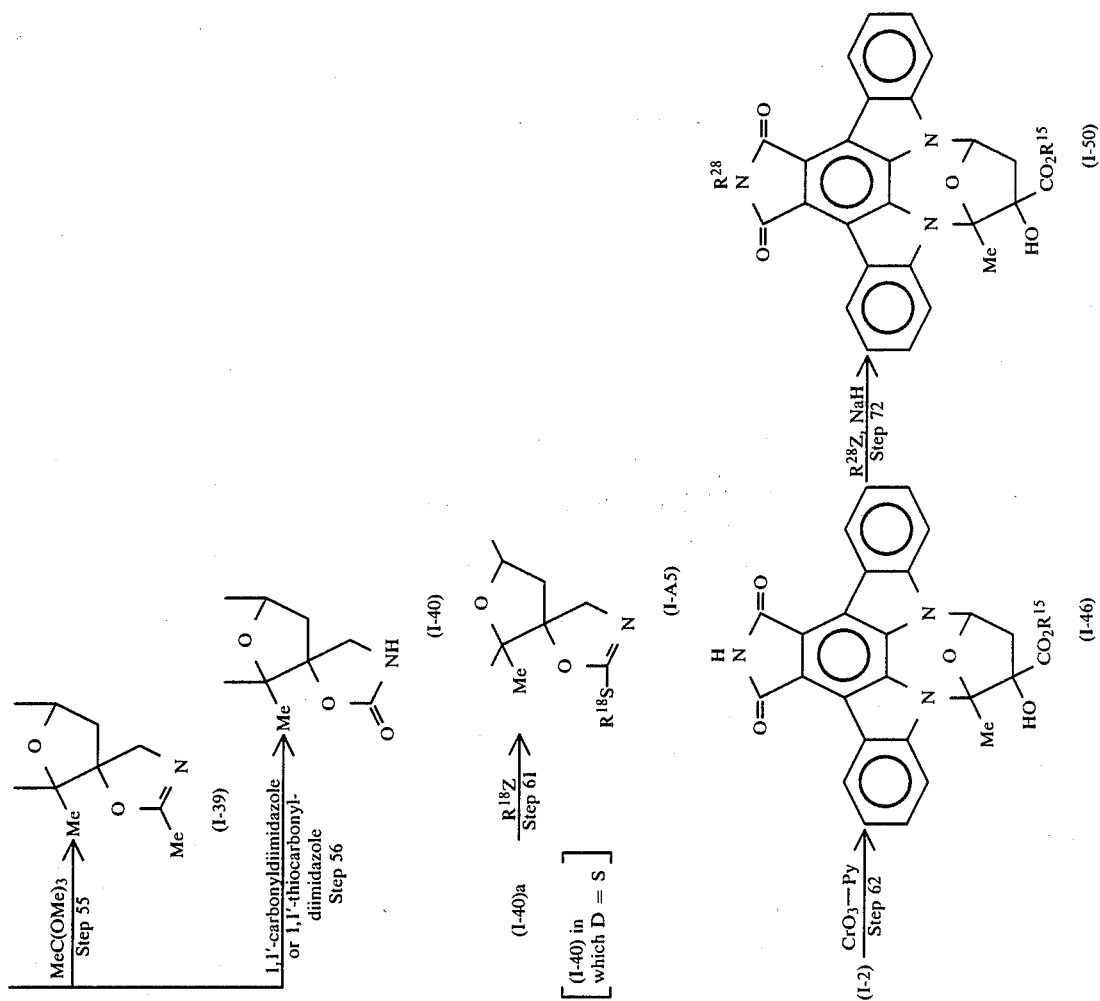

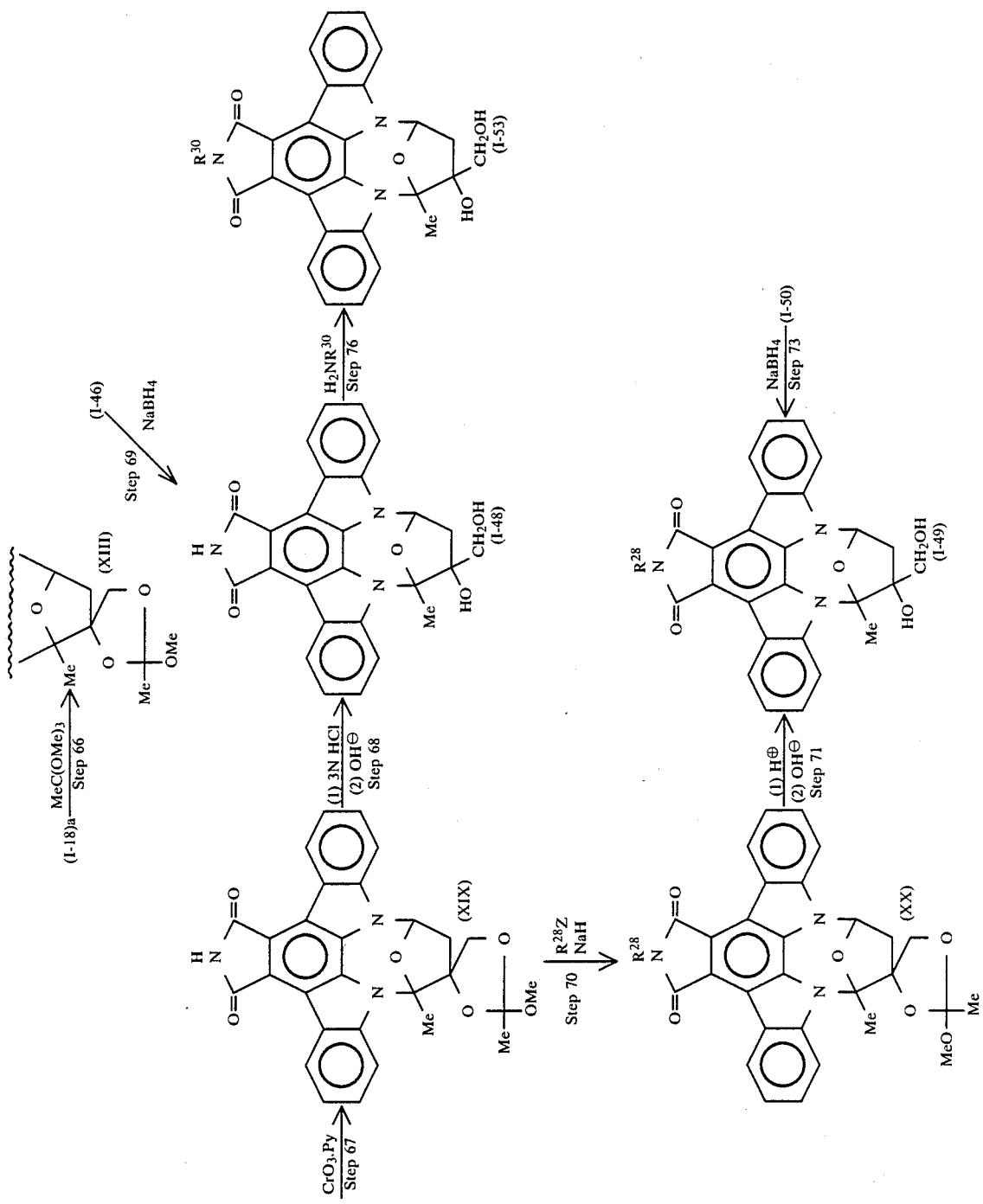

-continued
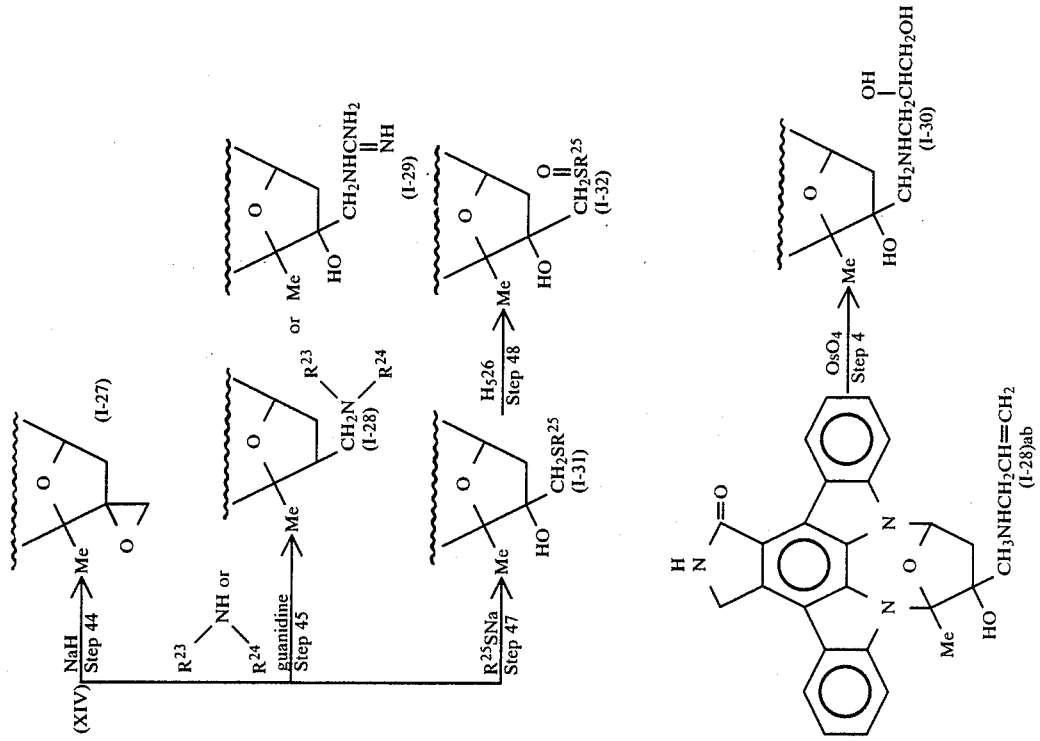

-continued
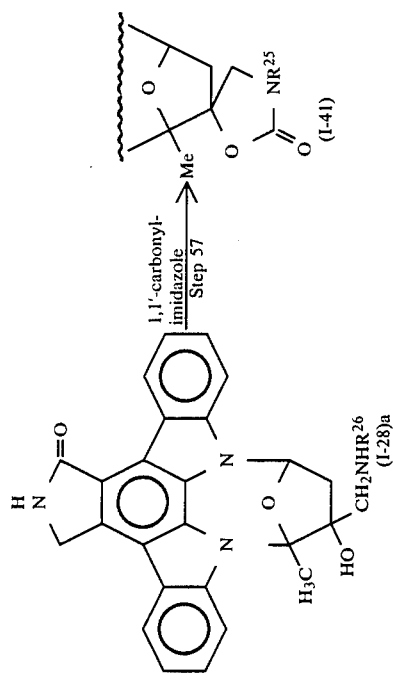
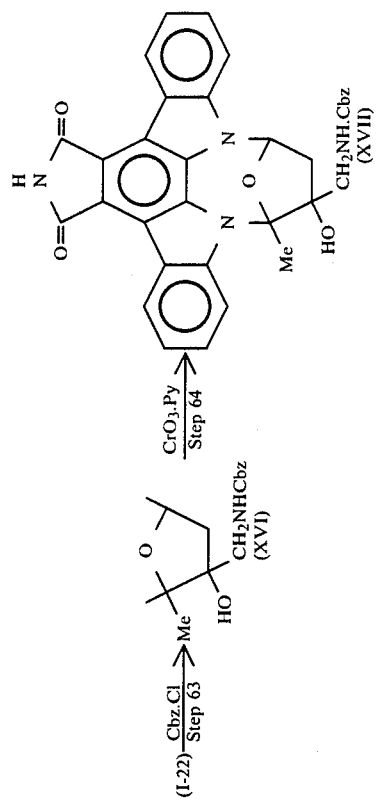

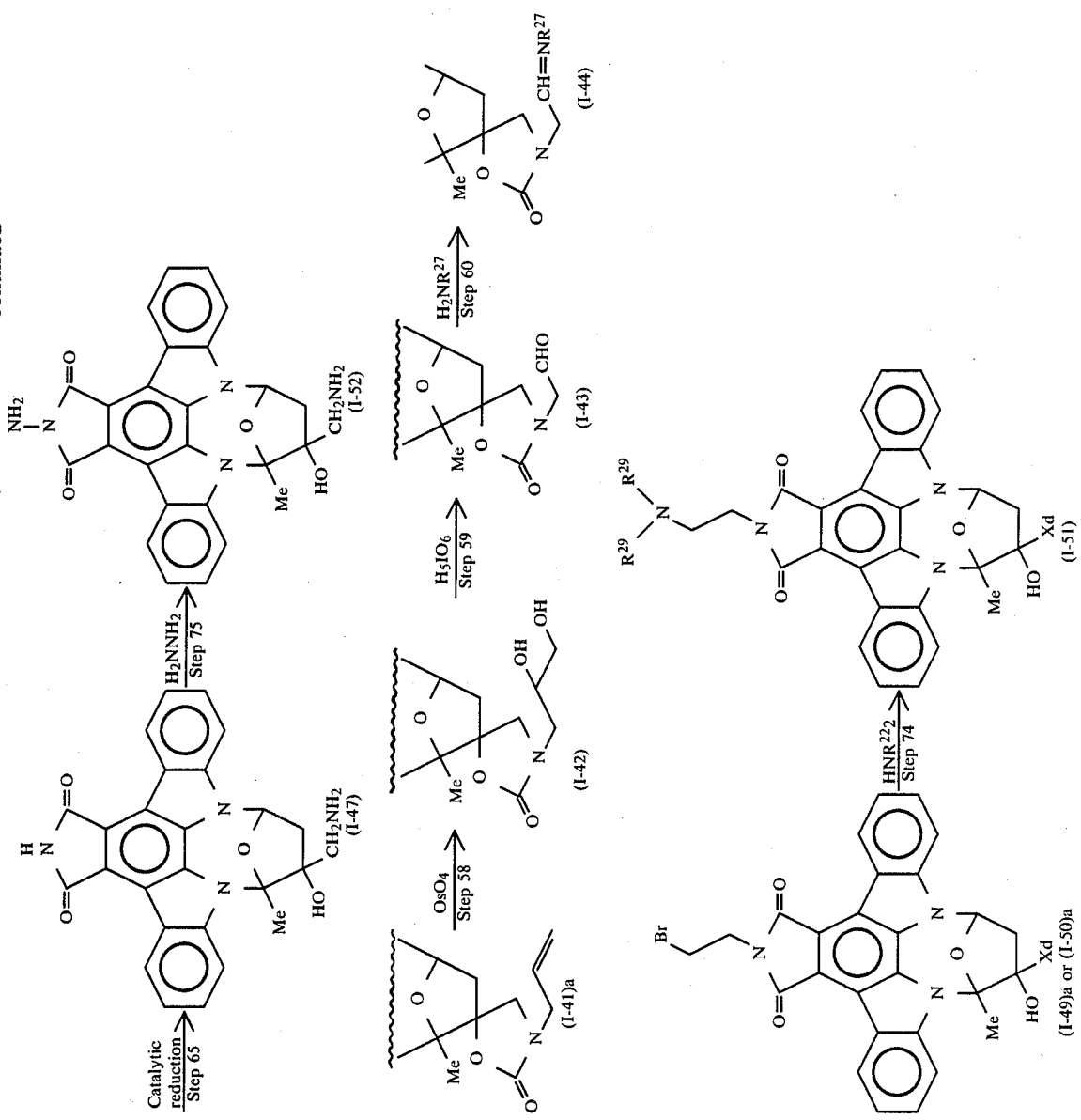

-continued
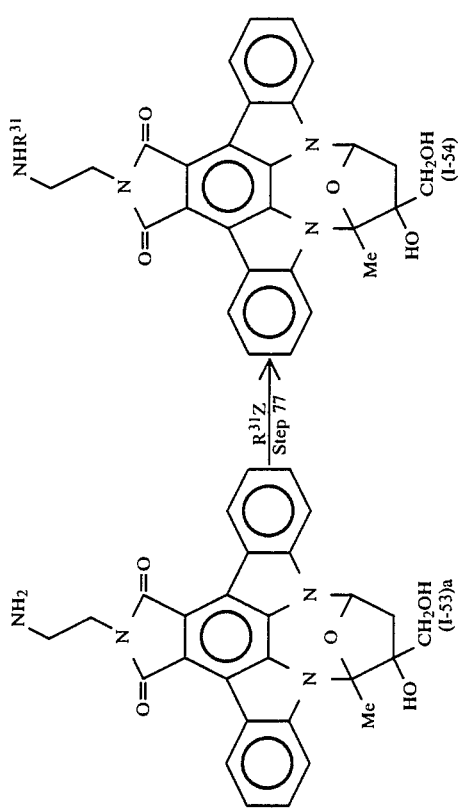
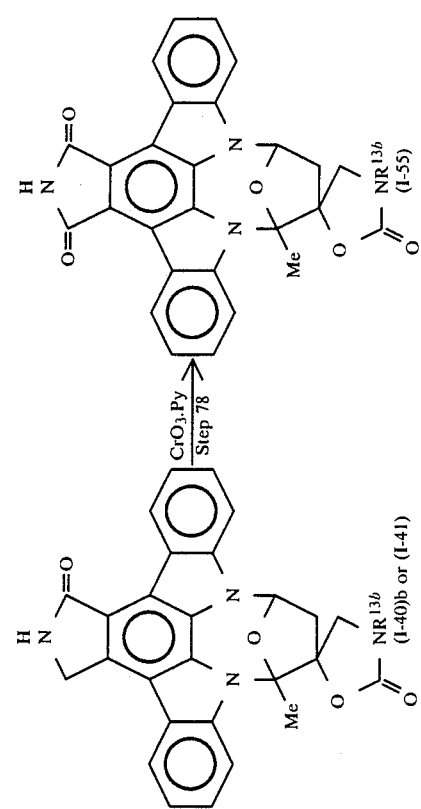

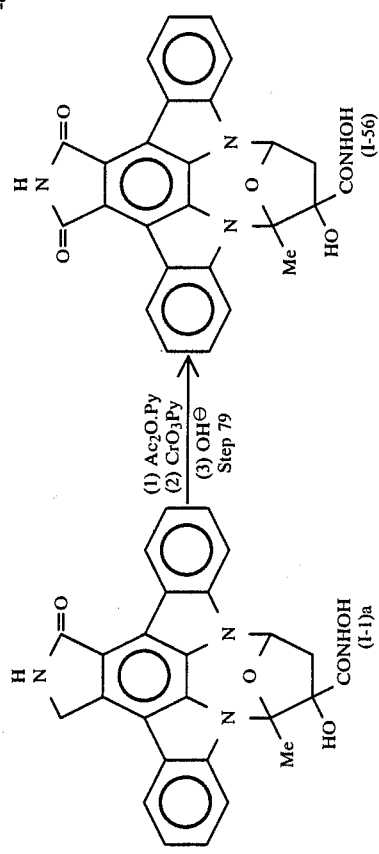

In the above formulae, $R^1$, $R^2$, $R^3$, $R^8$, $R^9$, $R^{12}$, $R^{13}$ and B have the same significance as described above. $R^{15}$, $R^{17}$, $R^{18}$, $R^{19}$, $R^{20}$, $R^{25}$ and $R^{29}$ are lower alkyl and $R^{16}$ is hydrogen or lower alkyl. $R^{21}$ is a residue of an α-amino acid having the amino group protected with t-butoxycarbonyl or benzyloxycarbonyl in which the hydroxy of the carboxylic acid is removed, $R^{21a}$ is a residue of an α-amino acid having the amino group protected with benzyloxycarbonyl in which the hydroxy of the carboxylic acid is removed; $R^{21b}$ is a residue of an α-amino acid having the amino group protected with t-butoxycarbonyl in which the hydroxy of the carboxylic acid is removed; and $R^{22}$ is a residue of an α-amino acid in which the hydroxy of the carboxylic acid is removed.

One of $R^{23}$ and $R^{24}$ is hydrogen and the other is lower alkyl or allyl; or both are lower alkyl or chlorine-substituted lower alkyl; or $R^{23}$ and $R^{24}$ are combined together to represent $-CH_2CH_2-B-CH_2CH_2-$.

D is oxygen or sulfur. $R^{26}$ is lower alkyl or allyl. $R^{27}$ is guanidino. $R^{28}$ is lower alkyl or bromine-substituted lower alkyl. $R^{30}$ is amino, amino-substituted lower alkyl or hydroxy-substituted lower alkyl. $R^{31}$ is hydroxy-substituted lower alkylamino. Xd is hydroxymethyl or lower alkoxycarbonyl. Z is halogen such as chlorine, bromine or iodine. E is chlorine or bromine. Compounds of formula Nos. (I-1), (I-2), . . . are included in Compound (I). Compounds of compound Nos. with suffixes a and b in the compound Nos. are inclined in the compounds of the same number accompanied by no suffix and compounds with ab is are included in compounds with a. For example, (I-1)a and (I-28)ab are included in (I-1) and (I-28)a, respectively.

Each step is described below.

Step 1

Compound (II) can be obtained by reaction of KT-5556 with acetic anhydride in a suitable solvent in the presence of a base. As the base, pyridine, N,N-dimethylaminopyridine, triethylamine, etc. can be used. Acetic anhydride and the base are usually used in an amount of 1.1 to 2 equivalents based on KT-5556. As the reaction solvent, chloroform, dichloromethane and the like are used. The reaction is usually carried out at 0° C. to room temperature and completed in 15 minutes to several hours (Step 1-1).

Compound (II) is heated under reflux in thionyl chloride to give acid chloride of Compound (II), i.e., Compound (III) (Step 1-2). Compound (III) is made to react with an amine

to obtain an amide compound. The amine component is generally used in an equivalent or excess amount, usually in an amount of 1 to 5 equivalents, based on Compound (III). As the reaction solvent, anhydrous chloroform, dichloromethane, and the like can be used. The reaction is usually carried out at room temperature and completed in several hours.

Then, the acetoxy group of the amide compound obtained above is hydrolyzed with an alkali, whereby Compound (I-1) can be obtained. The reaction is carried out in a solvent mixture obtained by adding water to alcohols such as methanol and ethanol, such sodium hydroxide or potassium hydroxide in an amount of 1.5 to 3 equivalents based on the amide compound. The reaction is usually carried out at room temperature and completed in several hours (Step 1-3).

Step 2

Alcohol $R_{15}OH$ and an excess of thionyl chloride are added to KT-5556, and the mixture is heated under reflux to give compound (I-2). Thionyl chloride is usually used in an amount of about one tenth (volume ratio) of the amount of the alcohol used also as the solvent. The reaction is carried out in the range of 80° to 100° C., and almost completed in several hours to one day.

Step 3

Compound (I-2) and a suitable chlorinating agent, for example, N-chlorosuccinimide (NCS) are subjected to reaction in a solvent inert to the reaction to give Compound (I-3). The chlorinating agent is usually used in an equivalent amount based on Compound (I-2). The inert solvent includes chloroform, dichloromethane, and the like. The reaction is carried out with heating under reflux, and usually completed in several hours.

Step 4

Compound (I-2) and halogen in an amount of 1 to 2 equivalents based on the compound are stirred in an inert solvent at room temperature for one day to give Compound (I-4). The inert solvent includes pyridine, chloroform, and the like.

Step 5

Compound (I-2) and a suitable carbamoylating agent, for example, chlorosulfonyl isocyanate are stirred in an inert solvent, for example, tetrahydrofuran (hereinafter referred to as THF) under ice cooling for 1 to 3 hours, and then water is added thereto. The mixture is stirred under heating at 70° to 80° C. for 0.5 to 1 hour to give Compound (I-5). The carbamoylating agent is used in an amount of 5 to 10 equivalents and water is used in an large excess amount based on Compound (I-2).

Step 6

Compound (I-2) is allowed to react with acetic anhydride in the presence of a base to give Compound (IV). The base includes pyridine, triethylamine, etc. Acetic anhydride is usually used in an amount of 5 to 10 equivalents based on Compound (I-2). The reaction is usually carried out using pyridine as the solvent at room temperature and completed in 1 to several hours.

Step 7

Compounds (V-1), (V-2) and (V-3) are obtained by reaction of Compound (IV) with a suitable nitrating agent, for example, nitronium tetrafluoroborte in a solvent inert to the reaction. The nitrating agent is usually used in an amount of 1 to 1.1 equivalents based on Compound (IV). The inert solvent includes sulfolane, acetonitrile, etc. The reaction is carried out at room temperature to 80° C. and completed usually in 1 to 2 hours.

Step 8

Compound (VI-1) is obtined by reducing Compound (V-1) in a solvent inert to the reaction according to a suitable reduction method, for example, catalytic reduction. The catalyst includes 5 to 10% palladium carbon, etc. and is usually used in an amount of 0.1 to 0.5 times that of the weight of Compound (V-1). The inert solvent includes THF, dimethylformamide (hereinafter referred to as DMF), etc. The reaction is usually carried out at room temperature and completed in several hours to one day.

Step 9

The reaction is carried out in a similar manner as in Step 8.

Step 10

The reaction is carried out in a similar manner as in Step 8.

Step 11

Compound (I-6) is obtained by reaction of Compound (VI-1) with sodium lower alkoxide NaOR$^{15}$ in an inert solvent, followed by acidification with hydrochloric acid, etc. NaOR$^{15}$ is usually used in an amount of 5 to 7 equivalents based on Compound (VI-1). The inert solvent includes dichloromethane, THF, etc. The reaction is carried out at 0° C. to room temperature and usually completed in 3 to 30 minutes.

Step 12

The reaction is carried out in a similar manner as in Step 11.

Step 13

The reaction is carried out in a similar manner as in Step 11.

Step 14

Compound (I-9) is obtained by reaction of Compound (I-6) with R$^{16}$CHO and a suitable reducing agent, for example, sodium cyanoborohydride in a solvent inert to the reaction. Usually, R$^{16}$CHO is used in a large excess amount and the reducing agent is used in an amount of 1 to 2 equivalents based on Compound (I-6). As the inert solvent, a 1:1 solvent mixture of THF and a suitable lower alkanol, for example, methanol, etc. can be used. The reaction is usually carried out at room temperature and completed in 0.5 to one hour.

Step 15

Compound (VII-1) is obtained by reaction of Compound (VI-1) with lower alkyl isocyanate R$^{17}$N=C=O in a solvent inert to the reaction in the presence of a base. The base includes triethylamine, etc. Usually, R$^{17}$N=C=O is used in an amount of 2 to 3 equivalents and the base is used in an amount of 1 to 2 equivalents based on Compound (VI-1). The inert solvent includes dichloromethane, chloroform, etc. The reaction is usually carried out at room temperature and completed in 1 to 5 hours.

Step 16

Compound (VI-1) is allowed to react with potassium cyanate usually in an amount of about 5 equivalents based on the compound in a solvent mixture of THF, acetic acid and water (10:1:1) to give Compound (VII-2). The reaction is usually carried out at room temperature and completed in one hour.

Steps 17 and 18

The reactions are carried out in a similar manner as in Step 11.

Step 19

Compounds (VIII-1) and (VIII-2) are obtained by reaction of Compound (IV) with acetyl chloride in a solvent inert to the reaction in the presence of an appropriate Lewis acid, for example, aluminum chloride. Usually, acetyl chloride is used in an amount of 1 equivalent and Lewis acid in an amount of 5 equivalents based on Compound (IV). The inert solvent includes dichloromethane, chloroform, etc. The reaction is usually carried out under ice cooling and completed in several hours.

Step 20

Compound (IX-1) is obtained by reaction of Compound (VIII-1) with an appropriate oxidizing agent, for example, m-chloroperbenzoic acid in a solvent inert to the reaction, which is usually chloroform. The oxidizing agent is usually used in an amount of 5 equivalents based on Compound (VIII-1) twice at an interval of one hour. The reaction is usually carried out with heating under reflux and completed in several hours.

Step 21

The reaction is carried out in a similar manner as in Step 20.

Steps 22 and 23

The reactions are carried out in a similar manner as in Step 11.

Step 24

Compound (I-14) is obtained by reaction of Compound (I-12) with lower alkyl halide R$^{18}$Z in a solvent inert to the reaction in the presence of a base. As the lower alkyl halide, iodides and bromides which are highly reactive are preferred. The base includes sodium hydride, potassium t-butoxide, etc. The lower alkyl halide and the base are usually used in an equivalent amount based on Compound (I-12). The inert solvent includes DMF, THF, etc. The reaction is usually carried out at 0° C. to ordinary temperature and completed in 20 minutes to one hour.

Step 25

The reaction is carried out in a similar manner as in Step 24.

Step 26

Compound (X) is obtained by reaction of Compound (IV) with dichloromethyl methyl ether in a solvent inert to the reaction in the presence of an appropriate Lewis acid, for example, titanium tetrachloride. Usually, dichloromethyl methyl ether is used in an amount of 1 to 2 equivalents and titanium tetrachloride in an amount of 5 to 7 equivalents based on Compound (IV). As the inert solvent, dichloromethane is usually used. The reaction is usually carried out at room temperature and completed in several hours.

Step 27

Compound (XI) is obtained by reaction of Compound (X) with an appropriate reducing agent, for example, sodium borohydride in a solvent inert to the reaction. The reducing agent is usually used in an amount of 2 to 3 equivalents based on Compound (X). As the inert solvent, a solvent mixture of chloroform-methanol (1:1) is usually used. The reaction is usually carried out under ice cooling and completed in 0.5 to one hour.

Step 28

Compound (XII) is obtained by reaction of Compound (XI) with lower alkylthiol R$^{19}$SH in a solvent inert to the reaction in the presence of an appropriate acid catalyst, for example, camphor sulfonic acid catalyst. Usually, R$^{19}$SH is used in an amount of 5 to 10 equivalents and the acid is used in an equivalent amount based on Compound (XI). The inert solvent includes chloroform, etc. The reaction is usually carried out at room temperature and completed in 2 to 3 hours.

Step 29

Compound (XIII) is obtained by heating Compound (XII) under reflux with Raney nickel in an amount of 0.1 to 0.5 times the weight of Compound (XII) in ethyl acetate for 5 to 7 hours.

Steps 30 and 31

The reactions are carried out in a similar manner as in Step 11.

Step 32

Compound (I-18) can be obtained by reducing the ester moiety of Compound (I-2), (I-6), (I-7), (I-8), (I-9), (I-10), (I-11), (I-12), (I-13), (I-14), (I-15), (I-16) or (I-17). As the reducing agent, lithium aluminum hydride (1 to 2 molar equivalents based on the compounds mentioned above) and sodium borohydride (5 equivalents based on the compounds mentioned above) are useful. The reaction is carried out, in the case of lithium aluminum hydride, in a solvent such as THF or dioxane, and in the case of sodium borohydride, in a solvent mixture of THF-MeOH, usually at 0° C. to room temperature and completed in several hours.

Step 33

Tosylate (XIV) can be obtained by reaction of Compound (I-18)a with p-toluenesulfonyl chloride in the presence of a base. As the base, triethylamine, pyridine, N,N-dimethylaminopyridine, sodium hydride, etc. are used, and as the solvent, THF, dioxane, chloroform, etc. are used. p-Toluenesulfonyl chloride and the base are usually used in an amount of 2 to 3 equivalents based on Compound (I-18)a. The reaction is usually carried out at 0° C. to room temperature and almost completed in several hours to one day.

Step 34

Compound (I-19) is obtained by reaction of Compound (I-18)a with succinic anhydride in an inert solvent in the presence of an appropriate base, for example, triethylamine at 80° to 110° C. for 2 hours.

Succinic anhydride is used in an amount of 1 to 2 equivalents and the base in an amount of 1 to 2 equivalents based on Compound (I-18)a. The inert solvent includes THF, DMF, etc.

Step 35

Compound (I-20) is obtained by heating Compound (I-18)a under reflux with 3,4-dihydro-2H-pyran in an inert solvent for 4 hours in the presence of an appropriate acid catalyst, for example, camphor sulfonic acid catalyst. 3,4-Dihydro-2H-pyran is used in an equivalent amount and the acid in an amount of 0.1 equivalent based on the compound. The inert solvent includes chloroform, THF, etc.

Step 36

The azide (I-21) can be obtained by reaction of Compound (XIV) with sodium azide (1 to 2 equivalents). As the solvent, DMF, dimethylsulfoxide, THF, etc. are used. The reaction is usually carried out at room temperature and completed in several hours to one day.

Step 37

The amine (I-22) is obtained by reducing Compound (I-21) with lithium aluminum hydride (excess, 2 to 6 molar equivalents). As the solvent, THF, dioxane, etc. are used. The reaction is usually carried out at 0° C. to room temperature and completed in several hours.

Step 38

Compound (I-23) can be obtained by stirring Compound (I-22) and a bromoacetic acid lower alkyl ester in an inert solvent at room temperature for one day in the presence of an appropriate base, for example, 4-dimethylaminopyridine. The bromoacetic acid lower alkyl ester is used in an amount of 1 to 2 equivalents and the base in an amount of 2 equivalents based on Compound (I-22). The inert solvent includes DMF, THF, etc.

Step 39

Compound (I-24) can be obtained by adding 1N sodium hydroxide aqueous solution to Compound (I-23), stirring the mixture in a solvent mixture of THF and methanol (3:1) at room temperature for 0.5 hour, and then treating the mixture with an acid. The 1N sodium hydroxide aqueous solution is used in an amount of 3 to 5 equivalents based on Compound (I-23).

Step 40

Compound (I-25) can be obtained by stirring Compound (I-22) and N,N-dimethylformamide dimethyl acetal in an inert solvent at room temperature for 2 hours. N,N-Dimethylformamide dimethyl acetal is used in an equivalent amount based on Compound (I-22). As the inert solvent, DMF is used.

Step 41

Compound (XV) can be obtained by condensing Compound (I-22) with $R^{21}OH$ in a THF solvent using N-oxysuccinimide and dicyclohexyl carbodiimide (DCC). $R^{21}OH$, N-oxysuccinimide and DCC are used respectively in amounts of 1 to 2 equivalents, one equivalent and 1 to 2 equivalents based on Compound (I-22). The reaction is usually carried out at 0° C. to room temperature and completed in one day.

Step 42

The reaction is carried out in a similar manner as in Step 8.

Step 43

Compound (I-26) is obtained by reaction of Compound (XV)b with a large excess of trifluoroacetic acid in a chloroform solvent at room temperature for one hour.

Step 44

The epoxide (I-27) can be obtained by reaction of Compound (XIV) with an excess (usually 1 to 2 equivalents) of sodium hydride. The reaction is usually carried out in THF or dioxane at room temperature and completed in several hours.

Step 45

The substituted amino compound (I-28) or the guanidino compound (I-29) can be obtained by reaction of Compound (XIV) with an amine component, namely, amine

or guanidine in a large excess, usually in an amount of 1 to 10 equivalents. The reaction proceeds rapidly by adding a strong base such as 1,8-diazabicyclo[5,4,0]-7-undecene (DBU) in addition to the amine component which is allowed to react. In cases where the amine component used is a salt such as hydrochloride, it is necessary to add an equimolar amount of tertiary amine such as triethylamine or DBU. The reaction is carried out in DMF or THF at room temperature and completed in several hours to one day.

Step 46

Compound (I-30) can be obtained by stirring Compound (I-28)ab and an equivalent amount of osmic acid in a solvent mixture of THF and pyridine (10:1) at room temperature for 0.5 hour, adding sodium hydrogensulfite in an amount of 4.4 equivalents thereto, and then stirring the mixture at room temperature for one hour.

Step 47

Compound (I-31) can be obtained by reaction of Compound (XIV) with sodium thiolate ($R^{25}SNa$) (excess, 1.5 to 10 equivalents). The reaction is usually carried out in THF at room temperature and completed in several hours to one day.

Step 48

The sulfoxide (I-32) is obtained by oxidizing Compound (I-31) with periodic acid (1 to 1.05 equivalents). As the solvent, a solvent mixture of THF and water is used. The reaction is usually carried out in the range of 0° C. to room temperature and completed in several hours to one night.

Step 49

The oxo compound (I-33) is obtained by oxidizing Compound (I-18)a with periodic acid (1 to 1.05 equivalents). The reaction is usually carried out in a solvent mixture of methanol-THF at room temperature and completed in several hours.

Step 50

Compound (I-34) can be obtained by adding sodium borohydride in an amount of 5 equivalents to a solution of Compound (I-33) in a THF-ethanol solvent mixture and stirring the mixture at room temperature for one hour.

Step 51

Compound (I-35) is obtained by reaction of Compound (I-2) with an appropriate reducing agent, for example, lithium aluminum hydride, usually in THF. The reducing agent is usually used in an equivalent amount. The reaction is carried out under ice cooling and usually completed in one hour.

Step 52

Compound (I-36) is obtained by reaction of Compound (I-35) with $H_2NR^{12}$ usually in a solvent mixture of $THF-H_2O$ (10:1). $H_2NR^{12}$ is usually used in an amount of 5 to 10 equivalents in the form of hydrochloride, hydrobromide or sulfate. The reaction is usually carried out at room temperature and completed in several hours to one day.

Step 53

Compound (I-37) is obtained by reaction of Compound (I-18)a with 1,1'-carbonyldiimidazole or 1,1'-thiocarbonyldiimidazole in excess, usually in an amount of 1.5 to 3 equivalents. The reaction proceeds without a base, but proceeds rapidly by the addition of a tertiary amine such as triethylamine. The reaction is usually carried out in THF at room temperature and completed in several hours to one night.

Steps 54

The cyclic sulfinate (I-38) can be obtained by reaction of Compound (I-18)a with thionyl chloride in an amount of 1 to 1.5 equivalents in pyridine. The reaction is usually carried out at room temperature and completed in several hours.

Step 55

Compound (I-39) is obtained by reaction of Compound (I-22) with trimethyl orthoacetate in an amount of 1 to 1.5 equivalents in sulfolane at 100° C. for 3 hours in the presence of an appropriate acid catalyst, for example, camphor sulfonic acid catalyst (0.04 equivalent).

Step 56

The reaction is carried out in a similar manner as in Step 53.

Step 57

The reaction is caried out in a similar manner as in Step 53.

Step 58

The reaction is carried out in a similar manner as in Step 46.

Step 59

The reaction is carried out in a similar manner as in Step 49.

Step 60

The reaction is carried out in a similar manner as in Step 52.

Step 61

Compound (I-45) is obtained by reaction of Compound (I-40)a with lower alkyl halide $R^{18}Z$ usually in DMF. As $R^{18}Z$, iodides which are highly reactive are preferred. The reaction is usually carried out at room temperature and completed in several hours.

Step 62

Compound (I-46) is obtained by reaction of Compound (I-2) with an appropriate oxidizing agent, for example, Collins reagent (chromic acid dipyridine complex) in a pyridine solvent in the range of 0° C. to room temperature for one day. The oxidizing agent is used in an amount of 5 to 7 equivalents based on Compound (I-2).

Step 63

Compound (XVI) is obtained by reaction of Compound (I-22) with benzyloxycarbonyl chloride in a solvent mixture of THF-water under ice cooling for 0.5 to one hour in the presence of an appropriate base, for example, sodium hydrogencarbonate. The base is used in an amount of 5 equivalents and benzyloxycarbonyl chloride in an amount of 1 to 1.5 equivalents based on Compound (I-22).

Step 64

The reaction is carried out in a similar manner as in Step 62.

Step 65

The reaction is carried out in a similar manner as in Step 8.

Step 66

Compound (XIII) is obtained by heating Compound (I-18)a under reflux with trimethyl orthoacetate in a chloroform solvent for 10–30 minutes in the presence of an appropriate acid catalyst, for example, camphor sulfonic acid catalyst. The acid catalyst is used in an amount of 0.1 equivalent and trimethyl orthoacetate in an amount of 2 equivalents based on Compound (I-18)a.

Step 67

The reaction is carried out in a similar manner as in Step 62.

Step 68

Compound (I-48) can be obtained by treating Compound (XIX) with a large excess of 3N hydrochloric acid aqueous solution in a chloroform-methanol solvent mixture at room temperature for 1 to 2 hours and then treating the compound with a large excess of 2N sodium hydroxide aqueous solution in a chloroform-methanol solvent mixture at room temperature for one hour.

Step 69

The reaction is carried out in a similar manner as in Step 32.

Step 70

Compound (XX) can be obtained by reaction of Compound (XIX) with $R^{28}Z$ in an amount of 1 to 10 equivalents in a DMF solvent under ice cooling in the presence of an appropriate base, for example, sodium hydride in an amount of 1 to 1.5 equivalents. The reaction is usually completed in several hours.

Step 71

The reaction is carried out in a similar manner as in Step 68.

Step 72

The reaction is carried out in a similar manner as in Step 70.

Step 73

The reaction is carried out in a similar manner as in Step 32.

Step 74

Compound (I-51) can be obtained by reaction of Compound (I-49)a or Compound (I-50)a with $HNR_2^{29}$ in an amount of 10 to 15 equivalents in a DMF solvent in the presence of an appropriate base, for example, DBU in an amount of 15 to 20 equivalents. The reaction is usually completed at room temperature in one day.

Step 75

Compound (I-52) can be obtained by reaction of Compound (I-47) with hydrazine in an amount of 10 to 50 equivalents in dioxane at 70° to 110° C. for 4 to 10 hours.

Step 76

Compound (I-53) is obtained by reaction of Compound (I-48) with $R^{30}NH_2$ in an amount of 10 to 15 equivalents in an inert solvent at 70° to 110° C. for 4 to 10 hours. The reaction proceeds rapidly by using an appropriate base such as DBU. The inert solvent includes dioxane, DMF, etc.

Step 77

Compound (I-54) is obtained by reaction of Compound (I-53)a with $R^{31}Z$ in an amount of 5 to 10 equivalents in a THF solvent in the presence of an appropriate base, for example, triethylamine in an amount of 10 equivalents. The reaction is usually completed at room temperature in one day.

Step 78

The reaction is carried out in a similar manner as in Step 62.

Step 79

Compound (I-56) is obtained by subjecting Compound (I-1)a to reaction with exces acetic anhydride in a pyridine solvent at room temperature for several hours to protect the two hydroxy groups with acetyl, oxidizing the compound in a similar manner as in Step 66, and then treating the compound with excess 28% aqueous ammonia in a DMF solvent at room temperature for one day.

Isolation and purification of the product after completion of each step described above can be carried out by methods used in conventional organic synthesis, for example, by an appropriate combination of extraction, crystallization, chromatography, etc.

Compound (I) shows a marked cell growth inhibitory activity against human uterine cervical cancer Hela cells, human breast cancer cell MCF 7, human colon adenocarcinoma cell COLO320DM and human lung differented squamous cell carcinoma cell PC-10, and accordingly, antitumor compositions comprising Compound (I) as an effective ingredient are provided.

Compound (I) and its pharmacologically acceptable salts include olephilic and hydrophilic ones and such properties are particularly preferred for pharmaceutical use in some cases. In cases where Compound (I) is used as an anti-tumor composition, each compound is dissolved in physiological saline or a solution of glucose, lactose or mannitol for injection, and usually intravenously administered as an injection in a dose of 0.01 to 20 mg/kg. Alternatively, the compound may be freeze-dried in accordance with the Japanese Pharmacopoeia or may be prepared into injectable powder by adding sodium chloride thereto. Further, the anti-tumor composition may also contain pharmacologically acceptable well-known diluents, adjuvants and/or carriers such as salts which satisfy requirements for medical use. In cases where the compounds is used as an injection, it is sometimes preferred to use auxiliary agents which enhance the solubility. Doses may be appropriately varied depending upon the age and conditions. Administration schedule can also be varied depending upon the conditions and dose. For example, the compound is administered once a day (by single administration or consecutive administration) or intermittently one to three times a week or once every three weeks. Further, oral administration and rectal administration are also possible in the same dose and in the same manner.

The compound can be administered, with appropriate adjuvants, as tablets, powders, granules, syrup, etc. for oral administration and as suppositories for rectal administration.

EXAMPLES

Representative examples of Compound (I) obtained by the processes described above are shown in Table 2 and the intermediates thereof are shown in Table 3.

Examples of preparation of the Compound (I) and the intermediates are respectively shown in Examples and Reference Examples. Compound Nos. correspond to Example Nos.

TABLE 2

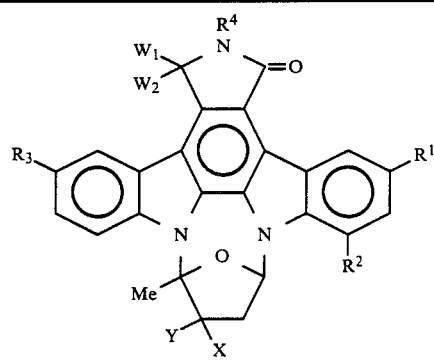

(I)

| Compound No. | $R^1$ | $R^2$ | $R^3$ | $R^4$ | $W_1$ $W_2$ | X | Y |
|---|---|---|---|---|---|---|---|
| 1 | H | H | H | H | H | CONHOH | OH |
| 2 | H | H | H | H | H | $CONH_2$ | OH |
| 3 | H | H | H | H | H | $CONHCH_2CH_2OH$ | OH |
| 4 | H | H | H | H | H | $CO_2Et$ | OH |
| 5 | H | H | H | Cl | H | $CO_2Me$ | OH |
| 6 | Cl | H | H | H | H | $CO_2Me$ | OH |
| 7 | Br | H | H | H | H | $CO_2Me$ | OH |
| 8 | H | H | H | $CONH_2$ | H | $CO_2Me$ | OH |

TABLE 2-continued

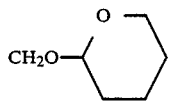

(I)

| Compound No. | R¹ | R² | R³ | R⁴ | W₁ W₂ | X | Y |
|---|---|---|---|---|---|---|---|
| 9 | $NH_2$ | H | H | H | H | $CO_2Me$ | OH |
| 10 | $NH_2$ | H | $NH_2$ | H | H | $CO_2Me$ | OH |
| 11 | H | $NH_2$ | H | H | H | $CO_2Me$ | OH |
| 12 | $NMe_2$ | H | H | H | H | $CO_2Me$ | OH |
| 13 | NHCONHMe | H | H | H | H | $CO_2Me$ | OH |
| 14 | $NHCONH_2$ | H | H | H | H | $CO_2Me$ | OH |
| 15 | OH | H | H | H | H | $CO_2Me$ | OH |
| 16 | OH | H | OH | H | H | $CO_2Me$ | OH |
| 17 | On-Pr | H | H | H | H | $CO_2Me$ | OH |
| 18 | $CH_2OH$ | H | H | H | H | $CO_2Me$ | OH |
| 19 | Me | H | H | H | H | $CO_2Me$ | OH |
| 20 | H | H | H | H | H | $CH_2OH$ | OH |
| 21 | OH | H | H | H | H | $CH_2OH$ | OH |
| 22 | Cl | H | H | H | H | $CH_2OH$ | OH |
| 23 | $NH_2$ | H | H | H | H | $CH_2OH$ | OH |
| 24 | Br | H | H | H | H | $CH_2OH$ | OH |
| 25 | OH | H | OH | H | H | $CH_2OH$ | OH |
| 26 | Me | H | H | H | H | $CH_2OH$ | OH |
| 27 | H | H | H | H | H | $CH_2OCOCH_2CH_2CO_2H$ | OH |
| 28(*) | H | H | H | H | H | 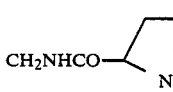 | OH |
| 29 | H | H | H | H | H | $CH_2N_3$ | OH |
| 30 | H | H | H | H | H | $CH_2NH_2$ | OH |
| 31 | H | H | H | H | H | $CH_2NHCH_2CO_2Me$ | OH |
| 32 | H | H | H | H | H | $CH_2NHCH_2CO_2H$ | OH |
| 33 | H | H | H | H | H | $CH_2N=CH-NMe_2$ | OH |
| 34 | H | H | H | H | H | $CH_2NHCOCH_2NH_2$ | OH |
| 35 | H | H | H | H | H | 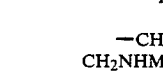 | OH |
| 36 | H | H | H | H | H | $-CH_2O-$ | |
| 37 | H | H | H | H | H | $CH_2NHMe$ | OH |
| 38 | H | H | H | H | H | 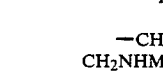 | OH |
| 39 | H | H | H | H | H | 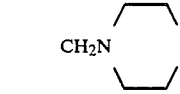 | OH |
| 40 | H | H | H | H | H | 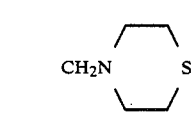 | OH |

TABLE 2-continued

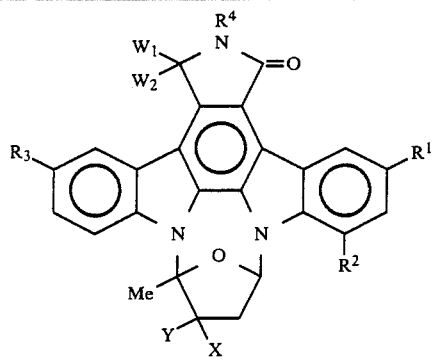

(I)

| Compound No. | R¹ | R² | R³ | R⁴ | W₁ W₂ | X | Y |
|---|---|---|---|---|---|---|---|
| 41 | H | H | H | H | H | CH₂N-piperidine | OH |
| 42 | H | H | H | H | H | CH₂NHCH₂CH=CH₂ | OH |
| 43(*) | H | H | H | H | H | CH₂NHCH₂CH(OH)CH₂OH | OH |
| 44 | H | H | H | H | H | CH₂NHC(=NH)NH₂ | OH |
| 45 | H | H | H | H | H | CH₂SMe | OH |
| 46(*) | H | H | H | H | H | CH₂S(O)Me | OH |
| 47 | H | H | H | H | H | —O— |  |
| 48 | H | H | H | H | H | H | OH |
| 49 | H | H | H | H | H | CHO | OH |
| 50 | H | H | H | H | H | CH=N—OH | OH |
| 51 | H | H | H | H | H | CH=N—NH-(2-imidazolyl) | OH |
| 52 | H | H | H | H | H | CH=N—NH—C(=NH)—NH₂ | OH |
| 53 | H | H | H | H | H | —CH₂—O—CO—O— |  |
| 54 | H | H | H | H | H | —CH₂—O—CS—O— |  |
| 55 | H | H | H | H | H | —CH₂—O—SO—O— |  |
| 56 | H | H | H | H | H | —CH₂N=C(Me)—O— |  |
| 57 | H | H | H | H | H | —CH₂NHCO—O— |  |
| 58 | H | H | H | H | H | —CH₂NHCS—O— |  |
| 59 | H | H | H | H | H | —CH₂NMeCO—O— |  |
| 60 | H | H | H | H | H | —CH₂N(CH₂CH=CH₂)CO—O— |  |
| 61(*) | H | H | H | H | H | —CH₂NCO—O— with CH₂CH(OH)CH₂OH |  |
| 62 | H | H | H | H | H | —CH₂NCO—O— with CH₂CHO |  |
| 63 | H | H | H | H | H | —CH₂NCO—O— with CH₂CH=N—NHC(=NH)NH₂ |  |
| 64 | H | H | H | H | H | —CH₂N=CS(Me)—O— |  |
| 65 | H | H | H | H | O | CO₂Me | OH |
| 66 | H | H | H | H | O | CH₂NH₂ | OH |
| 67 | H | H | H | H | O | CH₂OH | OH |
| 68 | H | H | H | CH₂CH₂Br | O | CO₂Me | OH |

TABLE 2-continued

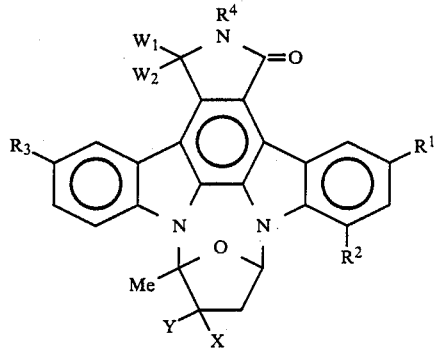

| Compound No. | R¹ | R² | R³ | R⁴ | W₁ W₂ | X | Y |
|---|---|---|---|---|---|---|---|
| 69 | H | H | H | CH₂CH₂NMe₂ | O | CO₂Me | OH |
| 70 | H | H | H | CH₂CH₂NMe₂ | O | CH₂OH | OH |
| 71 | H | H | H | NH₂ | O | CH₂NH₂ | OH |
| 72 | H | H | H | NH₂ | O | CH₂OH | OH |
| 73 | H | H | H | CH₂CH₂NH₂ | O | CH₂OH | OH |
| 74 | H | H | H | H | O | —CH₂NHCO—O— | |
| 75 | H | H | H | H | O | —CH₂N(Me)CO—O— | |
| 76 | H | H | H | H | O | CONHOH | OH |

The compounds of Examples 9, 11, 12, 23, 30–32, 34, 35, 41, 42, 69–71 and 73 are hydrochlorides.
(*)a mixture of diastereoisomers (about 1:1)

TABLE 3

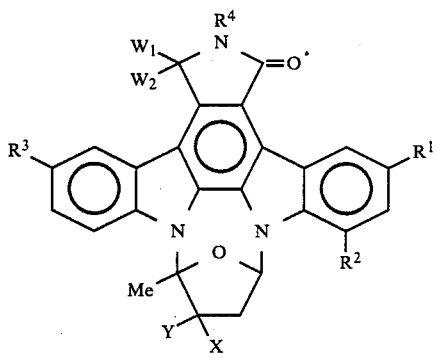

| Compound No. | Reference Example No. | R¹ | R² | R³ | R⁴ | W₁ W₂ | X | Y |
|---|---|---|---|---|---|---|---|---|
| a | 1 | H | H | H | H | H | CO₂H | OAc |
| b | 2 | H | H | H | Ac | H | CO₂Me | OAc |
| c | 3 | NH₂ | H | H | Ac | H | CO₂Me | OAc |
| d | 3 | NH₂ | H | NH₂ | Ac | H | CO₂Me | OAc |
| e | 3 | H | NH₂ | H | Ac | H | CO₂Me | OAc |
| f | 4 | Ac | H | H | Ac | H | CO₂Me | OAc |
| g | 4 | Ac | H | Ac | Ac | H | CO₂Me | OAc |
| h | 5 | CHO | H | H | Ac | H | CO₂Me | OAc |
| i | 6 | CH₂OH | H | H | Ac | H | CO₂Me | OAc |
| j | 7 | CH₂SEt | H | H | Ac | H | CO₂Me | OAc |
| k | 8 | Me | H | H | Ac | H | CO₂Me | OAc |
| l | 9 | H | H | H | H | H | CH₂OTs | OH |
| m | 10 | H | H | H | H | H | CH₂NHCOCH₂NHCbz | OH |
| n | 11 | H | H | H | H | H | CH₂NHCO-[pyrrolidine-N-Boc] | OH |
| o | 12 | H | H | H | H | H | CH₂NHCbz | OH |
| p | 13 | H | H | H | H | O₂ | CH₂NHCbz | OH |

EXAMPLE 1

A solution of 2.5 g of Compound a of Reference Example 1 in 60 ml of thionyl chloride was heated under reflux for 2 hours. Thionyl chloride in the reaction solution was removed under reduced pressure and 40 ml of ethyl ether was added to the solid residue, followed by stirring. Insoluble matters were separated by filtration, washed with ethyl ether, and dried under reduced pressure to give 2.29 g (88%) of o-acetylated acid chloride (III) as pale yellow powder.

To a solution of 206 mg (0.4 mmol) of Compound (III) in 5 ml of anhydrous ($P_2O_5$) chloroform were added 278 mg (4 mmol) of hydroxyamine hydrochloride and 0.56 ml (4 mmol) of triethylamine. After stirring at room temperature for 6 hours, 1 ml of 1N sodium hydroxide aqueous solution and 5 ml of methanol were added to the mixture, followed by stirring for one hour. To the reaction mixture was added 70 ml of THF, and the resulting solution was washed with 1N hydrochloride acid and saturated sodium chloride aqueous solution, and then dried over anhydrous sodium sulfate. The solvent was distilled off under reduced pressure, and the residue was purified by silica gel column chromatography [eluent (hereinafter the same shall apply): chloroform-methanol] to give 91 mg (49%) of Compound 1 as pale yellow powder.

Melting point: 259°–263° C. ($CH_3OH$).

$^1$H-NMR (DMSO-$d_6$+CDCl$_3$) δ: 9.28(d, 1H, J=8 Hz), 8.15–7.8(m, 2H), 7.7–7.15(m, 5H), 7.06(dd, 1H, J=5, 7 Hz), 5.06(d, 1H, J=17 Hz), 4.86(d, 1H, J=17 Hz), 3.36(dd, 1H, J=7, 14 Hz), 2.33(dd, 1H, J=5, 14 Hz), 2.26(s, 3H).

MS (m/z): 469 (M$^+$+1).

EXAMPLE 2

Compound 2 (93 mg, 51%) was obtained as pale yellow powder from Compound a of Reference Example 1 and 28% aqueous ammonia in a similar manner as in Example 1.

Melting point: 262°–265° C. ($CH_2Cl_2$—$CH_3OH$).

$^1$H-NMR (DMSO-$d_6$+CDCl$_3$) δ: 9.30(d, 1H, J=8 Hz), 8.15–7.1(m, 7H), 7.05(dd, 1H, J=5, 7 Hz), 4.99(br s, 2H), 3.33(dd, 1H, J=7, 14 Hz), 2.39(dd, 1H, J=5, 14 Hz), 2.29(s, 3H).

MS (m/z): 453 M$^+$+1).

EXAMPLE 3

Compound 3 (118 mg, 59%) was obtained as pale yellow powder from Compound a of Reference Example 1 and ethanolamine in a similar manner as in Example 1.

Melting point: 237°–239° C.

$^1$H-NMR (DMSO-$d_6$+CDCl$_3$) δ: 9.29(d, 1H, J=8 Hz), 8.2–7.8(m, 3H), 7.7–7.15(m, 4H), 7.04(dd, 1H, J=5, 7 Hz), 4.98(br s, 2H), 3.9–3.45(m, 4H), 3.31 (dd, 1H, J=7, 14 Hz), 2.29(dd, 1H, J=5, 14 Hz), 2.23(s, 3H).

MS (m/z): 497 (M$^+$+1).

EXAMPLE 4

To a suspension of 227 mg (0.5 mmol) of KT-5556 in 20 ml of ethanol was added 1 ml of thionyl chloride, and the mixture was heated under reflux. After two and four hours, 1 ml each of thionyl chloride was further added to the mixture, and heating under reflux was carried out for 8 hours in total. Volatile matters in the reaction mixture were removed under reduced pressure. The residue was purified by silica gel column chromatography (chloroform-methanol) to give 160 mg (66%) of Compound 4 as pale yellow powder.

Melting point: 193°–195° C.

$^1$H-NMR (DMSO-$d_6$) δ: 9.22(d, 1H, J=7.6 Hz), 8.1–7.85 (m, 3H), 7.55–7.25(m, 4H), 7.11(dd, 1H, J=4.9, 7.3 Hz), 5.04(d, 1H, J=17.7 Hz), 4.98(d, 1H, J=17.7 Hz), 4.40(m, 2H), 3.38(dd, 1H, J=7.3, 13.9 Hz), 2.17(s, 3H), 2.02(dd, 1H, J=4.9, 13.9 Hz), 1.43(t, 3H, J=7.1 Hz).

MS (m/z): 481 (M$^+$).

IR (KBr): 3430, 1730, 1675, 1635, 1590, 1460, 745 cm$^{-1}$.

EXAMPLE 5

In 20 ml of chloroform was dissolved 467 mg (1 mmol) of K-252, and 133 mg (1 mmol) of N-chlorosuccinimide and 164 mg (1 mmol) of azobisisobutyronitrile were added to the solution. The mixture was heated under reflux for 3 hours, and then the solvent was distilled off under reduced pressure. The residue was purified by silica gel column chromatography (chloroform) to give 229 mg (46%) of Compound 5 as pale yellow powder showing a melting point of 125° to 129° C.

NMR (CDCl$_3$) δ: 2.20(s, 3H), 2.68(dd, 1H, J=5, 14 Hz), 3.43(dd, 1H, J=7, 14 Hz), 4.12(s, 3H), 4.88(d, 1H, J=15 Hz), 5.04(d, 1H, J=15 Hz), 6.87(dd, 1H, J=5, 7 Hz), 7.24–7.64(m, 5H), 7.84–8.00(m, 2H), 9.00(d, 1H, J=8 Hz).

MS (m/e): 501 (M$^+$).

EXAMPLE 6

In 100 ml of chloroform was dissolved 1.87 g (4 mmol) of K-252, and 4.0 ml (4 mmol) of 0.98 M $Cl_2$/AcOH was added to the solution. The mixture was stirred overnight at room temperature. The precipitates were separated by filtration to give 0.41 g (20%) of Compound 6 as brown powder. Further, the filtrate was concentrated under reduced pressure and the residue was purified by silica gel column chromatography (0.5% MeOH/CHCl$_3$) to give 0.41 g (20%) of Compound 6.

Melting point: 250°–257° C.

NMR (CDCl$_3$+DMSO-$d_6$) δ: 2.08–2.36(m, 1H), 2.20(s, 3H), 3.40(dd, 1H, J=7, 14 Hz), 3.98(s, 3H), 5.01 (s, 2H), 7.10(dd, 1H, J=5, 7 Hz), 7.28–8.12(m, 6H), 9.31(d, 1H, J=2 Hz).

MS (m/e): 501 (M$^+$).

EXAMPLE 7

In 3 ml of pyridine was dissolved 93 mg (0.2 mmol) of K-252. Under ice cooling, 0.024 ml (0.48 mmol) of bromine was added to the solution, followed by stirring overnight. After completion of the reaction, tetrahydrofuran was added to the reaction solution. The mixture was washed successively with 5% sodium thiosulfate aqueous solution and saturated sodium chloride aqueous solution, and then dried over anhydrous magnesium sulfate. The solvent was distilled off under reduced pressure, and the residue was recrystallized from tetrahydrofuran and methanol to give 70 mg (64%) of Compound 7 as yellowish brown powder showing a melting point of 251° to 252° C.

NMR (CDCl$_3$—DMSO-$d_6$) δ: 1.92–2.30(m, 1H), 2.20(s, 3H), 3.12–3.60(m, 1H), 4.00(s, 3H), 5.04(s, 2H), 6.36(s, 1H), 7.04–7.24(m, 1H), 7.36–8.22(m, 6H), 8.64(br. s, 1H), 9.48(br. s, 1H).

MS (m/e): 547 (M$^+$).

EXAMPLE 8

In 5 ml of THF was dissolved 93 mg (0.2 mmol) of K-252, and 0.17 ml (2 mmol) of chlorosulfonyl isocyanate was added to the solution under ice cooling. The mixture was stirred at the same temperature for 2 hours. Then, 1 ml of water was added to the mixture, followed by stirring at 70° C. for one hour. The reaction solution was washed successively with saturated sodium bicarbonate aqueous solution and saturated sodium chloride aqueous solution, and then dried over anhydrous magnesium sulfate. The solvent was distilled off under reduced pressure, and the residue was purified by silica gel column chromatography (2% MeOH/CHCl$_3$) to give 85 mg (77%) of Compound 8 as colorless powder showing a melting point of 280° to 285° C.

NMR (DMSO-d$_6$) δ: 2.17(dd, 1H, J=5, 14 Hz), 2.18(s, 3H), 3.92(dd, 1H, J=7, 14 Hz), 3.94(s, 3H), 5.28(d, 1H, J=18 Hz), 5.34(d, 1H, J=18 Hz), 7.22(dd, 1H, J=5, 7 Hz), 7.32(t, 1H, J=7 Hz), 7.42(t, 1H, J=7 Hz), 7.50–7.58(m, 2H), 7.95–8.01(m, 3H), 9.06(d, 1H, J=8 Hz).

MS (m/e): 554 (M$^+$+1).

EXAMPLE 9

In 35 ml of dichloromethane was dissolved 700 mg (1.22 mmol) of Compound c of Reference Example 3, and 1.2 ml (6.1 mmol) of 28% sodium methylate/methanol solution was added to the solution. After five minutes, 3N hydrochloric acid aqueous solution was added to the mixture. The solvent was distilled off under reduced pressure, and the residue was purified by silica gel column chromatography (chloroform/methanol/DMF=80:10:10). Recrystallization from chloroform-ether gave 507 mg (80%) of Compound 9 as yellow needles showing a melting point higher than 300° C.

NMR (DMSO-d$_6$) δ: 2.09(dd, 1H, J=5, 14 Hz), 2.18(s, 3H), 3.44(dd, 1H, J=7, 14 Hz), 3.96(s, 3H), 5.09 (s, 2H), 6.48(s, 1H), 7.24(dd, 1H, J=5, 7 Hz), 7.18–7.71(m, 3H), 7.74–8.24(m, 3H), 8.77(s, 1H), 9.30(d, 1H, J=2 Hz).

MS (m/e): 483 (MH$^+$).

EXAMPLE 10

Compound 10 (53 mg, 41%) was obtained from 150 mg (0.26 mmol) of Compound d of Reference Example 3 in a similar manner as in Example 9 a black brown powder showing a melting point higher than 300° C.

NMR (DMSO-d$_6$) δ: 1.93(dd, 1H, J=5, 14 Hz), 2.10(s, 3H), 3.36(dd, 1H, J=7, 14 Hz), 3.94(s, 3H), 4.96 (br. s, 2H), 6.48–7.16(m, 3H), 7.24(d, 1H, J=2 Hz), 7.64(d, 1H, J=2 Hz), 7.72(d, 1H, J=2 Hz), 8.62(d, 1H, J=2 Hz).

MS (m/e): 498 (M$^+$+1).

EXAMPLE 11

Compound 11 (118 mg, 84%) was obtained from 150 mg (0.27 mmol) of Compound e of Reference Example 3 in a similar manner as in Example 9 as black brown powder showing a melting point higher than 300° C.

NMR (DMSO-d$_6$+D$_2$O) δ: 2.04(d, 1H, J=5, 14 Hz), 2.15 (s, 3H), 3.60(dd, 1H, J=7, 14 Hz), 3.93(s, 3H), 5.00(d, 1H, J=18 Hz), 5.05(d, 1H, J=18 Hz), 7.21–7.24(m, 1H), 7.27(t, 1H, J=8 Hz), 7.36–7.40(m, 2H), 7.49–7.53(m, 1H), 7.96(d, 1H, J=8 Hz), 8.06 (d, 1H, J=7 Hz), 9.28(d, 1H, J=8 Hz).

MS (m/e): 483 (M$^+$+1).

EXAMPLE 12

In a solvent mixture of 3 ml of methanol and 3 ml of THF was dissolved 155 mg (0.3 mmol) of Compound 9. To the solution were added 1 ml of 35% formaldehyde aqueous solution and then 0.3 mmol of sodium cyanoborohydride. After the mixture was stirred at room temperature for one hour, 10% hydrochloric acid aqueous solution was added to adjust the pH to 1. The reaction mixture was washed with saturated sodium chloride aqueous solution and dried over anhydrous magnesium sulfate. After the solvent was distilled off under reduced pressure, the residue was purified by silica gel column chromatography (5% methanol/chloroform) and recrystallized from chloroform-ethermethanol to give 50 mg (31%) of Compound 12 as black brown powder showing a melting point higher than 300° C.

NMR (DMSO-d$_6$) δ: 2.03(dd, 1H, J=5, 14 Hz), 2.16(s, 3H), 3.20–3.50(1H), 3.40(6H), 3.93(s, 3H), 5.01 (d, 1H, J=17 Hz), 5.07(d, 1H, J=17 Hz), 7.22(dd, 1H, J=5, 7 Hz), 7.36–7.53(m, 2H), 7.90–8.15(m, 4H), 8.75(s, 1H), 9.44(s, 1H).

MS (m/e): 511 (M$^+$).

EXAMPlE 13

In 10 ml of chloroform was dissolved 170 mg (0.3 mmol) of Compound c of Reference Example 3. To the solution were added 0.084 ml (0.6 mmol) of triethylamine and then 0.88 ml (1.5 mmol) of methyl isocyanate. The mixture was stirred at room temperature for one hour, and 2 ml of methanol was added to the reaction mixture. The solvent was distilled off under reduced pressure, and the residue was triturated with methanol to give 150 mg (80.2%) of Compound (VII-1, R$^{15}$=Me, R$^{17}$=Me0 as pale yellow powder showing a melting point higher than 300° C.

MS (m/e): 593 (M$^+$—NHMe).

Compound 13 (89 mg, 93.7%) was obtained from 10 mg (0.17 mmol) of the above compound (VII-1, R$^{15}$=Me, R$^{17}$=Me) in a similar manner as in Example 9 as pale yellow powder showing a melting point higher than 300° C. (recrystallized from methanol).

NMR (CDCl$_3$+DMSO-d$_6$) δ: 2.21(s, 3H), 2.28(dd, 1H, J=5, 14 Hz), 2.83(s, 3H), 4.05(s, 3H), 4.96(br. s, 2H), 6.93(dd, 1H, J=5, 7 Hz), 7.28–7.64(m, 3H), 7.84–8.04(m, 3H), 8.84(d, 1H, J=2 Hz).

MS (m/e): 509 (M$^+$—NHMe).

EXAMPLE 14

In a solvent mixture of 10 ml of THF and 1 ml of acetic acid was dissolved 170 mg (0.3 mmol) of Compound c of Reference Example 3. To the solution was added 1 ml of an aqueous solution of 120 mg (1.5 mmol) of potassium cyanate, and the mixture was stirred at room temperature for one hour. The solvent was distilled off under reduced pressure, and the residue was triturated with water to give 178 mg (97.3%) of Compound (VII-1, R$^{15}$=Me) as yellow powder showing a melting point higher than 300° C.

MS (m/e): 593 (M$^+$—NH$_2$).

Compound 14 (34 mg, 50%) was obtained from 80 mg (0.13 mmol) of the above compound in a similar manner as in Example 9 as pale yellow powder showing a melting point higher than 300° C.

NMR (DMSO-d$_6$) δ: 2.11(dd, 1H,, J=5, 14 Hz), 2.17(s, 3H), 3.20–3.63(1H), 3.97(s, 3H), 5.79(br. s, 2H), 6.40(s, 1H), 6.97–7.23(m, 1H), 7.30–7.70(m, 2H), 7.76–8.10(m, 4H), 8.70(s, 1H), 8.79(s, 1H), 9.20(s, 1H), 9.30(s, 1H).

MS (m/e): 508 (M+—NH$_3$).

EXAMPLE 15 In chloroform was dissolved 20 mg (0.033 mmol) of Compound f of Reference Example 4.

To the solution was added 25 mg (0.15 mmol) of m-chloroperbenzoic acid twice at an interval of one hour, followed by heating under reflux for 3 hours.

After washing with saturated sodium bicarbonate aqueous solution and water, the mixture was dried over anhydrous magnesium sulfate. The solvent was distilled off under reduced pressure, and the residue was purified by silica gel column chromatography (chloroform) and recrystallized from chloroform-ether to give 10 mg (48.0%) of Compound (IX-1, $R^{15}$=Me) as brown powder showing a melting point higher than 300° C.

NMR (CDCl$_3$) δ: 1.79(s, 3H), 2.09(dd, 1H, J=5, 14 Hz), 2.26(s, 3H), 2.40(s, 3H), 2.70(s, 3H), 3.94(dd, 1H, J=7, 14 Hz), 4.00(s, 3H), 5.34(s, 2H), 6.98 (dd, 1H, J=5, 7 Hz), 7.20–7.70(m, 3H), 7.92–8.20(m, 3H), 8.90(d, 1H, J=2 Hz).

MS (m/e): 610 (M+ +1).

Compound 15 (0.3 g, 38.8%) was obtained from 1.0 g (1.6 mmol of the above compound in a similar manner as in Example 9 as reddish brown prisms showing a melting point higher than 300+ C. (recrystallized from chloroform).

NMR (DMSO-d$_6$) δ: 1.97(dd, 1H, J=5, 14 Hz), 2.12(s, 3H), 3.35(dd, 1H, J=7, 14 Hz), 3.92(s, 3H), 5.01 (s, 2H), 6.32(s, 1H), 6.88–7.16(m, 2H), 7.28–7.64(m, 2H), 7.72(d, 1H, J=8 Hz), 7.80–8.20(m, 2H), 8.60(s, 1H), 8.71(d, 1H, J=2 Hz), 9.10(s, 1H).

MS (m/e): 484 (M+ +1).

EXAMPLE 16

Compound (IX-2, $R^{15}$=Me) (80 mg, 42%) was obtained as brown powder from 182 mg (0.3 mmol) of Compound g of Reference Example 4 in a similar manner as in Example 15.

NMR (CDCl$_3$) δ: 1.84(s, 3H), 1.96–2.40(m, 1H), 4.02(s, 3H), 5.36(s, 2H), 6.72–7.08(m, 1H), 7.24–7.64 (m, 3H), 7.76–8.08(m, 2H), 8.48(s, 2H), 9.01(d, J=2 Hz).

Compound 16 (10 mg, 15%) was obtained from 80 mg (0.13 mmol) of the above compound in a similar manner as in Example 9 as yellow powder showing a melting point higher than 300° C.

NMR (DMSO-d$_6$) δ: 1.97(dd, 1H, J=5, 14 Hz , 2.10(s, 3H), 3.00–3.50(1H), 3.92(s, 3H), 4.94(s, 2H), 6.23(s, 1H), 6.80–7.12(m, 3H), 7.35(d, 1H, J=2 Hz), 7.65(d, 1H, J=8 Hz), 7.76(d, 1H, J=8 Hz), 8.46(s, 1H), 8.67(d, 1H, J=2 Hz), 9.03(s, 1H), 9.20(s, 1H).

MS (m/e): 500 (M+ +1).

EXAMPLE 17

In 0.5 ml of DMF was suspended 9.6 mg (0.2 mmol) of 50% sodium hydride, and 1 ml of DMF solution of 96 mg (0.2 mmol) of Compound 15 was added to the suspension under ice cooling. After ten minutes, 0.02 ml (0.2 mmol) of n-propyl iodide was added to the mixture at the same temperature, followed by stirring for one hour. After completion of the reaction, saturated ammonium chloride solution was added. The mixture was extracted with chloroform, washed with saturated sodium chloride aqueous solution, and dried over anhydrous magnesium sulfate. The solvent was distilled off under reduced pressure, and the residue was purified by silica gel column chromatography (CHCl$_3$) and recrystallized from dichloromethane-methanol to give 60 mg (57.1%) of Compound 17 as brown needles showing a melting point of 228° to 230° C. (recrystallized from chloroform).

NMR (DMSO-d$_6$) δ: 1.07(t, 3H, J=8 Hz), 1.72–2.24(m, 3H), 2.16(s, 3H), 2.90–3.40(1H), 3.94(s, 3H), 4.08(t, 2H, J=7 Hz), 5.04(br.s, 2H), 6.34(s, 1H), 7.00–7.24(m, 2H), 7.32–7.60(m, 2H), 7.76–8.16(m, 3H), 8.60(s, 1H), 8.87(d, 1H, J=2 Hz).

MS (m/e): 526 (M+ +1).

EXAMPLE 18

Compound 18 (243 mg, 26%) was obtained from 1.11 g (1.91 mmol) of Compound i of Reference Example 6 in a similar manner as in Example 9 as brown powder showing a melting point higher than 300° C.

NMR (DMSO-d$_6$) δ: 2.00(dd, 1H, J=5, 14 Hz), 2.14(s, 3H), 3.26–3.43(m, 1H), 3.92(s, 3H), 4.66(s, 2H), 4.97(d, 1H, J=18 Hz), 5.03(d, 1H, J=18 Hz), 6.33 (s, 1H), 7.11(dd, 1H, J=5, 7 Hz), 7.33–7.37(m, 1H), 7.45–7.50(m, 2H), 7.83(d, 1H, J=8 Hz), 7.49 (d, 1H, J=8 Hz), 8.60 (s, 1H), 9.14(s, 1H).

MS (m/e): 497 (M+).

EXAMPLE 19

Compound 19 (70 mg, 82%) was obtained from 100 mg (0.17 mmol) of Compound k of Reference Example 8 in a similar manner as in Example 9 as light yellow powder showing a melting point higher than 300° C.

NMR (CDCl$_3$) δ: 2.12(s, 3H), 2.38(s, 3H), 2.95(dd, 1H, J=5, 14 Hz), 3.48(dd, 1H, J=7, 14 Hz), 4.04 (s, 3H), 4.24(d, 1H, J=18 Hz), 4.48(d, 1H, J=18 Hz), 5.42(s, 1H), 5.75(s, 1H), 6.78(dd, 1H, J=5, 7 Hz), 6.94–7.20 (m, 2H), 7.28–7.62(m, 2H), 7.81(dd, 1H, J=2, 8 Hz), 8.00(d, 1H, J=8 Hz), 8.40(s, 1H).

MS (m/e): 481 (M+).

EXAMPLE 20

A solution of 7.01 g (15 mmol) of K-252 in 100 ml of anhydrous THF was ice cooled, and 1.14 g (30 mmol) of lithium aluminum hydride was added thereto, followed by stirring at room temperature for 2 hours. After methanol was added to decompose excess reducing agent, the reaction mixture was filtered through Celite. The filtrate was washed with 1N hydrochloric acid and saturated sodium chloride aqueous solution and dried over anhydrous sodium sulfate. The solvent was removed under reduced pressure, and the residue was purified by silica gel column chromatography (chloroform-methanol) to give 5.34 g (81%) of Compound 20 as pale yellow powder.

Melting point: 266°–275° C. (recrystallized from CH$_3$OH).

$^1$H-NMR (DMSO-d$_6$+CDCl$_3$) δ: 9.24(d, 1H, J=8 Hz), 8.2–7.7(m, 3H), 7.6–7.0(m, 4H), 6.74(dd, 1H, J=5, 7 Hz), 4.90(d, 1H, J=18 Hz), 4.69(d, 1H, J=18 Hz), 4.13(d, 1H, J=11 Hz), 3.91(d, 1H, J=11 Hz), 3.29 (dd, 1H, J=7, 14 Hz), 2.38(dd, 1H, J=5, 14 Hz), 2.19(s, 3H).

MS (m/z): 440 (M+ +1).

EXAMPLE 21

In 1 ml of THF was dissolved 48 mg (0.1 mmol) of Compound 15, and 38 ml (1 mmol) of lithium aluminum hydride was added to the solution, followed by stirring at room temperature for one hour. After 0.04 ml of water, 0.04 ml of 15% sodium hydroxide aqueous solution and 0.04 ml of water were added successively, the reaction solution was extracted with THF. The extract was washed with saturated sodium chloride aqueous solution and dried over anhydrous magnesium sulfate. The solvent was distilled off under reduced pressure, and the residue was purified by silica gel column chromatography (2% MeOH—CHCl$_3$) to give 15 mg (33%) of Compound 21 as brown powder showing a melting point higher than 300° C.

NMR (CDCl$_3$+DMSO-d$_6$) δ: 2.00–2.30(m, 1H), 2.20(s, 1H), 3.08–3.36(m, 1H), 3.84–4.04(m, 2H), 4.52 (m, 1H), 4.96(s, 2H), 6.69(dd, 1H, J=5, 7 Hz), 6.92–8.02(m, 6H), 8.63(s, 1H), 8.77(d, 1H, J=2 Hz).

MS (m/e): 455 (M+).

EXAMPLE 22

In a mixture of 15 ml of THF and 3 ml of methanol wad dissolved 412 mg (0.82 mmol) of Compound 6, and 218 mg (5.75 mmol) of sodium borohydride was added to the solution under ice cooling, followed by stirring at the same temperature for 3 hours. After 3N hydrochloric acid aqueous solution was added, the reaction solution was extracted with THF. The extract was washed with saturated sodium chloride aqueous solution and dried over anhydrous magnesium sulfate. The solvent was distilled off under reduced pressure, and the residue was purified by silica gel column chromatography (3% MeOH—CHCl$_3$) to give 174 mg (45%) of Compound 22 as brown powder showing a melting point of 275° to 280° C.

NMR (CDCl$_3$+DMSO-d$_6$) δ: 2.08–2.28(m, 1H), 2.20(s, 3H), 3.12–3.36(m, 1H), 3.76–4.00(m, 2H), 5.00 (s, 2H), 6.80–7.00(m, 1H), 7.20–8.16(m, 6H), 8.40(br.s, 1H), 9.24(s, 1H).

MS (m/e): 474 (M++1).

EXAMPLE 23

Compound 23 (102 mg, 100%) was obtained from 110 mg (0.2 mmol) of Compound 9 in a similar manner as in Example 22 as brown powder showing a melting point higher than 300° C.

NMR (DMSO-d$_6$+D$_2$O) δ: 1.80–2.10(m, 1H), 2.10(s, 3H), 3.04–3.20(m, 1H), 3.84(br.s, 2H), 5.04(br.s, 2H), 6.92–7.16(m, 1H), 7.20–8.20(m, 7H), 9.23 (d, 1H, J=0.2 Hz).

MS (m/e): 455 (MH+).

EXAMPLE 24

Compound 24 (22 mg, 26%) was obtained from 90 mg (0.16 mmol) of Compound 7 in a similar manner as in Example 21 as brown powder showing a melting point of 258° to 268° C.

NMR (CDCl$_3$+DMSO-d$_6$) δ: 2.10(dd, 1H, J=5, 14 Hz), 2.20(s, 3H), 3.20(dd, 1H, J=18, 14 Hz), 3.90(br.s, 2H), 5.00(s, 2H), 5.34(s, 1H), 6.88(dd, 1H, J=5, 8 Hz), 7.20–8.20(m, 6H), 8.36(s, 1H), 9.40(s, 1H).

MS (m/e): 518 (M++1).

EXAMPLE 25

Compound 25 (78 mg, 33%) was obtained from 250 mg (0.49 mmol) of Compound 6 in a similar manner as in Example 21 as brown powder showing a melting point higher than 300° C.

NMR (DMSO-d$_6$+D$_2$O) δ: 2.00(dd, 1H, J=5, 14 Hz), 2.06 (s, 3H), 3.08(dd, 1H, J=7, 14 Hz), 3.78(d, 1H, J=11 Hz), 3.97(d, 1H, J=11 Hz), 4.75(s, 2H), 6.63 (dd, 1H, J=5, 7 Hz), 6.98(dd, 2H, J=2, 8 Hz), 7.26 (s, 1H), 7.31(d, 1H, J=8 Hz), 7.70(d, 1H, J=8 Hz), 8.46(d, 1H, J=2 Hz).

MS (m/e): 472 (M++1).

EXAMPLE 26

Compound 26 (33 mg, 100%) was obtained from 35 mg (0.072 mmol) of Compound 19 in a similar manner as in Example 22 as brown powder showing a melting point of 245° to 250° C.

NMR (CDCl$_3$+DMSO-d$_6$) δ: 2.05(dd, 1H, J=5, 14 Hz), 2.20 (s, 3H), 2.54(s, 3H), 3.16(dd, 1H, J=7, 14 Hz), 3.88(s, 2H), 4.98(s, 2H), 6.82(dd, 1H, J=5, 7 Hz), 7.20–7.60(m, 4H), 7.98(d, 1H, J=8 Hz), 9.06(s, 1H).

MS (m/e): 454 (M++1).

EXAMPLE 27

In 2 ml of DMF was dissolved in 44 mg (0.1 mmol) of Compound 20, and 22 mg (0.22 mol) of succinic anhydride was added to the solution, followed by stirring at 100° C. for 2 hours. Then, 10 ml of water was added to the reaction solution. The precipitates were separated by filtration and purified by thin layer chromatography to give 25 mg (46.4%) of Compound 27 as colorless powder showing a melting point of 198° to 208° C.

NMR (DMSO-d$_6$) δ: 2.09(dd, 1H, J=5, 14 Hz), 2.18(s, 3H), 2.61(t, 2H, J=6 Hz), 2.70–2.74(m, 2H), 3.07(dd, 1H, J=7, 14 Hz), 4.38(d, 1H, J=11 Hz), 4.50(d, 1H, J=12 Hz), 4.97(d, 1H, J=18 Hz), 5.03(d, 1H, J=17 Hz), 5.83(s, 1H), 7.04(dd, 1H, J=5, 7 Hz), 7.27 (t, 1H, J=7 Hz), 7.34(t, 1H, J=7 Hz), 7.45–7.49 (m, 2H), 7.79(d, 1H, J=8 Hz), 8.00(d, 1H, J=8 Hz), 8.05(d, 1H, J=8 Hz), 8.6(1H, s), 9.20(d, 1H, J=8 Hz), 12.32(br.s, 1H).

MS (m/e): 540 (M++1).

EXAMPLE 28

In 10 ml of CHCl$_3$ was dissolved 88 mg (0.2 mmol) of Compound 21, and 18.2 μml (0.2 mmol) of dihydropyran and 5 L of camphor sulfonate were added to the solution, followed by heating under reflux for 4 hours. The reaction solution was washed successively with saturated sodium bicarbonate aqueous solution and saturated sodium chloride aqueous solution, and then dried over anhydrous magnesium sulfate. The solvent was distilled off under reduced pressure, and the residue was purified by silica gel column chromatography (CHCl$_3$) to give 30 mg (29%) of Compound 28 as colorless powder showing a melting point of 201° to 208° C.

NMR (CDCl$_3$) δ: 1.40–2.00(m, 6H), 2.20(s, 3H), 2.40–2.76(m, 1H), 3.00–3.40(m, 1H), 3.52–4.28(m, 4H), 4.52–4.92(m, 3H), 5.50–6.30(m, 1H), 6.50–6.80 (m, 1H), 7.08–7.64(m, 5H), 7.80–8.04(m, 2H), 8.99, 9.07(two d, 1H, J=8 Hz).

MS (m/e): 524 (M++1).

EXAMPLE 29

A solution of 594 mg (1.0 mmol) of Compound 1 of Reference Example 9 and 130 mg (2.0mmol) of sodium azide in 6 ml of DMF was stirred at room temperature overnight. To the reaction mixture was added 50 ml of THF, and the resulting solution was washed with an acid and an alkali. The solvent was removed under reduced pressure, and the residue was purified by silica gel column chromatography (chloroform-methanol) to give 405 mg (87%) of Compound 29 as pale yellow powder.

Melting point: 218°–223° C. (THF—CH$_3$OH).

$^1$H-NMR (DMSO-d$_6$+CDCl$_3$) δ: 9.31(d, 1H, J=8 Hz), 8.15–7.2(m, 7H), 6.87(dd, 1H, J=5, 7 Hz), 5.00(s, 2H), 3.99(d, 1H, J=13 Hz), 3.56(d, 1H, J=13 Hz), 3.21

(dd, 1H, J=7, 14 Hz), 2.37(dd, 1H, J=5, 14 Hz), 2.9(s, 3H).

MS (m/z): 465 (M$^+$+1).

IR (KBr): 3430, 2100, 1670, 1640, 1590, 1460, 745 cm$^{-1}$.

EXAMPLE 30

To a solution of 232 mg (0.5 mmol) of Compound 29 in 7 ml of anhydrous THF was added 114 mg (3.0 mmol) of lithium aluminum hydride, followed by stirring at room temperature for 2 hours. To the reaction mixture was added 30 ml of THF, and the mixture was filtered through Celite. The filtrate was washed with an acid and an alkali. The solvent was removed under reduced pressure, and the residue was purified by silica gel column chromatography (chloroform-methanol) to give 68 mg (31%) of Compound 30 as pale yellow powder.

Melting point: >300° C. (CH$_3$OH).

$^1$H-NMR (DMSO-d$_6$) δ: 9.21(d, 1H, J=7.9 Hz), 8.1–7.7 (m, 3H), 7.55–7.25(m, 4H), 7.00(dd, 1H, J=5.2, 7.4 Hz), 5.04(d, 1H, J=17.5 Hz), 4.97(d, 1H, J=17.5 Hz), 3.25(dd, 1H, J=7.4, 13.6 Hz), 3.13(d, 1H, J=12.9 Hz), 2.88(d, 1H, J=12.9 Hz), 2.12(s, 3H), 1.91(dd, 1H, J=5.2, 13.6 Hz).

MS (m/z): 439 (M$^+$+1).

IR (KBr): 3440, 1665, 1640, 1590, 745 cm$^{-1}$.

EXAMPLE 31

In 10 ml of DMF was dissolved 280 mg (0.64 mmol) of the free amine of Compound 30, and 0.1 ml (1.05 mmol) of methyl bromoacetate and 156 ml (1.28 mmol) of 4-dimethylaminopyridine (DMAP) were added to the solution, followed by stirring at room temperaturee for one day. After the solvent was distilled off under reduced pressure, the residue was purified by silica gel column chromatography (3% MeOH—CHCl$_3$) to give 180 mg (55%) of Compound 31 as pale yellow powder showing a melting point higher than 300° C.

NMR (DMSO-d$_6$) δ: 2.04–3.12(m, 1H), 2.18(s, 3H), 3.32–3.76(m, 1H), 3.86(s, 3H), 4.23(br.s, 2H), 5.06(br.s, 2H), 6.42(br.s, 1H), 7.00–7.80(m, 6H), 7.92–8.20(m, 2H), 8.69(br.s, 1H), 9.26 (d, 1H, J=8 Hz).

MS (m/e): 511 (MH$^+$).

EXAMPLE 32

In a mixture of 1 ml of THF and 0.3 ml of methanol was dissolved 15 mg (0.029 mmol) of the free amine of Compound 31, and 0.1 ml of 1N sodium hydroxide aqueous solution was added to the solution, followed by stirring at room temperature for 0.5 hour. After the pH was adjusted to 1 to 2 with 3N hydrochloric acid aqueous solution, the mixture was concentrated and the precipitates were separated by filtration. The precipitates were then washed with water to give 14 mg (93%) of Compound 32 as brown powder showing a melting point higher than 300° C.

NMR (DMSO-d$_6$+D$_2$O)δ: 1.96–2.32(m, 1H), 2.15(s, 3H), 3.04–3.80(m, 3H), 3.64(s, 2H), 5.00(br.s, 2H), 6.96–7.84(m, 5H), 7.92–8.20(m, 2H), 9.21(d, 1H, J=8 Hz).

MS (m/e): 497 (MH$^+$).

EXAMPLE 33

In 4 ml of DMF wad dissolved 438 mg (1 mmol) of the free amine of Compound 30, and 0.16 ml (1.2 mmol) of N,N-dimethylformamide dimethylacetal was added to the solution, followed by stirring at room temperature for 2 hours. After the solvent was distilled off under reduced pressure, the residue was crystallized from 10% methanol-chloroform to give 371 mg (75%) of Compound 33 as brown powder showing a melting point of 265° to 267° C.

NMR (DMSO-d$_6$) δ: 1.93(dd, 1H, J=5, 14 Hz), 2.17(s, 3H), 2.88(s, 6H), 3.26(dd, 1H, J=7, 14 Hz), 3.64(s, 2H), 5.02(s, 2H), 5.12(s, 1H), 7.00(dd, 1H, J=5, 7 Hz), 7.20–7.60(m, 4H), 7.58s, 1H), 7.84(d, 1H, J=8 Hz), 8.04(t, 2H, J=8 Hz), 8.57(s, 1H), 9.24(d, 1H, J=8 Hz).

MS (m/e): 494 (M$^+$+1).

EXAMPLE 34

In 3 ml of DMF was dissolved 100 mg (0.15 mmol) of Compound m of Reference Example 10, and 100 mg of 10% palladium carbon was added to the solution, followed by stirring at 40° C. for 5 hours in a stream of hydrogen. The reaction mixture was filtered through Celite and the solvent in the filtrate was distilled off under reduced pressure. The residue was purified by silica gel column chromatography (MeOH—CHCl$_3$-28% NH$_4$OH=5:95:0.25) and then dissolved in THF. 1.7N HCl/AcOEt was added to the solution to convert the product into the hydrochloride, whereby 40 mg (47%) of Compound 34 was obtained as pale yellow powder showing a melting point higher than 300° C.

NMR (DMSO-d$_6$+D$_2$O) δ: 1.88–2.12(m, 1H), 2.18(s, 3H), 2.91(dd, 1H, J=7, 14 Hz), 3.28(s, 2H), 3.72(br.s, 2H), 5.03(s, 2H), 6.96(dd, 1H, J=5, 7 Hz), 7.20–7.64(m, 4H), 7.76(dd, 1H, J=2, 8 Hz), 7.90–8.16(m, 2H), 9.16(d, 1H, J=8 Hz).

MS (m/e): 496 (MH$^+$).

EXAMPLE 35

In a mixture of 5 ml of chloroform and 5 ml of trifluoroacetic acid was dissolved 250 ml of Compound n of Reference Example 11. The solution was stirred at room temperature for one hour, and the solvent was distilled off under reduced pressure. The residue was purified by silica gel column chromatography (MeOH—CHCl$_3$-28% NH$_4$OH=5:95:0.25) and then dissolved in THF. 1.7N HCl/AcOEt was added to the solution to convert the product into the hydrochloride, whereby 110 mg (49%) of Compound 35 was obtained as pale yellow powder showing a melting point higher than 300° C.

NMR (DMSO-d$_6$+D$_2$O) δ: 1.60–2.60(m, 5H), 2.20(s, 3H), 2.84–3.12(m, 1H), 3.12–3.96(m, 4H), 4.28–4.52 (m, 1H), 5.03(s, 2H), 7.02(dd, 1H, J=5, 7 Hz), 7.20–7.64(m, 4H), 7.80(d, 1H, J=8 Hz), 7.96–8.16 (m, 2H), 9.20(d, 1H, J=8 Hz).

MS (m/e): 536 (MH$^+$).

EXAMPLE 36

A solution of 1700 mg (2.9 mmol) of Compound 1 of Reference Example 9 in 50 ml of anhydrous THF was ice cooled and 228 mg (5.8 mmol) of 60% oil sodium hydride was added thereto, followed by stirring at room temperature for 2.5 hours. The reaction solution was washed with an acid and an alkali. The solvent was removed under reduced pressure, and the residue was purified by silica gel column chromatography (chloroform-methanol) to give 884 mg (73%) of Compound 36 as pale yellow powder.

Melting point: 292°–296° C. (decomposed).

$^1$H-NMR (DMSO-d$_6$) δ: 9.31(d, 1H, J=7.5 Hz), 8.1–7.75 (m, 3H), 7.55–7.3(m, 4H), 7.22(dd, 1H, J=1.0, 6.0 Hz), 5.00(s, 2H), ca. 3.35(dd, 1H), 3.29(d, 1H, J=4.4

Hz), 3.03(d, 1H, J=4.4 Hz), 2.446(s, 3H), 2.00(dd, 1H, J=1.0, 14.7 Hz).

MS (m/z): 421 (M+).

IR (KBr): 3450, 1680, 1635, 1590, 1460, 1355, 1315, 1225, 750 cm$^{-1}$.

EXAMPLE 37

To a DMF solution of 126 mg (0.3 mmol) of Compound 1 of Reference Example 9 were added 202 mg (3.0 mmol) of methylamine hydrochloride and 0.449 ml (3.0 mmol) of 1,8-diazabicyclo-[5,4,0]-7-undecene (DBU), followed by stirring at room temperature overnight. To the reaction mixture was added 50 ml of THF, and the resulting solution was washed with saturated sodium chloride aqueous solution and then dried over anhydrous sodium sulfate. The solvent was removed under reduced pressure and the residue was purified by silica gel column chromatography (chloroformmethanol) to give 65 mg (48%) of Compound 37 as pale yellow amorphous powder.

$^1$H-NMR (DMSO-d$_6$) δ: 9.21(d, 1H, J=7.9 Hz), 8.1-7.75 (m, 3H), 7.5-7.25(m, 4H), 7.02(dd, 1H, J=5.3, 7.4 Hz), 5.03(d, 1H, J=17.6 Hz), 4.96(d, 1H, J=17.6 Hz), 3.34(dd, 1H, J=7.4, 13.4 Hz), 3.07(d, 1H, J=11.7 Hz), 2.86(d, 1H, J=11.7 Hz), 2.53(s, 3H), 2.14(s, 3H), 1.98(dd, 1H, J=5.3, 13.4 Hz)

MS (m/z): 453 (M$^+$+1).

EXAMPLE 38

Compound 38 (85 g, 64%) was obtained as pale yellow powder from Compound 1 of Reference Example 9 and morpholine in a similar manner as in Example 37.

Melting point: 220°-223° C. (acetone-Et$_2$O).

$^1$H-NMR (DMSO-d$_6$+CDCl$_3$) δ: 9.33(d, 1H, J=8 Hz), 8.1-7.8(m, 3H), 7.7-7.2(m, 4H), 6.81(dd, 1H, J=5, 7 Hz), 5.00(br.s, 2H), 3.85-3.6(m, 4H), 3.57 (dd, 1H, J=7, 14 Hz), 3.1-2.5(m, 6H), ca. 2.17 (dd, 1H), 2.15(s, 3H).

MS (m/z): 509 (M$^+$+1).

EXAMPLE 39

Compound 39 (66 mg, 63%) was obtained from 118 mg (0.2 mmol) of Compound 1 of Reference Example 9 and 0.10 ml (1.0 mmol) of thiomorpholine in a similar manner as in Example 37 as pale yellow powder showing a melting point of 222° to 230° C.

NMR (CDCl$_3$+DMSO-d$_6$) δ: 2.00-2.28(m, 1H), 2.12(s, 3H), 2.60-3.60(m, 11H), 4.98(s, 2H), 5.26(s, 1H), 6.85(dd, 1H, J=5, 7 Hz), 7.16-7.84(m, 5H), 7.92-8.16(m, 2H), 8.33(s, 1H), 9.32(d, 1H, J=8 Hz).

MS (m/e): 525 (M$^+$+1).

EXAMPLE 40

Compound 40 (127 mg, 100%) was obtained from 118 mg (0.2 mmol) of Compound 1 of Reference Example 9 and 86 mg (1 mmol) of piperazine in a similar manner as in Example 37 as yellowish green powder showing a melting point of 169° to 175° C.

NMR (DMSO-d$_6$) δ: 1.90-2.20(m, 1H), 2.12(s, 3H), 2.40-3.88(m, 11H), 5.00(s, 2H), 5.40(s, 1H), 6.96-7.60(m, 4H), 7.81(d, 1H, J=7 Hz), 8.02(t, 2H, J=7 Hz), 8.56(s, 1H), 9.20(d, 1H, J=8 Hz).

MS (m/e): 508 (M$^+$+1).

EXAMPLE 41

Compound 41 (37 mg, 37%) was obtained from 118 mg (0.2 mmol) of Compound 1 of Reference Example 9 and 0.098 mg (1 mmol) of piperazine in a similar manner as in Example 37 as brown powder showing a melting point of 230° to 238° C.

NMR (DMSO-d$_6$) δ: 1.36-2.24(m, 7H), 2.16(s, 3H), 3.00-3.92(m, 7H), 5.02(s, 2H), 6.28(br.s, 1H), 7.16-7.80(m, 6H), 7.92-8.12(m, 2H), 8.63(br.s, 1H), 9.20(d, 1H, J=8 Hz).

MS (m/e): 507 (MH$^+$).

EXAMPLE 42

Compound 42 (283 mg, 59.2%) was obtained from 593 mg (1 mmol) of Compound 1 of Reference Example 9 and 0.75 mg (10 mmol) of allylamine in a similar manner as in Example 37 as brown powder showing a melting point of 165° to 205° C.

NMR (CDCl$_3$) δ: 1.88-2.20(m, 1H), 2.04(s, 3H), 2.68-3.04(m, 1H), 2.92(d, 1H, J=12 Hz), 3.22(d, 1H, J=12 Hz), 3.36-3.64(m, 2H), 4.36(d, 1H, J=17 Hz) 4.56(d, 1H, J=17 Hz), 5.04(s, 1H), 5.12-5.24(m, 2H), 5.80-6.20(m, 1H), 6.48(dd, 1H, J=5, 7 Hz), 6.92-7.60(m, 5H), 7.83(d, 1H, J=7 Hz), 7.96(d, 1H, J=8 Hz), 8.70(d, 1H, J=8 Hz).

MS (m/e): 478 (M$^+$).

EXAMPLE 43

In a solvent mixture of 2 ml of THF and 0.2 ml of pyridine was dissolved 53.2 mg (0.1 mmol) of Compound 42, and 0.5 ml (0.1 mmol) of 0.05 g/ml THF solution of osmium acid was added to the solution. After stirring at room temperature for 30 minutes, a solution of 46 mg (0.44 mmol) of sodium hydrogensulfite in 2 ml of water and 2 ml of pyridine was added to the reaction mixture, followed by stirring at room temperature for one hour.

To the reaction solution was added 20 ml of THF, and the mixture was washed with saturated NaCl aqueous solution and then dried over anhydrous magnesium sulfate. The solvent was distilled off under reduced pressure. The residue was purified by silica gel column chromatography (MeOH—CHCl$_3$-28% NH$_4$OH=5:95:0.5) and then dissolved in THF. 1.7N HCl/AcOEt was added to the solution to convert the product into the hydrochloride, whereby 22 mg (40%) of Compound 43 was obtained as brown powder showing a melting point of 244° to 250° C.

NMR (DMSO-d$_6$+D$_2$O) δ: 2.16, 2.17(two s, 3H), 2.20 (dd, 1H, J=5, 14 Hz), 3.09-3.15(m, 1H), 3.33-3.68 (m, 6H), 4.00-4.07(m, 1H), 4.98(d, 1H, J=18 Hz), 5.06(d, 1H, J=18 Hz), 7.02-7.87(m, 1H), 7.32(t, 1H, J=8 Hz), 7.40(t, 1H, J=7 Hz), 7.50-7.56(m, 2H), 7.68(d, 1H, J=8 Hz), 7.99(d, 1H, J=8 Hz), 8.08(d, 1H, J=8 Hz), 9.19(d, 1H, J=8 Hz).

MS (m/e): 513 (MH$^+$).

EXAMPLE 44

Compound 44 (43 mg, 30%) was obtained as pale yellow powder from Compound 1 of Reference Example 9 and guanidine hydrochloride in a similar manner as in Example 37.

Melting point: 280°-285° C. (CH$_3$OH—Et$_2$O).

$^1$H-NMR (DMSO-d$_6$+CDCl$_3$) δ: 9.33(d, 1H, J=8 Hz), 8.35-7.85(m, 3H), 7.8-7.2(m, 4H), 7.10(dd, 1H, J=5, 7 Hz), 5.03(br. s, 2H), 3.80(br. s, 2H), 3.12(dd, 1H, J=7, 14 Hz), 2.29(dd, 1H, J=5, 14 Hz), 2.22 (s, 3H).

MS (m/z): 463 (M$^+$−17).

EXAMPLE 45

To a solution of 237 mg (0.4 mmol) of Compound 1 of Reference Example 9 in 5 ml of anhydrous THF was added 1.5 ml of 15% sodium methylate solution, followed by stirring at room temperature for 7 hours. To the reaction mixture was added 30 ml of THF, and the resulting solution was washed with an acid and an alkali. The solvent was removed under reduced pressure, and the residue was purified by silica gel column chromatography (chloroform-methanol) to give 96 mg (51%) of Compound 45 as pale yellow powder.

Melting point: 201°–205° C.

$^1$H-NMR (DMSO-$d_6$+CDCl$_3$) δ: 9.30(d, 1H, J=8 Hz), 8.15–7.8(m, 2H), 7.7–7.2(m, 5H), 6.87(dd, 1H, J=5, 7 Hz), 5.08(d, 1H, J=13 Hz), 4.89(d, 1H, J=13 Hz), 3.41(dd, 1H, J=7, 14 Hz), 3.30(d, 1H, J=13 Hz), 3.03(d, 1H, J=13 Hz), 2.36(s, 3H), 2.23(s, 3H).

MS (m/z): 470 (M$^+$−1).

EXAMPLE 46

A solution of 188 mg (0.4 mmol) of Compound 45 in 5 ml of distilled THF was ice cooled, and 2 ml of an aqueous solution of 90 mg (0.42 mmol) of sodium periodate was added thereto, followed by stirring for 7 hours under ice cooling. To the reaction mixture was added 30 ml of THF, and the resulting solution was washed with saturated sodium chloride aqueous solution and then dried over anhydrous sodium sulfate. The solvent was removed under reduced pressure, and the residue was purified by silica gel column chromatography (chloroform-methanol) to give 163 mg (84%) of Compound 46 as pale yellow powder.

Melting point: 235°–240° C.

$^1$H-NMR (DMSO-$d_6$+CDCl$_3$) δ: 9.31(d, 1H, J=8 Hz), 8.2–7.85(m, 2H), 7.8–7.2(m, 5H), 7.2–6.9(m, 1H), 5.02(br. s, 2H), 3.9–3.2(m, 3H), 2.89+2.87(2s, 3H), ca. 2.4(m, 1H), 2.27+2.19(2s, 3H).

MS (m/z): 486 (M$^+$+1).

EXAMPLE 47

To a suspension of 3.96 g (9 mmol) of Compound 20 in 200 ml of methanol were added 2.05 g (9 mmol) of periodic acid and then 50 ml of THF, followed by stirring at room temperature for 2.5 hours. The solvent in the reaction mixture was removed under reduced pressure and the residue was dissolved in THF. The THF solution was washed with an acid and an alkali. The solvent was removed under reduced pressure, and the residue was purified by silica gel column chromatography (chloroform-methanol) to give 3.03 g (83%) of Compound 47 as pale yellow powder.

Melting point: 231°–234° C. (CH$_2$Cl$_2$).

$^1$H-NMR (DMSO-$d_6$) δ: 9.30(d, 1H, J=7.9 Hz), 8.1–7.8 (m, 3H), 7.6–7.3(m, 5H), 4.98(s, 2H), 3.72(dd, 1H, J=7.0, 19.3 Hz), 2.77(d, 1H, J=3 Hz), 2.48(s, 3H).

MS (m/z): 407 (M$^+$).

IR (KBr): 3420, 1770, 1680, 1635, 1595, 1460, 740 cm$^{-1}$.

EXAMPLE 48

To a solution of 340 mg (0.83 mmol) of Compound 47 in 5 ml of THF and 5 ml of EtOH was added 158 mg (4.17 mmol) of NaBH$_4$, followed by stirring at room temperature for one hour. To the reaction mixture was added 50 ml of THF, and the resulting solution was washed with an acid and an alkali and then dried over Na$_2$SO$_4$. The solvent was removed under reduced pressure, and the solid residue obtained was recrystallized from methanol to give 276 mg (81%) of pale yellow Compound 48.

Melting point: 251°–254° C.

$^1$H-NMR (DMSO-$d_6$) δ: 9.22(d, 1H, J=7.8 Hz), 8.1–7.75 (m, 3H), 7.55–7.25(m, 4H), 7.03(dd, 1H, J=4.5, 7.3 Hz), 5.77(d, 1H, J=6.2 Hz, exchangeable), 5.03(d, 1H, J=17.7 Hz), 4.98(d, 1H, J=17.7 Hz), 4.56(m, 1H), 3.14(m, 1H), 2.29(s, 3H), 1.75(m, 1H).

MS (m/z): 409 (M$^+$).

EXAMPLE 49

In 400 ml of THF was dissolved 4.67 g (10 mmol) of K-252, and 50 ml of THF solution of 0.38 g (10 mmol) of lithium aluminum hydride was added to the solution at −20° C., followed by stirring at the same temperature for one hour. After 3N hydrochloric acid aqueous solution was added to adjust the pH to 2, the reaction mixture was filtered through Celite. The filtrate was washed with saturated sodium chloride aqueous solution and then dried over anhydrous magnesium sulfate. The solvent was distilled off under reduced pressure, and the residue was purified by silica gel column chromatography (chloroform) to give 1.56 g (35.7%) of Compound 49 as pale yellow powder showing a melting point higher than 300° C.

NMR (CDCl$_3$+DMSO-$d_6$) δ: 2.04–2.48(m, 1H), 2.24(s, 3H), 3.08–3.76(1H), 4.90(br. s, 2H), 6.91(dd, 1H, J=5, 7 Hz), 7.08–7.60(m, 5H), 7.76–8.08(m, 2H), 9.19(d, 1H, J=8 Hz), 10.10(s, 1H).

MS (m/z): 437 (M$^+$).

EXAMPLE 50

In 5 ml of THF and 0.5 ml of water was dissolved 100 mg (0.23 mmol) of Compound 49, and 79 mg (1.1 mmol) of hydroxylamine hydrochloride was added to the solution, followed by stirring for one day. After the solvent was distilled off under reduced pressure, the residue was purified by silica gel column chromatography (1% methanol-chloroform) to give 85 mg (82%) of Compound 50 as pale yellow powder showing a melting point of 245° to 256° C.

NMR (DMSO-$d_6$) δ: 1.98–2.30(m, 1H), 2.20(s, 3H), 3.16–3.70(m, 1H), 5.03(s, 2H), 6.84–7.08(m, 1H), 7.16–8.20(m, 8H), 8.58(s, 1H), 9.26(d, 1H, J=8 Hz).

MS (m/e): 452 (M$^+$).

EXAMPLE 51

Compound 51 (55 mg, 53%) was obtained from 87 mg (0.2 mmol) of Compound 49 and 181 mg (1.0 mmol) of 2-hydrazino-2-imidazoline hydrobromide in a similar manner as in Example 50 as pale yellow powder showing a melting point higher than 300° C.

NMR (DMSO-$d_6$) δ: 1.68–2.30(m, 1H), 2.08(s, 3H), 3.00–3.70(1H), 5.00(s, 2H), 5.96(s, 1H), 7.00–8.12(m, 8H), 8.56(s, 1H), 9.21(d, 1H, J=8 Hz).

MS (m/e): 520 (M$^+$+1).

EXAMPLE 52

Compound 52 (60 mg, 60%) was obtained from 87 mg (0.2 mmol) of Compound 49 and 264 mg (1.0 mmol) of aminoguanidine sulfate in a similar manner as in Example 50 as pale yellow powder showing a melting point higher than 300° C.

NMR (DMSO-$d_6$) δ: 1.96–2.30(m, 1H), 2.15(s, 3H), 3.04–3.64(m, 1H), 5.02(br. s, 1H), 6.44(s, 1H), 7.00–8.20(m, 8H), 8.60(s, 1H), 9.22(d, 1H, J=8 Hz).

MS (m/e): 494 (M$^+$+1).

EXAMPLE 53

To a solution of 132 mg (0.3 mmol) of Compound 20 in anhydrous THF were added 146 mg (0.9 mmol) of 1,1'-carbonyldiimidazole and 42 μl (0.3 mmol) of triethylamine, followed by stirring at room temperature overnight. To the reaction mixture was added 50 ml of THF, and the resulting solution was washed with an acid and an alkali. The solvent was removed under reduced pressure, and the solid residue was recrystallized from THF-dichloromethane to give 75 mg (54%) of Compound 53 as white crystals.

Melting point: 257°–260° C.

$^1$H-NMR (DMSO-$d_6$) δ: 9.23(d, 1H, J=7.9 Hz), 8.15–7.75 (m, 3H), 7.55–7.25(m, 4H), 7.21(dd, 1H, J=4.3, 7.1 Hz), 5.21(d, 1H, J=9.4 Hz), 5.02(s, 2H), 4.83 (d, 1H, J=9.4 Hz), 3.40(dd, 1H, J=7.1, 14.7 Hz), 2.53(dd, 1H, J=4.3, 14.7 Hz), 2.46(s, 3H).

MS (m/z): 466 ($M^+ +1$).

IR (KBr): 3450, 1810, 1680, 1640, 1590, 1460, 745 cm$^{-1}$.

EXAMPLE 54

Compound 54 (75 mg, 52%) was obtained as pale yellow powder from Compound 20 and 1,1'-thiocarbonyldiimidazole in a similar manner as in Example 53.

Melting point: 255°–258° C. (THF-CH$_3$OH).

$^1$H-NMR (DMSO-$d_6$) δ: 9.24(d, 1H, J=7.9 Hz), 8.15–7.75 (m, 3H), 7.6–7.3(m, 4H), 7.23(dd, 1H, J=4.2, 7.1 Hz), 5.52(d, 1H, J=10.0 Hz), 5.09(d, 1H, J=10.0 Hz), 5.02(s, 2H), 3.48(dd, 1H, J=7.1, 14.8 Hz), 2.65(dd, 1H, J=4.2, 14.8 Hz), 2.44(s, 3H).

MS (m/z): 481 ($M^+$).

IR (KBr): 3440, 1680, 1640, 1590, 1460, 1315, 745 cm$^{-1}$.

EXAMPLE 55

To a solution of 132 mg (0.3 mmol) of Compound 20 in 2 ml of pyridine was added 33 μl (0.45 mmol) of thionyl chloride, followed by stirring at room temperature for one hour. To the reaction mixture was added 50 ml of THF, and the resulting solution was washed with 5% citric acid aqueous solution and saturated sodium chloride aqueous solution and then dried over anhydrous sodium sulfate. The solvent was removed under reduced pressure, and the solid residue was recrystallized from methanol to give 97 mg (71%) of Compound 55 as pale yellow powder.

Melting point: 256°–259° C.

$^1$H-NMR (DMSO-$d_6$) δ: 9.3–9.05(m, 1H), 8.3–7.7(m, 3H), 7.7–7.2(m, 5H), 5.75–4.85(m, 4H), 3.5–3.25(m, 1H), 2.65–2.35(m, 1H), 2.40+2.38(2s, 3H).

MS (m/z): 486 ($M^+ +1$).

EXAMPLE 56

In 7 ml of sulfolane was dissolved 131 mg (0.3 mmol) of the free amine of Compound 30, and 0.057 ml (0.45 mmol) of trimethyl orthoacetate and 3 mg of camphor sulfonic acid were added to the solution, followed by heating at 90° C. for 2.5 hours. To the reaction solution was added 20 ml of water. The precipitates were separated by filtration and purified by silica gel chromatography (1% MeOH—CHCl$_3$) to give 45 mg (32%) of Compound 56 as brown powder showing a melting point of 227° to 233° C.

NMR (CDCl$_3$) δ: 1.84(s, 3H), 2.44(s, 3H), 2.72(dd, 1H, J=5, 14 Hz), 3.20(dd, 1H, J=7, 14 Hz), 4.01 (d, 1H, J=13 Hz), 4.64(d, 1H, J=13 Hz), 5.16(s, 2H), 6.56(br. s, 1H), 6.94(dd, 1H, J=5, 7 Hz), 7.44–7.84(m, 6H), 8.00–8.16(m, 1H), 9.46(d, 1H, J=8 Hz).

MS (m/z): 462 ($M^+$).

EXAMPLE 57

Compound 57 (29 mg, 21%) was obtained as pale yellow powder from the free amine of Compound 30 and 1,1'-carbonyldiimidazole in a similar manner as in Example 53.

Melting point: >300° C. (CH$_2$Cl$_2$—CH$_3$OH).

$^1$H-NMR (DMSO-$d_6$+CDCl$_3$) δ: 9.36(d, 1H, J=8 Hz), 8.2–7.05(m, 8H), 5.06(br. s, 2H), 4.18(d, 1H, J=10 Hz), 3.86(d, 1H, J=10 Hz), 3.20(dd, 1H), 2.41 (s, 3H).

MS (m/z): 465 ($M^+ +1$).

IR (KBr): 3430, 1765, 1670, 1640, 1590, 1460, 745 cm$^{-1}$.

EXAMPLE 58

In 5 ml of DMF was dissolved 120 mg (0.27 mmol) of the free amine of Compound 30, and 98 mg (0.55 mmol) of thiocarbonyldiimidazole was added to the solution under ice cooling, followed by stirring at the same temperature for one hour. To the reaction solution was added 30 ml of THF, and the resulting solution was washed with saturated sodium chloride aqueous solution and then dried over anhydrous magnesium sulfate. The solvent was distilled off under reduced pressure to give 120 mg (93%) of Compound 58 as pale yellow powder showing a melting point higher than 300° C.

NMR (DMSO-$d_6$) δ: 2.10–2.64(m, 1H), 2.32(s, 3H), 3.00–3.52(m, 1H), 4.05(d, 1H, J=11 Hz), 4.38(d, 1H, J=11 Hz), 5.02(s, 2H), 6.96–8.16(m, 7H), 8.60(s, 1H), 9.21(d, 1H, J=8 Hz).

MS (m/e): 481 ($M^+ +1$).

EXAMPLE 59

Compound 59 (245 mg, 58%) was obtained from 400 mg (0.88 mmol) of Compound 37 and 287 mg (1.77 mmol) of 1,1'-carbonyldiimidazole in a similar manner as in Example 53 as yellow powder showing a melting point of 267° to 276° C.

NMR (DMSO-$d_6$) δ: 2.24–2.52(m, 1H), 2.34(s, 3H), 2.88 (s, 3H), 3.08–3.40(m, 1H), 3.80(d, 1H, J=10 Hz), 4.16(d, 1H, J=10 Hz), 5.00(s, 2H), 7.08–7.56(m, 5H), 7.64–7.84(m, 2H), 8.04(d, 1H, J=8 Hz), 8.56 (s, 1H), 9.18(d, 1H, J=8 Hz).

MS (m/e): 479 ($M^+ +1$).

EXAMPLE 60

Compound 60 (2.03 mg, 97%) was obtained from 2.04 mg (4.26 mmol) of Compound 42 and 1.03 mg (6.39 mmol) of 1,1'-carbonyldiimidazole in a similar manner as in Example 53 as pale green powder showing a melting point of 230° to 237° C.

NMR (DMSO-$d_6$) δ: 2.24–2.60(m, 1H), 2.36(s, 3H), 3.16–3.24(m, 1H), 3.82(d, 1H, J=10 Hz), 3.94(d, 2H, J=8 Hz), 4.14(d, 1H, J=10 Hz), 5.03(s, 2H), 5.24–5.52(m, 2H), 5.76–6.20(m, 1H), 7.12–7.92 (m, 7H), 8.10(d, 1H, J=8 Hz), 8.64(s, 1H), 9.23 (d, 1H, J=8 Hz).

MS (m/e): 495 ($M^+ +1$).

EXAMPLE 61

Compound 61 (95 mg, 59%) was obtained from 148 mg (0.3 mmol) of Compound 60 in a similar manner as in Example 43 as yellowish brown powder showing a melting point higher than 300° C.

NMR (DMSO-$d_6$) δ: 2.20–2.60(m, 1H), 2.40(s, 3H), 3.00–4.12(m, 7H), 4.20–4.44(m, 1H), 5.02(s, 2H), 7.16–7.92(m, 7H), 8.09(br. d, 1H, J=8 Hz), 8.62 (br. s, 1H), 9.23(d, 1H, J=8 Hz).

MS (m/e): 539 ($M^+ +1$).

EXAMPLE 62

Compound 62 (42 mg, 69%) was obtained from 64 mg (0.12 mmol) of Compound 61 in a similar manner as in Example 47 as pale yellow powder showing a melting point higher than 300° C.

NMR (DMSO-$d_6$) δ: 2.10–2.60(m, 1H), 2.40(s, 3H), 3.04–3.60(m, 1H), 3.68–4.60(m, 4H), 5.04(s, 2H), 7.08–8.24(m, 8H), 8.64(br. s, 1H), 9.24(d, 1H, J=8 Hz), 9.64(s, 1H).

MS (m/e): 507 ($M^+ +1$).

EXAMPLE 63

Compound 63 (12 mg, 30%) was obtained from 35 mg (0.07 mmol) of Compound 62 and 93 mg (0.35 mmol) of aminoguanidine sulfate in a similar manner as in Example 50 as pale yellow powder showing a melting point higher than 300° C.

NMR (CDCl$_3$+DMSO-$d_6$) δ: 2.16–2.68(m, 1H), 2.40(s, 3H), 3.00–4.40(m, 5H), 5.05(s, 2H), 7.04–8.20(m, 8H), 8.44(br. s, 1H), 9.34(d, 1H, J=8 Hz).

MS (m/e): 563 ($M^+ +1$).

EXAMPLE 64

In 2 ml of DMF was dissolved 88 mg (0.18 mmol) of Compound 58, and 0.1 ml of methyl iodide was added to the solution, followed by stirring at room temperature for 2.5 hours. After the solvent was distilled off under reduced pressure, the residue was purified by silica gel column chromatography (CHCl$_3$) to give 14 mg (15.7%) of Compound 64 as yellow powder showing a melting point of 223° to 225° C.

NMR (DMSO-$d_6$) δ: 2.08–2.44(m, 1H), 2.24(s, 3H), 2.30(s, 3H), 3.20(dd, 1H, J=7, 14 Hz), 4.06(d, 1H, J=14 Hz), 4.57(d, 1H, J=14 Hz), 5.02(s, 2H), 7.12–8.20(m, 7H), 8.63(s, 1H), 9.24(d, 1H, J=8 Hz).

MS (m/e): 494 ($M^+$).

EXAMPLE 65

To 50 ml of pyridine was added 3 g (30 mmol) of chromic acid under ice cooling, and after 10 minutes, 30 ml of a solution of 2.9 g (6.2 mmol) of K-252 in pyridine was added thereto, followed by stirring at room temperature for one day. The reaction mixture was filtered through Celite, and THF was added to the filtrate. The mixture was washed with saturated sodium chloride aqueous solution and then dried over anhydrous magnesium sulfate (MgSO$_4$). The solvent was distilled off under reduced pressure, and the residue obtained was purified by silica gel column chromatography (chloroform) and recrystallized from chloroform to give 2.53 g (85%) of Compound 65 as yellow powder showing a melting point of 288° to 290° C.

NMR (CDCl$_3$+DMSO-$d_6$) δ: 2.18(s, 3H), 2.38(dd, 1H, J=5, 14 Hz), 3.37(dd, 1H, J=6, 14 Hz), 4.00(s, 3H), 6.05(br. s, 1H), 6.95(dd, 1H, J=5, 6 Hz), 7.20–8.04(m, 6H), 9.08(d, 1H, J=8 Hz), 9.28(d, 1H, J=8 Hz), 10.16(s, 1H).

MS (m/e): 481 ($M^+$).

EXAMPLE 66

Compound 66 (110 mg, 97%) was obtained from 150 mg (0.25 mmol) of Compound o of Reference Example 12 in a similar manner as in Example 34 as yellow needles showing a melting point of 274° to 280° C.

NMR (CDCl$_3$+DMSO-$d_6$) δ: 1.72–2.20(m, 1H), 2.16(s, 3H), 2.90–4.40(m, 6H), 6.84–7.00(m, 1H), 7.20–8.08(m, 7H), 9.09(d, 1H, J=8 Hz), 9.28(d, 1H, J=8 Hz).

MS (m/e): 453 ($M^+ +1$).

EXAMPLE 67

Compound 67 (1.14 mg, 84%) was obtained from 1.44 mg (3 mmol) of Compound 65 in a similar manner as in Example 22 as yellow powder showing a melting point of 278° to 280° C.

NMR (CDCl$_3$+DMSO-$d_6$) δ: 2.13(dd, 1H, J=5, 14 Hz), 2.18(s, 3H), 3.00–3.36(m, 1H), 3.76–4.04(m, 2H), 6.76–7.00(m, 1H), 7.20–7.84(m, 5H), 8.01(d, 1H, J=8 Hz), 9.12(d, 1H, J=8 Hz), 9.30(d, 1H, J=8 Hz).

MS (m/e): 453 ($M^+$).

EXAMPLE 68

In 10 ml of DMF was dissolved 962 mg (2 mmol) of Compound 65, and 80 mg (2 mmol) of 60% sodium hydride was added to the solution under ice cooling. After 10 minutes, 0.17 ml (2 mmol) of 1,1-dibromomethane was added thereto, followed by stirring at room temperature for 2 days. To the reaction solution was added 2 ml of saturated NH$_4$Cl aqueous solution, and the mixture was extracted with THF. After washing with saturated NaCl aqueous solution, the extract was dried over anhydrous magnesium sulfate. The solvent was distilled off under reduced pressure, and the residue was purified by silica gel column chromatography (CHCl$_3$) to give 503 mg (43%) of Compound 68 as yellow prisms showing a melting point of 248° to 249° C.

NMR (CDCl$_3$) δ: 2.20(s, 3H), 2.39(dd, 1H, J=5, 14 Hz), 3.35(dd, 1H, J=7, 14 Hz), 3.68 (t, 2H, J=7 Hz), 3.79(s, 1H), 4.10(t, 2H, J=7 Hz), 6.88(dd, 1H, J=5, 7 Hz), 7.24–7.90(m, 6H), 9.12(d, 1H, J=8 Hz), 9.33(d, 1H, J=8 Hz).

MS (m/e): 588 ($M^+$).

EXAMPLE 69

In DMF was dissolved 480 mg (0.81 mmol) of Compound 68, and 1.32 g (16.2 mmol) of dimethylamine hydrochloride and 24 ml of DBU were added to the solution, followed by stirring at room temperature for one day. The solvent was distilled off under reduced pressure. The residue was purified by silica gel column chromatography (MeOH—CHCl$_3$-28% NH$_4$OH=2.5:97.5:0.1) and then converted into the hydrochloride with 1.7N HCl/AcOEt to give 459 mg (78%) of Compound 69 as yellow powder showing a melting point of 248° to 249° C.

NMR (CDCl$_3$+DMSO-$d_6$) δ: 2.12–2.40(m, 1H), 2.22(s, 3H), 3.02(s, 6H), 3.32–3.84(m, 3H), 4.01(s, 3H), 4.08–4.32(m, 2H), 6.44(br. s, 1H), 7.00–7.28 (m, 1H), 7.32–8.16(m, 6H), 9.08(d, 1H, J=8 Hz), 9.28(d, 1H, J=8 Hz).

MS (m/e): 553 (MH$^+$).

EXAMPLE 70

Compound 70 (80 mg, 30.4%) was obtained from 260 mg (0.47 mmol) of the free amine of Compound 69 ml in a similar manner as in Example 22 as yellow powder showing a melting point of 221° to 230° C.

NMR (DMSO-$d_6$) δ: 1.84–2.20(m, 1H), 2.19(s, 3H), 2.52(s, 6H), 3.00–3.60(m, 3H), 3.72–3.96(m, 2H), 4.00–4.24(m, 2H), 5.18(br. s, 1H), 5.56(s, 1H), 6.94–7.16(m, 1H), 7.24–8.12(m, 6H), 9.00(d, 1H, J=8 Hz), 9.20(d, 1H, J=8 Hz).

MS (m/e): 525 (MH$^+$).

EXAMPLE 71

In 2 ml of dioxane was dissolved 45 mg (0.1 mmol) of Compound 66, and 0.25 ml (5 mmol) of hydrazine hydrate was added to the solution, followed by heating at 100° C. for 2 hours. The solvent was distilled off under reduced pressure. The residue was purified by silica gel column chromatography (MeOH—CHCl$_3$-28% NH$_4$OH=5:95:0.5) and then converted into the hydrochloride with 1.7N HCl/AcOET to give 43 mg (85.5%) of Compound 71 as yellow prisms showing a melting point of 270° to 275° C.

NMR (DMSO-d$_6$+D$_2$O) δ: 2.12-2.44(m, 1H), 2.24(s, 3H), 3.20-3.72(m, 3H), 7.16-8.24(m, 7H), 9.10(d, 1H, J=8 Hz), 9.31(d, 1H, J=8 Hz).

MS (m/e): 468 (MH+).

EXAMPLE 72

Compound 72 (472 mg, 62%) was obtained from 743 mg (1.64 mmol) of Compound 67 and 3.97 mg of hydrazine hydrate in a similar manner as in Example 71 as yellow powder showing a melting point of 245° to 260° C.

NMR (DMSO-d$_6$) δ: B 2.19(dd, 1H, J=5, 14 Hz), 2.16(s, 3H), 3.00-3.40(m, 3H), 3.80(br. s, 2H), 4.96 (br. s, 1H), 5.44(br. s, 1H), 6.88-7.12 (m, 1H), 7.24-8.20(m, 6H), 9.04(d, 1H, J=8 Hz), 9.04(d, 1H, J=8 Hz).

MS (m/e): 469 (M+ +1).

EXAMPLE 73

In 5 ml of DMF was dissolved 285 mg (0.63 mmol) of Compound 67, and 0.42 ml of ethylenediamine and 1.91 ml of DBU were added to the solution, followed by heating at 70° C. for 4 hours. The solvent was distilled off under reduced pressure. The residue was purified by silica gel column chromatography (CHCl$_3$—MeOH-28% NH$_4$OH=100:5:0.1) and then converted into the hydrochloride with 1.7N HCl/AcOEt to give 335 mg (99%) of Compound 73 as yellow powder showing a melting point higher than 300° C.

NMR (DMSO-d$_6$) δ: B 2.19(dd, 1H, J=5, 14 Hz), 2.20(s, 3H), 3.00-3.50(m, 4H), 3.68-4.20(m, 4H), 5.60 (br. s, 1H), 6.96-7.20(m, 1H), 7.24-7.76(m, 4H), 7.92(d, 1H, J=8 Hz), 8.06(d, 1H, J=8 Hz), 8.20 (br. s, 2H), 9.04(d, 1H, J=8 Hz), 9.20 (d, 1H, J=8 Hz).

MS (m/e): 496 (M+).

EXAMPLE 74

Compound 74 (65 mg, 68%) was obtained from 93 mg (0.2 mmol) of Compound 57 in a similar manner as in Example 65 as yellow powder showing a melting point higher than 300° C.

NMR (DMSO-d$_6$) δ: 2.33-2.54(m, 1H), 2.38(s, 3H), 3.27-3.41(m, 1H), 3.81(d, 1H, J=10 Hz), 4.14 (d, 1H, J=10 Hz), 7.24(dd, 1H, J=5, 7 Hz), 7.42 (t, 1H, J=8 Hz), 7.56(t, 1H, J=8 Hz), 7.62(t, 1H, J=8 Hz), 7.84(d, 2H, J=8 Hz), 8.04(s, 1H), 9.02 (d, 1H, J=8 Hz), 9.22(d, 1H, J=8 Hz), 11.16(s, 1H).

MS (m/e): 479 (M+).

EXAMPLE 75

Compound 75 (544 mg, 66.3%) was obtained from 800 mg (1.67 mmol) of Compound 59 in a similar manner as in Example 65 as yellowish brown powder showing a melting point of 290° to 292° C.

NMR (DMSO-d$_6$) δ: 2.24-2.60(m, 1H), 2.34(s, 3H), 2.86(s, 3H), 3.12-3.48(m, 1H), 3.82(d, 1H, J=12 Hz), 3.18(d, 1H, J=12 Hz), 7.16-7.96(m, 1H), 9.00(d, 1H, J=8 Hz), 9.18(d, 1H, J=8 Hz), 10.64 (s, 1H).

MS (m/e): 493 (M+ +1).

EXAMPLE 76

In 30 ml of pyridine was dissolved 2.4 g (5 mmol) of Compound 1, and 1.53 ml of acetic anhydride was added to the solution. The mixture was stirred at room temperature for 3 hours. The solvent was distilled off under reduced pressure, and the residue was purified by silica gel column chromatography (2% MeOH—CHCl$_3$) to give 630 mg (23%) of the diacetyl compound. The compound obtained was oxidized in a similar manner as in Example 65 to give 522 mg (81%) of the imide compound. In 1 ml of DMF was dissolved 56.6 g (0.1 mmol) of the imide compound, and 0.2 ml of 28% NH$_4$OH aqueous solution was added to the solution, followed by stirring at room temperature for one day. The solvent was distilled off under reduced pressure, and the residue was purified by silica gel column chromatography (2% MeOH—CHCl$_3$) to give 36 mg (75%) of Compound 76 as brown powder showing a melting point higher than 300° C.

NMR (CDCl$_3$+DMSO-d$_6$) δ: 2.16-2.44(m, 1H), 2.24(s, 3H), 3.24-3.52(m, 2H), 6.34(br, s, 1H), 6.92-7.12(m, 1H), 7.24-8.20(m, 6H), 8.92-9.40(m, 3H), 10.86(br. s, 1H).

MS (m/e): 483 (M+ +1).

EXAMPLE 77

Compound (I) was examined for C-kinase inhibitory activity and cell growth inhibitory activity by the following method. The results are shown in Table 4.

C-Kinase inhibitory activity test:

C-Kinase inhibitory activity of representative Compounds (I) was measured in accordance with the method of Y. Nishizuka, et al. [J. Biol. Chem., 257, 13341 (1982)]. The test was carried out on test compounds at varied concentrations, and the concentration at which the enzyme activity was inhibited 50% (IC$_{50}$) was determined.

(1) MCF 7 cell growth inhibition test:

MCF 7 cells (4.5×10$^4$ cells/ml) prepared in RPMI 1640 medium containing 10% fetal calf serum, 10 μg/ml insulin and 10$^{-8}$M estradiol are put into wells of a 96-well microtiter plate in the amount of 0.1 ml per each well. After incubation at 37° C. overnight in CO$_2$-incubator, 0.05 ml each of a test sample appropriately diluted with the culture medium is added to each well. In the case of contact for 72 hours, the cells are further cultured in CO$_2$-incubator, and then the culture supernatant is removed and the wells are washed once with PBS(—). Thereafter, 0.1 ml of fresh medium is added to each well, followed by culturing at 37° C. for 72 hours in CO$_2$-incubator. After the culture supernatant is removed, 0.1 ml of the culture medium containing 0.02% Neutral Red is added to each well, followed by culturing at 37° C. for one hour in CO$_2$-incubator, whereby the cells are stained. Then, the culture supernatant is removed and the cells are washed once with physiological saline. The pigment is extracted with 0.001N HCl/30% ethanol and absorption is measured at 550 nm with a microplate reader. By comparing the absorption of intact cells with those of the cells treated with a test compound in known concentrations, the concentration of the test compound at which growth of the cells is inhibited 50% is calculated as IC$_{50}$.

(2) PC-10 cell growth inhibition test:

PC-10 cells (5×10⁴ cells/ml) prepared in MEM medium containing 10% fetal calf serum and 2 mM glutamine are put into wells of a 96-well microtiter plate in the amount of 0.1 ml per each well.

Thereafter, the test is carried out in the same manner as in the MCF 7 cell growth inhibition test.

(3) HeLaS$_3$ cell growth inhibition test:

HeLaS$_3$ cells (3×10⁴ cells/ml) prepared in MEM medium containing 10% fetal calf serum and 2 mM glutamine are put into wells of a 96-well microtiter plate in the amount of 0.1 ml per each well.

Thereafter, the test is carried out in the same manner as in (1).

(4) COLO320DM cell growth inhibition test:

COLO320DM cells (10⁵ cells/ml) prepared in RPMI 1640 medium containing 10% fetal calf serum, 100 U/ml penicillin and 100 μg/ml streptomycin are put into wells of a 96-well microtiter plate in the amount of 0.1 ml per each well. Thereafter, the test is carried out in the same manner as in (1) except that the cells are counted with a microcell counter. By comparing the number of intact cells with those of the cells treated with a test compound in known concentrations, the concentration of the test compound at which growth of the cells is inhibited 50% is calculated as IC$_{50}$.

TABLE 4

C-Kinase Inhibitory Activity and
Cell Growth Inhibitory Activity of the Compounds

| Compound No. | IC$_{50}$ (μg/ml) | | | | |
|---|---|---|---|---|---|
| | C-Kinase | HeLaS$_3$ | PC-10 | MCF-7 | COLO320DM |
| 1 | 0.005 | 0.59 | 0.14 | | |
| 2 | 0.003 | 0.22 | 0.03 | | |
| 3 | 0.018 | 0.95 | 0.68 | | |
| 4 | 0.13 | 0.6 | >1 | | |
| 5 | 0.034 | 0.51 | 0.84 | | |
| 7 | 0.028 | 0.15 | 0.76 | | |
| 9 | 0.175 | 0.01 | | 0.13 | 0.05 |
| 10 | 0.02 | 0.07 | | 0.95 | 0.10 |
| 11 | — | 0.10 | | 0.47 | 0.16 |
| 12 | — | 0.17 | | 0.36 | 0.11 |
| 15 | 0.009 | 0.48 | 0.11 | | |
| 16 | 0.005 | 0.44 | | 0.84 | |
| 20 | 0.02 | 0.07 | 0.11 | 0.55 | 0.05 |
| 21 | 0.01 | 0.46 | | 0.76 | 0.29 |
| 23 | 0.038 | 0.15 | | 0.34 | 0.22 |
| 24 | — | 0.06 | | 0.19 | 0.06 |
| 26 | — | 0.03 | | 0.26 | 0.03 |
| 27 | 0.017 | 0.53 | | >1 | >1 |
| 28 | — | 0.20 | | 1.0 | 0.32 |
| 29 | 0.06 | 0.44 | 0.71 | | |
| 30 | 0.015 | 0.07 | 0.04 | | |
| 31 | — | 0.08 | | 0.8 | 0.31 |
| 32 | 0.01 | 0.22 | | 0.74 | >1 |
| 33 | — | 0.08 | | 0.26 | 1.0 |
| 34 | — | 0.03 | | 0.24 | 0.17 |
| 35 | — | 0.05 | | 0.27 | 0.26 |
| 36 | 0.02 | 0.08 | | 0.52 | 0.12 |
| 38 | 0.10 | 0.18 | | | 0.30 |
| 39 | — | 0.14 | | >1 | 0.38 |
| 40 | — | 0.38 | | >1 | >1 |
| 41 | — | 0.06 | | >1 | 0.07 |
| 43 | 0.02 | 0.19 | | 0.52 | >1 |
| 45 | 0.11 | 0.55 | >1 | | |
| 46 | 0.06 | >1 | 0.27 | | |
| 48 | 0.022 | 0.72 | 0.48 | | |
| 50 | 0.013 | 0.22 | | | 0.17 |
| 51 | 0.031 | 0.23 | | 0.50 | 1.0 |
| 52 | 0.021 | 0.46 | | 0.40 | >1 |
| 54 | 0.015 | 0.28 | 0.11 | 1.0 | 0.08 |
| 55 | 0.038 | 0.14 | 0.64 | | |
| 56 | 0.006 | 0.07 | | 0.40 | 1.0 |
| 57 | 0.02 | 0.04 | 0.10 | 0.15 | 0.37 |
| 58 | 0.017 | 0.28 | 0.69 | | |
| 59 | 0.046 | 0.17 | | 1.0 | 0.39 |
| 63 | 0.053 | 0.20 | | 0.45 | 0.64 |

TABLE 4-continued

C-Kinase Inhibitory Activity and
Cell Growth Inhibitory Activity of the Compounds

| Compound No. | IC$_{50}$ (μg/ml) | | | | |
|---|---|---|---|---|---|
| | C-Kinase | HeLaS$_3$ | PC-10 | MCF-7 | COLO320DM |
| 67 | 0.016 | 0.95 | | | 0.18 |
| 69 | — | 0.88 | | >1 | 0.68 |
| 70 | — | 0.50 | | 0.45 | 0.41 |
| 71 | — | >1 | | 1.0 | >1 |
| 72 | 0.22 | 0.24 | | 0.2 | 0.37 |
| 75 | — | 0.27 | | | 0.18 |
| 76 | — | 0.40 | | 0.62 | 0.06 |

REFERENCE EXAMPLE 1

To a solution of 4.53 g (10 mmol) of Compound KT-5556 in 50 ml of anhydrous pyridine was added 1.42 ml (15 mmol) of acetic anhydride, followed by stirring at room temperature for one hour. The solvent in the reaction mixture was distilled off under reduced pressure and 50 ml of 1N hydrochloric acid was added to the residue, followed by stirring. Insoluble matters were separated by filtration, washed with 1N hydrochloric acid and then with water, and dried under reduced pressure to give 4.79 g (97%) of Compound a as pale yellow powder.

Melting point: 267°–270° C.

$^1$H-NMR (DMSO-d$_6$+CDCl$_3$) δ: 9.36(d, 1H, J=8 Hz), 8.2–7.7(m, 3H), 7.7–7.25(m, 4H), 7.25(dd, 1H, J=5, 7Hz), 5.07(s, 2H), 3.98(dd, 1H, J=7, 14 Hz), 2.35(s, 3H), 2.12(dd, 1H, J=5, 14 Hz), 1.72(s, 3H).

IR (KBr): 3430, 1750, 1680, 1640, 1590, 1460, 1235, 745 cm$^{-1}$.

REFERENCE EXAMPLE 2

In 10 ml of THF was dissolved 2 g (4.2 mmol) of K-252, and 4 ml of acetic anhydride and 2.6 g of dimethylaminopyridine were added to the solution, followed by stirring at room temperature overnight. The reaction solution was washed successively with 2% hydrochloric acid aqueous solution and saturated sodium chloride aqueous solution and then dried over anhydrous magnesium sulfate. The solvent was distilled off under reduced pressure, and the residue was purified by silica gel column chromatography (CHCl$_3$) to give 2.12 g (94%) of Compound b as pale yellow powder.

NMR (CDCl$_3$) δ: 1.76(s, 3H), 2.03(dd, 1H, J=5, 14 Hz), 2.16(s, 3H), 2.56(s, 3H), 3.86(dd, 1H, J=7, 14 Hz), 3.98(s, 3H), 5.07(s, 2H), 6.93(dd, 1H, J=5, 7 Hz), 7.14–7.66(m, 5H), 7.80–8.00(m, 2H), 9.02(d, 1H, J=8 Hz).

REFERENCE EXAMPLE 3

In 100 ml of sulfolane and 50 ml of chloroform was dissolved 5.51 g (10 mmol) of Compound b, and 2.8 g (10.5 mmol) of nitronium tetrafluoroborate was added to the solution. The mixture was heated at 80° C. for 2 hours. After chloroform was distilled off under reduced pressure, 200 ml of water was added to the residue. The precipitates were separated by suction filtration and washed with water and methanol to give a mixture of Compound V-1 (R$^{15}$=Me), Compound V-2 (R$^{15}$=Me) and Compound V-3 (R$^{15}$=Me).

The mixture obtained was then dissolved in 250 ml of DMF and 2 g of 10% palladium/carbon was added to the solution, followed by stirring at room temperature in a stream of hydrogen. After 2 hours, the reaction solution was filtered through Celite and the solvent was distilled off under reduced pressure. The residue was purified by silica gel column chromatography (eluting solvent: chloroform) and recrystallized from a chloroform-ether solvent mixture to give 1.74 g (30%) of Compound c as yellow needles showing a melting point higher than 300° C. and 0.59 g (10%) of Compound d as yellow powder showing a melting point higher than 300° C.

Further, 0.35 g (6.1%) of Compound e was obtained as yellow powder showing a melting point higher than 300° C.

Compound c:

NMR (CDCl$_3$) δ: 1.79(s, 3H), 2.12(dd, 1H, J=5, 14 Hz), 2.28(s, 3H), 2.83(s, 3H), 3.98(dd, 1H, J=7, 14 Hz), 4.03(s, 3H), 5.36(s, 2H), 6.83–7.10(m, 2H), 7.23–7.66(m, 3H), 7.93(dd, 1H, J=2, 8 Hz), 8.60(dd, 1H, J=2, 8 Hz), 8.54(d, 1H, J=2 Hz).

MS (m/e): 567 (M$^+$+1).

Compound d:

NMR (CDCl$_3$) δ: 1.74(s, 3H), 2.08(dd, 1H, J=5, 8 Hz), 2.15(s, 3H), 2.71(s, 3H), 3.83(dd, 1H, J=7, 14Hz), 3.93(s, 3H), 5.00(br. s, 4H), 5.32(s, 2H), 6.80–7.20(m, 3H), 7.28(br. s, 1H), 7.67 (d, 1H, J=8 Hz), 7.70(d, 1H, J=8 Hz), 8.33(d, 1H, J=2 Hz).

MS (m/e): 582 (M$^+$+1).

Compound e:

NMR(DMSO-d$_6$) δ: 1.74(s, 3H), 2.08–2.40(m, 1H), 2.20(s, 3H), 2.60(s, 3H), 3.80–4.12(m, 1H), 3.96(s, 3H), 5.04(br. s, 2H), 5.32(s, 2H), 6.96–7.20(m, 2H), 7.32–7.88(m, 3H), 8.06(d, 1H, J=8 Hz), 8.72(dd, 1H, J=2, 8 Hz).

MS (m/e): 567 (M$^+$+1).

REFERENCE EXAMPLE 4

In 10 ml of dichloromethane was dissolved 110 mg (0.2 mmol) of Compound b, and 133 mg (1 mmol) of aluminum chloride and 0.015 ml (0.2 mmol) of acetyl chloride were added to the solution under ice cooling. The mixture was stirred at the same temperature for 2 hours, and 10 ml of water was added thereto, followed by extraction of the organic layer. The organic layer was washed with saturated sodium chloride aqueous solution and then dried over anhydrous magnesium sulfate. The residue was purified by silica gel column chromatography (chloroform) and recrystallized from chloroform-methanol to give 60 mg (50.8%) of Compound f as colorless prisms showing a melting point higher than 300° C. Further, 5 mg (4%) of Compound g was obtained as yellow prisms showing a melting point higher than 300° C.

Compound f:

NMR (CDCl$_3$) δ: 1.76(s, 3H), 1.09(dd, 1H, J=5, 14 Hz), 2.28(s, 3H), 2.52(s, 3H), 2.69(s, 3H), 3.93(dd, 1H, J=7, 14 Hz), 4.01(s, 3H), 5.20(s, 3H), 6.89 (dd, 1H, J=5, 7 Hz), 7.28–7.72(m, 3H), 7.88–8.24 (m, 3H), 9.68(s, 1H).

MS (m/e): 594 (M$^+$+1).

Compound g:

NMR (CDCl$_3$) δ: 1.82(s, 3H), 2.21(dd, 1H, J=5, 14 Hz), 2.34(s, 3H), 2.75(s, 3H), 2.80(s, 3H), 2.82(s, 3H), 4.06(dd, 1H, J=7, 14 Hz), 4.07(s, 3H), 5.40 (s, 2H), 7.03(dd, 1H, J=5, 7 Hz), 7.56(d, 1H, J=8 Hz), 8.01(d, 1H, J=8 Hz), 8.24(d, 1H, J=8 Hz), 8.25(d, 1H, J=8 Hz), 8.60(s, 1H), 9.84(d, 1H, J=2 Hz).

Ms (m/e): 636 (M$^+$+1).

REFERENCE EXAMPLE 5

In 30 ml of dichloromethane was dissolved 330 mg (0.6 mmol) of Compound b, and 0.46 ml (4.2 mmol) of titanium tetrachloride and 0.11 ml (1.2 mmol) of dichloromethane methyl ether were added to the solution under ice cooling. The mixture was stirred at room temperature for 3 hours, and 10 ml of water was added thereto, followed by extraction. The organic layer was washed with saturated sodium chloride aqueous solution and then dried over anhydrous magnesium sulfate. After the solvent was distilled off under reduced pressure, the residue was purified by silica gel column chromatography (chloroform) and recrystallized from chloroform-methanol to give 130 mg (37%) of Compound h as colorless prisms showing a melting point higher than 300° C.

Compound h:

NMR (DMSO-d$_6$) δ: 1.72(s, 3H), 2.04–2.36(m, 1H), 2.25(s, 3H), 2.68(s, 3H), 3.80–4.08(m, 1H), 4.00(s, 3H), 5.43(s, 2H), 7.20–8.40(m, 7H), 9.60(s, 1H), 10.16(s, 1H).

MS (m/e): 580 (M$^+$+1).

REFERENCE EXAMPLE 6

In a solvent mixture of 20 ml of methanol and 100 ml of chloroform was dissolved 2.51 g (4.3 mmol) of Compound h, and 488 mg (12.4 mmol) of sodium borohydride was added to the solution under ice cooling. The mixture was stirred at the same temperature for 30 minutes. 3N Hydrochloric acid aqueous solution was added to adjust the pH to 2, followed by extraction. The organic layer was washed successively with saturated sodium bicarbonate aqueous solution and saturated sodium chloride aqueous solution and then dried over anhydrous magnesium sulfate. The residue was triturated with ether to give 1.8 g (72%) of Compound i as pale yellow powder showing a melting point of 270° to 277° C.

NMR (CDCl$_3$+CD$_3$OD) δ: 1.80(s, 3H), 2.11(dd, 1H, J=5, 14 Hz), 2.26(s, 3H), 2.64(s, 3H), 3.93(dd, 1H, J=7, 14 Hz), 4.03(s, 3H), 4.86(s, 2H), 5.22(s, 2H), 6.99(dd, 1H, J=5, 7 Hz), 7.40–7.72(m, 4H), 7.80–8.08(m, 2H), 9.04(s, 1H).

MS (m/e): 581 (M$^+$).

REFERENCE EXAMPLE 7

In 30 ml of chloroform was dissolved 500 mg (0.86 mmol) of Compound i, and 0.64 ml (8.6 mmol) of ethanethiol and 199 mg (0.86 mmol) of camphor sulfonic acid were added to the solution, followed by stirring at room temperature for 2 hours. The reaction solution was washed successively with saturated sodium bicarbonate aqueous solution and saturated sodium chloride aqueous solution and then dried over anhydrous magnesium sulfate. The solvent was distilled off under reduced pressure, and the residue was subjected to silica gel column chromatography (5% ethyl acetate-toluene) to give 340 mg (63%) of Compound i as colorless prisms showing a melting point of 181° to 184° C.

NMR (CDCl$_3$) δ: 1.28(t, 3H, J=8 Hz), 1.76(s, 3H), 2.11(dd, 1H, J=5, 14 Hz), 2.26(s, 3H), 2.53(q, 2H, J=8 Hz), 2.80(s, 3H), 3.97(dd, J=7, 14 Hz), 4.00(s, 2H), 4.01(s, 3H), 5.36(s, 2H), 7.02(dd, 1H, J=5, 7 Hz), 7.14–7.80(m, 4H), 7.92–8.20(m, 2H), 9.13(s, 1H).

MS (m/e): 626 (M$^+$).

REFERENCE EXAMPLE 8

In ethyl acetate was dissolved 125 mg (0.2 mmol) of Compound i, and 200 mg of Raney nickel was added to the solution, followed by heating under reflux for 7 hours. The reaction solution was filtered through Celite and the solvent was distilled off under reduced pressure to give 116 mg (100%) of Compound k as pale yellow powder.

NMR (CDCl$_3$) δ: 1.75(s, 3H), 2.04(dd, 1H, J=5, 14 Hz), 2.20(s, 3H), 2.48(s, 3H), 2.61(s, 3H), 3.86(dd, 1H, J=7, 14 Hz), 3.99(s, 3H), 5.08(s, 2H), 6.91(dd, 1H, J=5, 7 Hz), 7.16-7.64(m, 4H), 7.80-8.04(m, 2H), 8.80(s, 1H).

MS (m/e): 566 (M+).

REFERENCE EXAMPLE 9

To a solution of 2.49 g (5.7 mmol) of Compound 20 in 30 ml of anhydrous THF were added 2.70 g (14.2 mmol) of p-toluenesulfonyl chloride, 1.97 ml (14.2 mmol) of triethylamine and 0.69 g (5.7 mmol) of N,N-dimethylaminopyridine, followed by stirring at room temperature overnight. To the reaction mixture was added 100 ml of THF and the resulting solution was washed with an acid and an alkali. The solvent was distilled off under reduced pressure, and the residue was purified by silica gel column chromatography (chloroform-methanol) to give 1.11 g (33%) of Compound l as pale yellow powder.

Melting point: 207°-210° C.

$^1$H-NMR (DMSO-d$_6$+CDCl$_3$) δ: 9.24(d, 1H, J=8 Hz), 8.15-7.8(m, 3H), 7.65-7.2(m, 4H), 6.62(dd, 1H, J=5, 7 Hz), 4.95(d, 1H, J=10 Hz), 4.80(d, 1H, J=10 Hz), 4.45(s, 2H), 3.05(dd, 1H, J=7, 14 Hz), 2.55(s, 3H), 2.36(dd, 1H, J=5, 14 Hz), 2.12(s, 3H).

MS (m/z): 422 [M+-167 (OTs)].

REFERENCE EXAMPLE 10

To 131 mg (0.3 mmol) of the free amine of Compound 30 were added 94 mg (0.45 mmol) of N-Cbz-glycine and 93 mg (0.45 mmol) of dicyclohexylcarbodiimide (DCC), followed by stirring overnight. After completion of the reaction, the precipitates were separated by suction filtration. The solvent in the filtrate was distilled off under reduced pressure, and the residue was purified by silica gel column chromatography (2% MeOH-CHCl$_3$) to give 156 mg (83%) of Compound m as pale yellow powder showing a melting point of 157° to 162° C.

NMR (DMSO-d$_6$) δ: 1.96-2.30(m, 1H), 2.19(s, 3H), 2.58(s, 1H), 2.72-3.08(m, 1H), 3.60-3.88(m, 4H), 5.00(s, 2H), 5.11(s, 2H), 5.72(s, 1H), 6.86-8.20(m, 13H), 8.56(s, 1H), 9.20(dd, 1H, J=2, 8 Hz).

REFERENCE EXAMPLE 11

Compound n (61 mg, 32%) was obtained from 131 mg (0.3 mmol) of the free amine of Compound 30 and 97 mg (0.45 mmol) of Boc-L-proline in a similar manner as in Reference Example 10 as pale yellow powder showing a melting point of 203° to 213° C.

NMR (DMSO-d$_6$+D$_2$O) δ: 1.47(s, 9H), 1.66-2.32(m, 5H), 2.23)br, s. 3H), 2.64-3.04(m, 1H), 3.20-3.64(m, 4H), 4.16-4.44(m, 1H), 4.98(br. s, 2H), 6.88-7.60(m, 5H), 7.90-8.20(m, 3H), 9.16)br. d, 1H, J=8 Hz).

REFERENCE EXAMPLE 12

In 20 ml of THF and 10 ml of water was dissolved 438 mg (1 mmol) of the free amine of Compound 30, and 420 mg (5 mmol) of sodium hydrogencarbonate was added to the solution. Then, 0.21 ml (1.5 mmol) of benzyloxycarbonyl chloride was added thereto under ice cooling, followed by stirring at the same temperature for one hour. The reaction solution was washed with saturated NaCl aqueous solution and then dried over anhydrous magnesium sulfate. The solvent was distilled off under reduced pressure, and the residue was purified by silica gel column chromatography (2% MeOH-CHCl$_3$) to give 282 mg (49.3%) of Compound o as pale yellow powder showing a melting point higher than 300° C.

NMR (DMSO-d$_6$) δ: 1.88-2.20(m, 1H), 2.15(s, 3H), 3.00(dd, 1H, J=7, 14 Hz), 3.40-3.72(m, 2H), 5.00(br. s, 2H), 5.15(s, 2H), 5.60(s, 1H), 5.68-6.96(m, 1H), 7.12-7.72(m, 10H), 7.90-8.16(m, 2H), 8.56(s, 1H), 9.20(d, 1H, J=8 Hz).

REFERENCE EXAMPLE 13

Compound p (170 mg, 64.5%) was obtained from 262 mg (0.45 mmol) of Compound o in a similar manner as in Example 65 as yellow powder showing a melting point of 281° to 285° C.

nNMR (CDCl$_3$+DMSO-d$_6$) δ: 2.00-2.30(m, 1H), 2.18(s, 3H), 3.05(dd, 1H, J=7, 14 Hz), 3.48-3.90(m, 2H), 5.20(s, 2H), 5.69(s, 1H), 6.68-7.00(m, 1H), 7.08-7.70(m, 10H), 8.01(d, 1H, J=7 Hz), 9.08(d, 1H, J=8 Hz), 9.27(d, 1H, J=7 Hz).

We claim:

1. A K-252 derivative represented by formula (I) and a pharmacologically acceptable salt thereof

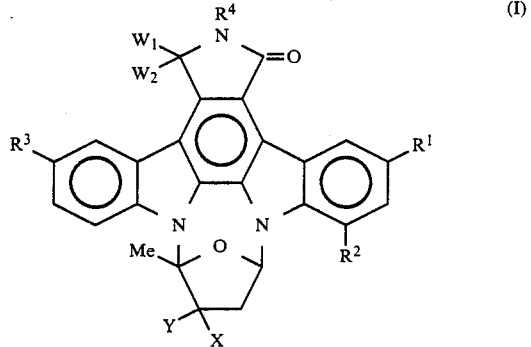

wherein:

R$^1$ represents hydrogen, methyl, hydroxy, hydroxymethyl, lower alkoxy, bromine, chlorine or —NR$^5$R$^6$ (wherein either R$^5$ or R$^6$ is hydrogen and the other is hydrogen, carbamoyl, or lower alkylaminocarbonyl, or both are lower alkyl) and R$^3$ is hydrogen, or R$^1$ and R$^3$ are the same and represent hydroxy, lower alkoxy or amino;

R$^2$ is hydrogen or amino;

R$^4$ is hydrogen, chlorine, carbamoyl, lower alkyl, amino or —CH$_2$CH$_2$R$^7$ (wherein R$^7$ is bromine, amino, di-lower alkylamino, hydroxy or hydroxy-substituted lower alkylamino);

W$_1$ and W$_2$ are hydrogen or both are combined together to represent oxygen;

X is hydrogen, formyl, lower alkoxycarbonyl,

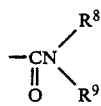

(wherein $R^8$ and $R^9$ are independently hydrogen, lower alkyl or hydroxy-substituted lower alkyl, or $R^8$ is hydrogen and $R^9$ is hydroxy), —$CH_2A$ {wherein A is hydroxy, azido, lower alkylthio, lower alkylsulfenyl,

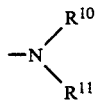

[wherein either $R^{10}$ or $R^{11}$ is hydrogen and the other is hydrogen, lower alkyl, allyl, carboxylic acid-substituted lower alkyl, dihydroxy-substituted lower alkyl, a residue of an α-amino acid in which the hydroxy of the carboxylic acid is removed or lower alkoxycarbonyl-substituted lower alkyl; or both are lower alkyl or chlorine-substituted lower alkyl; or $R^{10}$ and $R^{11}$ are combined together to form —$CH_2CH_2$—B—$CH_2CH_2$— (wherein B is —$CH_2$—, —NH—, —S— or —O—)], —N=CH—$NMe_2$ (wherein Me is methyl), —O-COCH_2CH_2CO_2H or

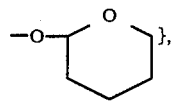

or —C=N—$R^{12}$ (wherein $R^{12}$ is hydroxy, amino, guanidino or 2-imidazolylamino);
Y is hydroxy or carbamoyloxy; or X and Y are combined together to form, as —X—Y—, O=, —CH$_2$O—, —CH$_2$OCOO—, —CH$_2$—O—CS—0—, —CH$_2$—$NR^{13}$—CO—O— —CH$_2$—NH—CS—O—, —CH$_2$—O—SO—O— or

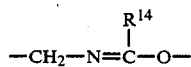

(wherein $R^{14}$ is lower alkyl or lower alkylthio); with the proviso that:
when $W_1$ and $W_2$ are combined together to represent oxygen, $R^1$, $R^2$ and $R^3$ are all hydrogen;
when $R^4$ is lower alkyl, amino or —$CH_2CH_2R^1$, $W_1$ and $W_2$ are combined together to represent oxygen;
when Y is carbamoyloxy, $R^1$, $R^2$, $R^3$, $W_1$ and $W_2$ are all hydrogen, $R^4$ is carbamoyl and X is lower alkoxycarbonyl;
when $R^4$ is chlorine, $R^1$, $R^2$, $R^3$, W, and $W_2$ are all hydrogen and X is lower alkoxycarbonyl;
when X is hydrogen, formyl,

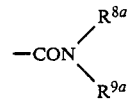

(wherein $R^{8a}$ and $R^{9a}$ are independently hydrogen, lower alkyl, hydroxy-substituted lower alkyl) or $CH_2Aa$ (wherein the Aa representation is the same as the above A representation excluding hydroxy and amino) of —CH=N—$R^{12}$, $R^1$, $R^2$, $R^3$, $R^4$, $W_1$ and $W_2$ are all hydrogen;
when X is CONHOH, $R^1$, $R^2$, $R^3$ and $R^4$ are all hydrogen;
when X is lower alkoxycarbonyl, $R^4$ is hydrogen, chlorine, carbamoyl, lower alkyl or —$CH_2CH_2$-$R^{7a}$ (wherein $R^{7a}$ is bromine or di-lower alkylamino);
when A is aminomethyl, $R^1$, $R^2$ and $R^3$ are hydrogen, and when $W_1$ and $W_2$ are combined together to represent oxygen, $R^4$ is hydrogen or amino and when $W_1$ and $W_2$ are hydrogen, $R^4$ is hydrogen;
when X and Y are combined together to represent, as —X—Y—, —O—, —$CH_2$—O—, —CH$_2$—o—CO—O—, —CH$_2$—O—CS—O—, —CH$_2$—$NR^{13a}$—CO—O— (wherein the $R^{13a}$ representation is the same as the above $R^{13}$ representation excluding hydrogen and lower alkyl), —$CH_2$—NH—CS—O—, —$CH_2$—o—SO—o— or

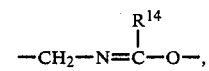

$R^1$, $R^2$, $R^3$, $R^4$, $W_1$ and $W_2$ are all hydrogen;
when X and Y are combined together to represent, as —X—Y, —$CH_2$—$NR^{13b}$—CO—O— [wherein $R^{13b}$ is hydrogen or lower alkyl), $R^1$, $R^2$, $R^3$ and $R^4$ are all hydrogen;
when $R^1$ is methyl, hydroxy, hydroxymethyl, lower alkoxy, bromine, chlorine or —$NR^5R^6$, $R^2$ and $R^4$ are hydrogen;
when $R^2$ is amino, $R^1$ and $R^4$ are hydrogen; and the combinations wherein $R^1$, $R^2$, $R^3$, $R^4$, $W_1$ and $W_2$ are hydrogen, X is methoxycarbonyl and Y is hydroxy are excluded.

2. A compound represented by formula (Ia) and a pharmacologically acceptable salt thereof:

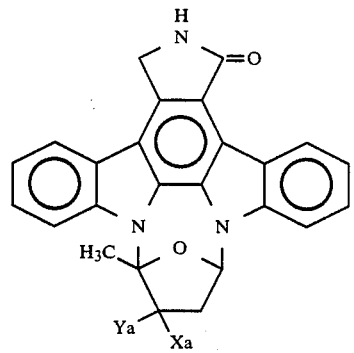

(Ia)

{wherein Xa is alkoxycarbonyl having 3 to 6 carbon atoms,

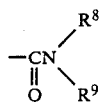

(wherein $R^8$ and $R^9$ are independently hydrogen, lower alkyl or hydroxy-substituted lower alkyl, or $R^8$ is hydrogen and $R^9$ is hydroxy), or —CH₂Ab [wherein Ab is hydroxy, azido, lower alkylthio, lower alkylsulfenyl,

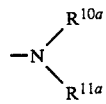

(wherein either $R^{10a}$ or $R^{11a}$ is hydrogen and the other is hydrogen lower alkyl, or both are lower alkyl; or $R^{10a}$ and $R^{11a}$ are combined together to form —CH₂CH₂;₁—O—CH₂CH₂—)]; and Ya is hydroxy; or Xa and Ya are combined together to form, as —Xa—Ya—, —O—, —CH₂—O—, —CH₂O—CO—O—, —CH₂—O—CS—O—, —CH₂—NH—CO—O— or —CH₂—O—SO—O—}.

3. A K-252 derivative represented by formula (Ib) and a pharmacologically acceptable salt thereof:

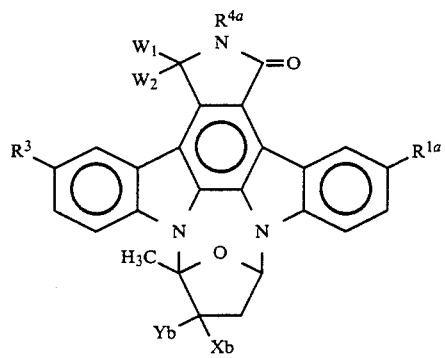

(Ib)

[wherein $R^{1a}$ represents hydrogen, methyl, hydroxymethyl, bromine, hydroxy, lower alkoxy or —NR⁵R⁶ (wherein either R⁵ or R⁶ is hydrogen and the other is hydrogen, carbamoyl or lower alkylaminocarbonyl, or both are lower alkyl) and $R^3$ is hydrogen, or $R^{1a}$ and $R^3$ are the same and represent hydroxy, lower alkoxy or amino; $R^{4a}$ is hydrogen, chlorine, carbamoyl or lower alkyl; $W_1$ and $W_2$ are hydrogen or both are combined together to represent oxygen; Xb is formyl, hydroxymethyl, lower alkoxycarbonyl, —CH=N—R¹² (wherein $R^{12}$ is hydroxy, amino, guanidino or 2-imidazolylamino), and Yb is hydroxy or carbamoyloxy, or Xb and Yb are combined together to form, as —Xb—Yb—, —CH₂—NH—CS—O— or

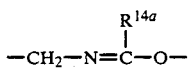

(wherein $R^{14a}$ is lower alkylthio); with the priviso that:
when $W_1$ and $W_2$ is oxygen, both $R^{1a}$ and $R^3$ are hydrogen, Xb is lower alkoxycarbonyl or hydroxymethyl, $R^{4a}$ is hydrogen or lower alkyl and Yb is hydroxy;
when Yb is carbamoyloxy, $R^{1a}$, $R^3$, $W_1$ and $W_2$ are all hydrogen, $R^{4a}$ is carbamoyl and Xb is lower alkoxycarbonyl; when $R^{4a}$ is chlorine, $R^{1a}$, $R^3$, $W_1$ and $W_2$ are all hydrogen and Xb is lower alkoxycarbonyl; when $R^{4a}$ is lower alkyl, $R^{1a}$ and $R^3$ are hydrogen, $W_1$ and $W_2$ are oxygen and Xb is lower alkoxycarbonyl or hydroxymethyl;
when Xb is formul or —CH=N—R¹², $R^{1a}$, $R^3$, $R^{4a}$, $W_1$ and $W_2$ are all hydrogen; when Xb is hydroxymethyl, $R^{1a}$ and $R^3$ are hydrogen and $W_1$ and $W_2$ are oxygen; when Xb and Yb are combined together to form, as —Xb—Yb—,

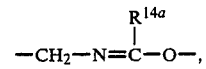

$R^{1a}$, $R^3$, $R^{4a}$, $W_1$ and $W_2$ are all hydrogen; and the combinations wherein $R^{1a}$, $R^3$, $R^{4a}$, $W_1$ and $W_2$ are all hydrogen and Xb is lower alkoxycarbonyl are excluded].

4. A K-252 derivative represented by formula (Ic) and a pharmacologically acceptable salt thereof:

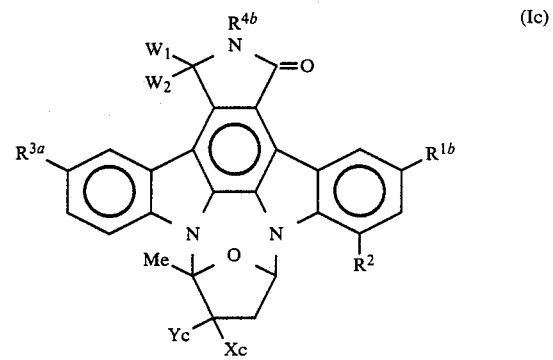

(Ic)

wherein
$R^{1b}$ represents hydrogen, methyl, hydroxy, chlorine, hydroxymethyl, lower alkoxy, bromine or —NR⁵R⁶ (wherein either R⁵ or R⁶ is hydrogen and the other is hydrogen, carbamoyl or lower alkylaminocarbonyl, or both are lower alkyl) and $R^{3a}$ is hydrogen, or $R^{1b}$ and $R^{3a}$ are the same and represent hydroxy, lower alkoxy or amino;
$R^2$ is hydrogen or amino;
$R^{4b}$ is hydrogen, amino or —CH₂CH₂R⁷ (wherein R⁷ is bromine, amino, di-lower alkylamino, hydroxy or hydroxy-substituted lower alkylamino);
$W_1$ and $W_2$ are hydrogen or both are combined together to represent oxygen;
Xc is hydrogen, lower alkoxycarbonyl, hydroxyaminocarbonyl or CH₂Ad {wherein Ad is hydroxy,

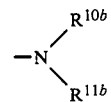

[wherein either $R^{10b}$ or $R^{11b}$ is hydrogen and the other is hydrogen, allyl, carboxylic acid-substituted lower alkyl, dihydroxy-substituted lower alkyl, a residue of an α-amino acid in which the hydroxy of the carboxylic acid is removed or lower alkoxycarbonyl-substituted lower alkyl; or both are chlorine-substituted lower alkyl; or $R^{10b}$ and $R^{11b}$ are combined together to form —$CH_2CH_2$—$V_a$—$CH_2CH_2$— (wherein $B_a$ is —$CH_2$—, —NH— or —S—)], —N=CH—NMe$_2$, —OCOCH$_2$CH$_2$CO$_2$H or 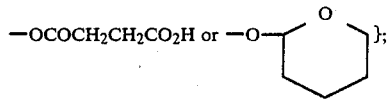

$Y_c$ is hydroxy; or $X_c$ and $Y_c$ are combined together to form, as —$X_c$—$Y_c$—, —$CH_2$—$NR^{13c}$—CO;13 O— [wherein $R^{13c}$ is lower alkyl, allyl, formylmethyl, —$CH_2CH(OH$—$CH_2OH$,

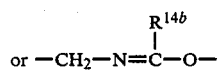

(wherein $R^{14b}$ is lower alkyl);
with the proviso that:
- when $W_1$ and $W_2$ are oxygen, $R^{1b}$, $R^2$ and $R^{3a}$ are all hydrogen;
- when $R^{4b}$ is amino or —$CH_2CH_2R^7$, $W_1$ and $W_2$ are oxygen;
- when $R^{1b}$ is methyl, hydroxy, hydroxymethyl, lower alkoxy, bromine or —$NR^5R^6$, $R^2$ and $R^{4b}$ are hydrogen and $X_c$ is hydroxymethyl;
- when $R^{1b}$ is chlorine, $R^2$ and $R^{4b}$ are hydrogen and $X_c$ is lower alkoxycarbonyl or hydroxymethyl;
- when $R^2$ is amino, $R^{1b}$ and $R^{4b}$ are hydrogen and $X_c$ is lower alkoxycarbonyl or hydroxymethyl;
- when $X_c$ is hydrogen or $CH_2A_e$ (wherein the $A_e$ representation is the same as the above $A_d$ representation excluding hydroxy and amino), $R^{1b}$, $R^2$, $R^{3a}$, $R^{3a}$, $W_1$ and $W_2$ are all hydrogen;
- when $X_c$ is hydroxyaminocarbonyl, $R^{1b}$, $R^2$, $R^{3a}$ and $R^{4b}$ are all hydrogen and $W_1$ and $W_2$ are oxygen;
- when $X_c$ is lower alkoxycarbonyl and $W_1$ and $W_2$ are oxygen, $R^{4b}$ is —$CH_2CH_2R^{7a}$ (wherein $R^{7a}$ is bromine or di-lower alkylamino);
- when $X_c$ is aminomethyl, $R^{1b}$, $R^2$ and $R^{3a}$ are hydrogen, $W_1$ and $W_2$ are oxygen and $R^{4b}$ is hydrogen or amino;
- when $X_c$ is hydroxymethyl and $W_1$ and $W_2$ are oxygen, $R^{4b}$ is amino or —$CH_2CH_2R^7$;
- when $X_c$ and $Y_x$ are combined together to represent, as —$X_c$—$Y_c$—, —$CH_2$—$NR^{13d}$—CO—O— (wherein the $R^{13d}$ representation is the same as the above $R^{13c}$ representation excluding lower alkyl) or

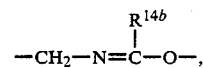

$R^{1b}$, $R^2$, $R^{3a}$, $R^{4b}$, $W_1$ and $W_2$ are all hydrogen;
when $X_c$ and $Y_c$ are combined together to represent, as —$X_c$—$Y_c$—, —$CH_2$—$NR^{13e}$—CO—O— (wherein $R^{13e}$ is lower alkyl), $R^{1b}$, $R^2$, $R^{3a}$ and $R^{4b}$ are hydrogen and $W_1$ and $W_2$ are oxygen; and the combinations wherein $R^{1b}$, $R^2$, $R^{3a}$, $R^{4b}$, $W_1$ and $W_2$ are hydrogen, $X_c$ is methoxycarbonyl and $Y_c$ is hydroxy and the combinations wherein $R^{1b}$, $R^2$, $R^{3a}$, $R^{4b}$, $W_1$ and $W_2$ are hydrogen, $X_c$ is hydroxymethyl and $Y_c$ is hydroxy are removed.

* * * * *